(12) United States Patent
Bandiera et al.

(10) Patent No.: US 8,114,865 B2
(45) Date of Patent: Feb. 14, 2012

(54) INDAZOLE DERIVATIVES AS KINASE INHIBITORS FOR THE TREATMENT OF CANCER

(75) Inventors: Tiziano Bandiera, Pavia (IT); Andrea Lombardi Borgia, Milan (IT); Marcella Nesi, Varese (IT); Ettore Perrone, Milan (IT); Roberto Bossi, Milan (IT); Paolo Polucci, Como (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 258 days.

(21) Appl. No.: 12/520,387

(22) PCT Filed: Dec. 14, 2007

(86) PCT No.: PCT/EP2007/063998
§ 371 (c)(1),
(2), (4) Date: Jun. 19, 2009

(87) PCT Pub. No.: WO2008/074749
PCT Pub. Date: Jun. 26, 2008

(65) Prior Publication Data
US 2010/0197665 A1      Aug. 5, 2010

(30) Foreign Application Priority Data

Dec. 20, 2006   (EP) ..................................... 06126701

(51) Int. Cl.
*A61K 31/415* (2006.01)
*A61K 31/497* (2006.01)
*A61K 31/445* (2006.01)
*A61K 31/44* (2006.01)
*A61K 31/40* (2006.01)
*C07D 243/08* (2006.01)
*C07D 403/12* (2006.01)
*C07D 211/32* (2006.01)
*C07D 401/12* (2006.01)
*C07D 231/56* (2006.01)

(52) U.S. Cl. ............... 514/211.08; 514/252.13; 514/317; 514/337; 514/422; 544/364; 544/371; 546/199; 546/275.7; 548/361.5

(58) Field of Classification Search .................. 540/575; 544/364, 371; 546/199, 275.7; 548/361.5; 514/211.08, 252.13, 317, 337, 422
See application file for complete search history.

(56) References Cited

FOREIGN PATENT DOCUMENTS
WO     WO 03/078403 A2     9/2003
WO     WO 2006/003276 A1     1/2006

OTHER PUBLICATIONS

Bavetsias et al. Bioorganic & Medicinal Chemistry Letters, vol. 17,p. 6567-6571 (2007).*
Milkiewicz et al. Expert Opin.Ther.Patents, vol. 20(12), pp. 1653-1681 (2010).*

* cited by examiner

*Primary Examiner* — James O Wilson
*Assistant Examiner* — Ebenezer O Sackey
(74) *Attorney, Agent, or Firm* — Scully, Scott, Murphy & Presser, P.C.

(57) ABSTRACT

Substituted indazole derivatives of formula (I) and pharmaceutically acceptable salts thereof, as defined in the specification, process for their preparation and pharmaceutical compositions comprising them are disclosed; the compounds of the invention may be useful in therapy in the treatment of diseases associated with a dysregulated protein kinase activity, like cancer formula (I).

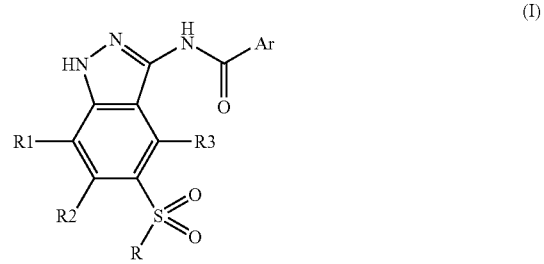

17 Claims, 1 Drawing Sheet

INDAZOLE DERIVATIVES AS KINASE INHIBITORS FOR THE TREATMENT OF CANCER

The present invention relates to certain substituted indazole compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

The insulin-like growth factor 1 receptor (IGF-1R, IGF1R) is a member of the insulin receptor subfamily of receptor tyrosine kinases (RTKs).

There exist several lines of evidence suggesting that IGF-1R signaling can contribute to tumorigenesis, and that interfering with IGF-1R function represents a valid therapeutic option in cancer. For an overview of IGFs and IGF-1R signalling, physiological function, and detailed description of the evidence supporting involvement of this system in human cancer that is summarised above, as well as in other pathologies, the reader is directed to the many reviews on the subject and references contained therein, for example Baserga R. et al, Biochim Biophys Acta vol. 1332, pages F105-F126, 1997; Khandwala H. M. et al, Endocr Rev vol. 21, pages 215-44, 2000; Le Roith D. et al, Endocr Rev vol. 22, pages 53-74, 2001; Valentinis B. et al, Mol Pathol vol. 54, pages 133-7, 2001; Wang Y. et al, Curr Cancer Drug Targets vol. 2, pages 191-207, 2002; Laron, Z. J Clin Endocrinol Metab vol. 89, pages 1031-1044, 2004; Hofmann F et al, Drug Discov Today vol. 10, pages 1041-7, 2005.

Anaplastic lymphoma kinase (ALK) is a tyrosine kinase receptor belonging to the insulin receptor subfamily of RTKs: the ALK gene is located on chromosome 2 and is expressed mainly in neuronal cells, especially during development. The ALK gene is involved in a balanced chromosomal translocation with the Nucleophosmin (NPM) gene on chromosome 5 in a large subset of Anaplastic Large Cell Lymphomas (ALCL). In the ALK+ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM-ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non-Hodgkin's lymphomas, affecting predominantly young male patients. ALK+ALCL accounts for 70% of all ALCLs and is an aggressive disease with systemic signs, and frequent extranodal involvement (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain. Moreover, cell lines established from solid tumors of ectodermal origin like melanomas, breast carcinomas, as well as neuroblastomas, glioblastomas, Ewings sarcomas, retinoblastomas, were found to express the ALK receptor.

In conclusion, interfering with the ALK signalling likely represents a specific and effective way to block tumor cell proliferation in ALCL and possibly other indications.

SUMMARY OF THE INVENTION

Several indazole derivatives useful for the therapy of a variety of diseases such as cancer, neurodegenerative, cardiovascular, metabolic and of the central nervous system, have been disclosed in WO2007075847 in the name of Takeda Pharmaceutical, in WO2006003276, WO2004062662, WO2004022544 and WO2003078403 all in the name of Aventis, in WO2006080450 in the name of Kyowa Hakko Kogyo and in WO2006003276 in the name of University of Connecticut.

Despite these developments, there is still need for effective agents for said diseases. The present inventors have now discovered that compounds of formula (I), described below, are kinase inhibitors and are thus useful in therapy as antitumor agents.

Accordingly, a first object of the present invention is to provide a substituted indazole compound represented by formula (I),

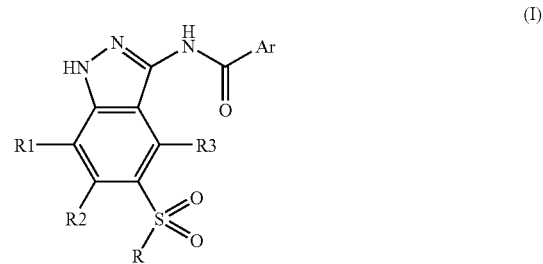

wherein:
Ar is aryl optionally substituted with one or more substituents independently selected from halogen, alkenyl, alkynyl, cyano, nitro, NHCOR4, COR4, NR5R6, NR5COR4, OR7, SR7, SOR10, $SO_2R10$, NHSOR10, $NHSO_2R10$, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein:
  R4 is hydrogen, alkenyl, alkynyl, NR5R6, OR7, SR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl;

R5 and R6 are independently hydrogen, alkenyl, alkynyl, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl or aryl, or R5 and R6, taken together with the nitrogen atom to which they are bonded, may form an optionally substituted heterocyclyl group;

R7 is hydrogen, alkenyl, alkynyl, COR4, SOR10, $SO_2$R10, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl or aryl, wherein R4 is as defined above;

R8 and R9 are independently hydrogen, alkenyl, alkynyl, COR4, an optionally further substituted straight or branched $C_1$-$C_6$ alkyl, $C_3$-$C_6$ cycloalkyl, heterocyclyl or aryl, or R8 and R9, taken together with the nitrogen atom to which they are bonded, may form an optionally substituted heterocyclyl group, wherein R4 is as defined above;

R10 is hydrogen, alkenyl, alkynyl, NR5R6, OR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl, wherein R5, R6, R7, R8 and R9 are as defined above;

R is an optionally further substituted straight or branched $C_1$-$C_6$ alkyl, $C_3$-$C_6$ cycloalkyl, heterocyclyl or aryl;

R1, R2 and R3 are independently hydrogen, halogen, nitro, an optionally further substituted straight or branched $C_1$-$C_6$ alkyl, NR5R6 or OR7, wherein R5, R6 and R7 are as defined above;

and pharmaceutically acceptable salt thereof.

The present invention also provides methods of synthesizing the substituted indazole derivatives of formula (I) prepared through a process consisting of standard synthetic transformations.

The present invention also provides a method for treating diseases caused by and/or associated with dysregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raft, MEK1, MAPK, EGF-R, PDGF-R, FGF-R, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and further more particularly IGF-1R kinase activity, which comprises administering to a mammal in need thereof an effective amount of a substituted indazole compound represented by formula (I) as defined above.

A preferred method of the present invention is to treat a disease caused by and/or associated with dysregulated protein kinase activity selected from the group consisting of cancer, cell proliferative disorders, viral infections, retinopathies including diabetic and neonatal retinopathies and age related macular degeneration, atherosclerosis and conditions involving vascular smooth muscle proliferation or neointimal formation such as restenosis following angioplasty or surgery, graft vessel disease, such as can occur following vessel or organ transplantation, acromegaly and disorders secondary to acromegaly as well as other hypertrophic conditions in which IGF/IGF-1R signalling is implicated, such as benign prostatic hyperplasia, psoriasis, fibrotic lung disease, pulmonary fibrosis, pathologies related to chronic or acute oxidative stress or hyperoxia induced tissue damage, and metabolic disorders in which elevated IGF levels or IGF-1R activity are implicated, such as obesity.

Another preferred method of the present invention, is to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Another preferred method of the present invention, is to treat specific types of cancer such as, but not restricted to, breast cancer, lung cancer, colorectal cancer, prostate cancer, ovarian cancer, endometrial cancer, gastric cancer, clear cell renal cell carcinoma, uveal melanoma, multiple myeloma, rhabdomyo sarcoma, Ewing's sarcoma, Kaposi's sarcoma, and medulloblastoma.

Another preferred method of the present invention, is to treat ALK+Anaplastic Large Cell Lymphomas (ALCL) and possibly other indications in which the ALK activity might play a role, like Neuroblastoma, Rhabdomyo sarcoma, Glioblastoma, Inflammatory Myofibroblastic Tumor, and some kind of Melanomas, Breast Carcinomas, Ewings sarcomas, Retinoblastomas and Non Small Cell Lung Carcinomas (NSCLC).

Another preferred method of the present invention, is to treat cell proliferative disorders such as, but not restricted to, benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and restenosis.

In addition, the method of the present invention also provides tumor angiogenesis and metastasis inhibition.

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with one or more chemotherapeutic agents or radiotherapy. Such agents can include, but are not limited to, anti-hormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

DETAILED DESCRIPTION OF THE INVENTION

The compounds of formula (I) may have one or more asymmetric centres, and may therefore exist as individual optical isomers or racemic mixtures. Accordingly, all the possible isomers, and their mixtures, of the compounds of formula (I) are within the scope of the present invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the pyrazole ring of the compounds of formula (I) rapidly equilibrates in solution to form a mixture of tautomers, as depicted below:

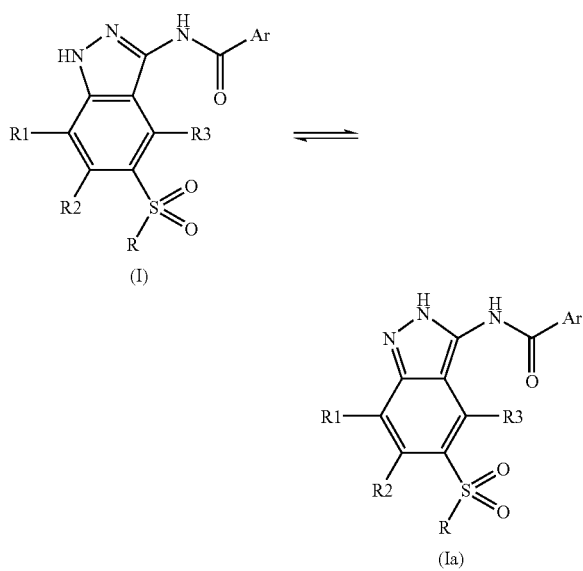

wherein Ar, R, R1, R2 and R3 are as defined above.

Accordingly, in the present invention, where only one tautomer is indicated for the compounds of formula (I), the other tautomer (Ia) is also within the scope of the present invention, unless specifically noted otherwise.

The general terms as used herein, unless otherwise specified, have the meaning reported below.

The term "straight or branched $C_1$-$C_6$ alkyl" refers to a saturated aliphatic hydrocarbon radical, including straight chain and branched chain groups of from 1 to 6 carbon atoms, e.g. methyl, ethyl, propyl, 2-propyl, n-butyl, iso-butyl, tert-butyl, pentyl and the like. The alkyl group may be substituted or unsubstituted. When substituted, the substituent groups are preferably one to three, independently selected from the group consisting of halogen, alkenyl, alkynyl, cyano, nitro, NHCOR4, COR4, NR5R6, NR5COR4, OR7, SR7, SOR10, SO$_2$R10, NHSOR10, NHSO$_2$R10, R8R9N—$C_1$-$C_6$ alkyl, R8O—$C_1$-$C_6$ alkyl, an optionally further substituted $C_3$-$C_6$ cycloalkyl, heterocyclyl and aryl, wherein R4, R5, R6, R7, R8, R9 and R10 are as defined above.

The term "$C_3$-$C_6$ cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted. When substituted, the substituent groups are preferably one or two substituents, independently selected from the group consisting of halogen, alkenyl, alkynyl, cyano, nitro, NHCOR4, COR4, NR5R6, NR5COR4, OR7, SR7, SOR10, SO$_2$R10, NHSOR10, NHSO$_2$R10, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R8, R9 and R10 are as defined above.

The term "heterocyclyl" refers to a 3- to 7-membered, saturated or partially unsaturated carbocyclic ring where one or more carbon atoms are replaced by heteroatoms. These heteroatoms can include, but are not limited to, nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, hexamethyleneiminyl, homopiperazinyl and the like. A heterocyclyl group may be substituted or unsubstituted. When substituted, the substituent groups are preferably one or two substituents, independently selected from the group consisting of halogen, alkenyl, alkynyl, cyano, nitro, NHCOR4, COR4, NR5R6, NR5COR4, OR7, SR7, SOR10, SO$_2$R10, NHSOR10, NHS$_2$R10, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R8, R9 and R10 are as defined above.

The term "aryl" refers to a mono-, bi- or poly-carbocyclic as well as a heterocyclic system with from 1 to 4 rings, either fused or linked to each other by single bonds, wherein at least one of the carbocyclic or heterocyclic rings is aromatic. Not limiting examples of aryl groups are, for instance, phenyl, α- or β-naphthyl, 9,10-dihydroanthracenyl, indanyl, fluorenyl, biphenyl, pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzo isoxazolyl, benzothiazolyl, benzo isothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl and the like.

The term "aryl" may also refer to aromatic carbocyclic or heterocyclic rings further fused or linked to non-aromatic heterocyclic rings, typically 5- to 7-membered heterocycles. Not limiting examples of such aryl groups are, for instance, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

The aryl group can be optionally substituted by one or more, preferably one, two, or three substituents independently selected from halogen, alkenyl, alkynyl, cyano, nitro, NHCOR4, COR4, NR5R6, NR5COR4, OR7, SR7, SOR10, SO$_2$R10, NHSOR10, NHSO$_2$R10, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R8, R9 and R10 are as defined above.

The term "halogen" indicates fluorine, chlorine, bromine or iodine.

The term "alkenyl" indicates straight or branched $C_2$-$C_6$ alkyl groups bearing a double bond. Representative examples include, but are not limited to, ethenyl, 1-propenyl, 2-propenyl, 1- or 2-butenyl, and the like.

The term "alkynyl" indicates straight or branched $C_2$-$C_6$ alkyl groups bearing a triple bond. Representative examples include, but are not limited to, ethynyl, 1-propynyl, 2-propynyl, 1- or 2-butynyl, and the like.

The term "cyano" indicates a —CN residue.

The term "nitro" indicates a —NO$_2$ group.

The term "pharmaceutically acceptable salt" of compounds of formula (I) refers to those salts that retain the biological effectiveness and properties of the parent compound. Such salts include:

acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like;

salts formed when an acidic proton present in a compound of formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

A preferred class of compounds of formula (I) are the compounds wherein:

R is an optionally further substituted $C_3$-$C_6$ cycloalkyl, heterocyclyl or aryl and R1, R2 and R3 are independently hydrogen, halogen or hydroxy.

Another preferred class of compounds of formula (I) are the compounds wherein:

Ar is an optionally further substituted phenyl, pyridinyl, pyrimidinyl or pyrazinyl.

Further preferred compounds of formula (I) are the compounds wherein:

R1, R2 and R3 are hydrogen.

A particularly preferred class of compounds of formula (I) are the compounds wherein:

Ar is an optionally further substituted phenyl or pyridinyl and

R is an optionally further substituted aryl.

A more preferred class of compounds of formula (I) are the compounds wherein:

Ar is a group of formula:

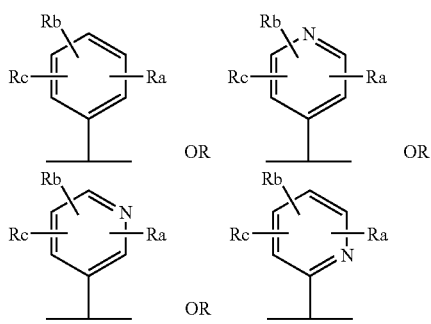

wherein Ra, Rb and Rc are independently hydrogen, halogen, alkenyl, alkynyl, cyano, nitro, NHCOR4, COR4, NR5R6, NR5COR4, OR7, SR7, SOR10, $SO_2R10$, NHSOR10, $NHSO_2R10$, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl, wherein R4, R5, R6, R7, R8, R9 and R10 are as defined above and R is an optionally further substituted aryl.

A most preferred class of compounds of formula (I) are the compounds wherein:

Ar is a group of formula:

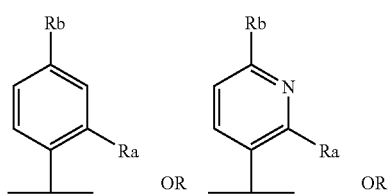

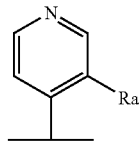

wherein Ra and Rb are as defined above and

R is an optionally further substituted aryl.

A further most preferred class of compounds of formula (I) are the compounds wherein:

Ar is a group of formula:

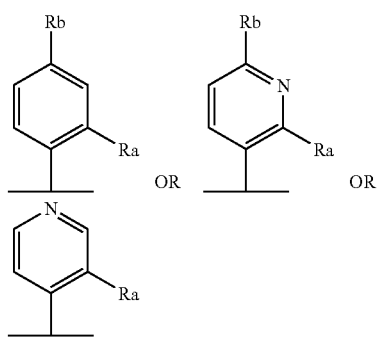

wherein Ra is hydrogen, halogen, nitro, NHCOR4 or NR5R6 and Rb is hydrogen, nitro, NR5R6, OR7 or R8R9N—$C_1$-$C_6$ alkyl wherein R4, R5, R6, R7, R8 and R9 are as defined above and R is an optionally further substituted phenyl.

Specific compounds (cpd.) of the invention are listed below:

1. N-(5-Benzenesulfonyl-1H-indazol-3-yl)-4-(4-methyl-piperazin-1-yl)-benzamide;
2. N-[5-(3-Fluoro-benzenesulfonyl)-1H-indazol-3-yl]-4-(4-methyl-piperazin-1-yl)-benzamide;
3. N-[5-(3,5-Difluoro-benzenesulfonyl)-1H-indazol-3-yl]-4-(4-methyl-piperazin-1-yl)-benzamide;
4. N-(5-Benzenesulfonyl-1H-indazol-3-yl)-4-(4-methyl-piperazin-1-yl)-2-nitro-benzamide;
5. N-[5-(3-Fluoro-benzenesulfonyl)-1H-indazol-3-yl]-4-(4-methyl-piperazin-1-yl)-2-nitro-benzamide;
6. N-[5-(3,5-Difluoro-benzenesulfonyl)-1H-indazol-3-yl]-4-(4-methyl-piperazin-1-yl)-2-nitro-benzamide;
7. 2-Amino-N-(5-benzenesulfonyl-1H-indazol-3-yl)-4-(4-methyl-piperazin-1-yl)-benzamide;
8. 2-Amino-N-[5-(3-fluoro-benzenesulfonyl)-1H-indazol-3-yl]-4-(4-methyl-piperazin-1-yl)-benzamide;
9. 2-Amino-N-[5-(3,5-difluoro-benzenesulfonyl)-1H-indazol-3-yl]-4-(4-methyl-piperazin-1-yl)-benzamide;
10. N-(5-Benzenesulfonyl-1H-indazol-3-yl)-4-(4-methyl-piperazin-1-yl)-2-(tetrahydro-pyran-4-ylamino)-benzamide;
11. N-[5-(3-Fluoro-benzenesulfonyl)-1H-indazol-3-yl]-4-(4-methyl-piperazin-1-yl)-2-(tetrahydro-pyran-4-ylamino)-benzamide;
12. N-[5-(3,5-Difluoro-benzenesulfonyl)-1H-indazol-3-yl]-4-(4-methyl-piperazin-1-yl)-2-(tetrahydro-pyran-4-ylamino)-benzamide;
13. N-[5-(3-Fluoro-benzenesulfonyl)-1H-indazol-3-yl]-2-isobutylamino-4-(4-methyl-piperazin-1-yl)-benzamide;
14. N-[5-(3,5-Difluoro-benzenesulfonyl)-1H-indazol-3-yl]-2-isobutylamino-4-(4-methyl-piperazin-1-yl)-benzamide;

15. 2-Cyclohexylamino-N-[5-(3-fluoro-benzenesulfonyl)-1H-indazol-3-yl]-4-(4-methyl-piperazin-1-yl)-benzamide;
16. 2-Cyclohexylamino-N-[5-(3,5-difluoro-benzenesulfonyl)-1H-indazol-3-yl]-4-(4-methyl-piperazin-1-yl)-benzamide;
17. N-[5-(3-Fluoro-benzenesulfonyl)-1H-indazol-3-yl]-2-(4-hydroxy-cyclohexylamino)-4-(4-methyl-piperazin-1-yl)-benzamide;
18. N-[5-(3,5-Difluoro-benzenesulfonyl)-1H-indazol-3-yl]-2-(4-hydroxy-cyclohexylamino)-4-(4-methyl-piperazin-1-yl)-benzamide;
19. N-[5-(3-Fluoro-benzenesulfonyl)-1H-indazol-3-yl]-4-(4-methyl-piperazin-1-yl)-2-[(pyrrolidin-2-ylmethyl)-amino]-benzamide;
20. N-[5-(3,5-Difluoro-benzenesulfonyl)-1H-indazol-3-yl]-4-(4-methyl-piperazin-1-yl)-2-[(pyrrolidin-2-ylmethyl)-amino]-benzamide;
21. N-[5-(3-Fluoro-benzenesulfonyl)-1H-indazol-3-yl]-4-(4-methyl-piperazin-1-yl)-2-[(piperidin-3-ylmethyl)-amino]-benzamide;
22. N-[5-(3,5-Difluoro-benzenesulfonyl)-1H-indazol-3-yl]-4-(4-methyl-piperazin-1-yl)-2-[(piperidin-3-ylmethyl)-amino]-benzamide;
23. N-[5-(3-Fluoro-benzenesulfonyl)-1H-indazol-3-yl]-4-(4-methyl-piperazin-1-yl)-2-[(1-methyl-pyrrolidin-2-ylmethyl)-amino]-benzamide;
24. N-[5-(3,5-Difluoro-benzenesulfonyl)-1H-indazol-3-yl]-4-(4-methyl-piperazin-1-yl)-2-[(1-methyl-pyrrolidin-2-ylmethyl)-amino]-benzamide;
25. N-[5-(3-Fluoro-benzenesulfonyl)-1H-indazol-3-yl]-4-(4-methyl-piperazin-1-yl)-2-(piperidin-4-ylamino)-benzamide;
26. N-[5-(3,5-Difluoro-benzenesulfonyl)-1H-indazol-3-yl]-4-(4-methyl-piperazin-1-yl)-2-(piperidin-4-ylamino)-benzamide;
27. N-[5-(3-Fluoro-benzenesulfonyl)-1H-indazol-3-yl]-4-(4-methyl-piperazin-1-yl)-2-(piperidin-3-ylamino)-benzamide;
28. N-[5-(3,5-Difluoro-benzenesulfonyl)-1H-indazol-3-yl]-4-(4-methyl-piperazin-1-yl)-2-(piperidin-3-ylamino)-benzamide;
29. N-[5-(3-Fluoro-benzenesulfonyl)-1H-indazol-3-yl]-4-(4-methyl-piperazin-1-yl)-2-(tetrahydro-thiopyran-4-ylamino)-benzamide;
30. N-[5-(3,5-Difluoro-benzenesulfonyl)-1H-indazol-3-yl]-4-(4-methyl-piperazin-1-yl)-2-(tetrahydro-thiopyran-4-ylamino)-benzamide;
31. N-[5-(3-Fluoro-benzenesulfonyl)-1H-indazol-3-yl]-2-[(furan-2-ylmethyl)-amino]-4-(4-methyl-piperazin-1-yl)-benzamide;
32. N-[5-(3,5-Difluoro-benzenesulfonyl)-1H-indazol-3-yl]-2-[(furan-2-ylmethyl)-amino]-4-(4-methyl-piperazin-1-yl)-benzamide;
33. 1H-Pyrrole-2-carboxylic acid [2-(5-benzenesulfonyl-1H-indazol-3-ylcarbamoyl)-5-(4-methyl-piperazin-1-yl)-phenyl]-amide;
34. 1H-Pyrrole-2-carboxylic acid [2-[5-(3-fluoro-benzenesulfonyl)-1H-indazol-3-ylcarbamoyl]-5-(4-methyl-piperazin-1-yl)-phenyl]-amide;
35. 1H-Pyrrole-2-carboxylic acid [2-[5-(3,5-difluoro-benzenesulfonyl)-1H-indazol-3-ylcarbamoyl]-5-(4-methyl-piperazin-1-yl)-phenyl]-amide;
36. (S)-Tetrahydro-furan-2-carboxylic acid [2-(5-benzenesulfonyl-1H-indazol-3-ylcarbamoyl)-5-(4-methyl-piperazin-1-yl)-phenyl]-amide;
37. (S)-Tetrahydro-furan-2-carboxylic acid [2-[5-(3-fluoro-benzenesulfonyl)-1H-indazol-3-ylcarbamoyl]-5-(4-methyl-piperazin-1-yl)-phenyl]-amide;
38. (S)-Tetrahydro-furan-2-carboxylic acid [2-[5-(3,5-difluoro-benzenesulfonyl)-1H-indazol-3-ylcarbamoyl]-5-(4-methyl-piperazin-1-yl)-phenyl]-amide;
39. 1H-Pyrrole-3-carboxylic acid [2-(5-benzenesulfonyl-1H-indazol-3-ylcarbamoyl)-5-(4-methyl-piperazin-1-yl)-phenyl]-amide;
40. 1H-Pyrrole-3-carboxylic acid [2-[5-(3-fluoro-benzenesulfonyl)-1H-indazol-3-ylcarbamoyl]-5-(4-methyl-piperazin-1-yl)-phenyl]-amide;
41. 1H-Pyrrole-3-carboxylic acid [2-[5-(3,5-difluoro-benzenesulfonyl)-1H-indazol-3-ylcarbamoyl]-5-(4-methyl-piperazin-1-yl)-phenyl]-amide;
42. N-[5-(3-Fluoro-benzenesulfonyl)-1H-indazol-3-yl]-2-isobutyrylamino-4-(4-methyl-piperazin-1-yl)-benzamide;
43. N-[5-(3,5-Difluoro-benzenesulfonyl)-1H-indazol-3-yl]-2-isobutyrylamino-4-(4-methyl-piperazin-1-yl)-benzamide;
44. 2-(Cyclobutanecarbonyl-amino)-N-[5-(3-fluoro-benzenesulfonyl)-1H-indazol-3-yl]-4-(4-methyl-piperazin-1-yl)-benzamide;
45. 2-(Cyclobutanecarbonyl-amino)-N-[5-(3,5-difluoro-benzenesulfonyl)-1H-indazol-3-yl]-4-(4-methyl-piperazin-1-yl)-benzamide;
46. 2-(2-Amino-acetylamino)-N-[5-(3-fluoro-benzenesulfonyl)-1H-indazol-3-yl]-4-(4-methyl-piperazin-1-yl)-benzamide;
47. 2-(2-Amino-acetylamino)-N-[5-(3,5-difluoro-benzenesulfonyl)-1H-indazol-3-yl]-4-(4-methyl-piperazin-1-yl)-benzamide;
48. N-[5-(3-Fluoro-benzenesulfonyl)-1H-indazol-3-yl]-2-(2-methylamino-acetylamino)-4-(4-methyl-piperazin-1-yl)-benzamide;
49. N-[5-(3,5-Difluoro-benzenesulfonyl)-1H-indazol-3-yl]-2-(2-methylamino-acetylamino)-4-(4-methyl-piperazin-1-yl)-benzamide;
50. 2-(2-Dimethylamino-acetylamino)-N-[5-(3-fluoro-benzenesulfonyl)-1H-indazol-3-yl]-4-(4-methyl-piperazin-1-yl)-benzamide;
51. N-[5-(3,5-Difluoro-benzenesulfonyl)-1H-indazol-3-yl]-2-(2-dimethylamino-acetylamino)-4-(4-methyl-piperazin-1-yl)-benzamide;
52. 2-((S)-2-Amino-propionylamino)-N-[5-(3-fluoro-benzenesulfonyl)-1H-indazol-3-yl]-4-(4-methyl-piperazin-1-yl)-benzamide;
53. 2-((S)-2-Amino-propionylamino)-N-[5-(3,5-difluoro-benzenesulfonyl)-1H-indazol-3-yl]-4-(4-methyl-piperazin-1-yl)-benzamide;
54. (S)-Pyrrolidine-2-carboxylic acid [2-[5-(3-fluoro-benzenesulfonyl)-1H-indazol-3-ylcarbamoyl]-5-(4-methyl-piperazin-1-yl)-phenyl]-amide;
55. (S)-Pyrrolidine-2-carboxylic acid [2-[5-(3,5-difluoro-benzenesulfonyl)-1H-indazol-3-ylcarbamoyl]-5-(4-methyl-piperazin-1-yl)-phenyl]-amide;
56. Piperidine-2-carboxylic acid [2-[5-(3-fluoro-benzenesulfonyl)-1H-indazol-3-ylcarbamoyl]-5-(4-methyl-piperazin-1-yl)-phenyl]-amide;
57. Piperidine-2-carboxylic acid [2-[5-(3,5-difluoro-benzenesulfonyl)-1H-indazol-3-ylcarbamoyl]-5-(4-methyl-piperazin-1-yl)-phenyl]-amide;
58. Piperidine-3-carboxylic acid [2-[5-(3-fluoro-benzenesulfonyl)-1H-indazol-3-ylcarbamoyl]-5-(4-methyl-piperazin-1-yl)-phenyl]-amide;

59. Piperidine-3-carboxylic acid [2-[5-(3,5-difluoro-benzenesulfonyl)-1H-indazol-3-ylcarbamoyl]-5-(4-methyl-piperazin-1-yl)-phenyl]-amide;
60. Piperidine-4-carboxylic acid [2-[5-(3-fluoro-benzenesulfonyl)-1H-indazol-3-ylcarbamoyl]-5-(4-methyl-piperazin-1-yl)-phenyl]-amide;
61. Piperidine-4-carboxylic acid [2-[5-(3,5-difluoro-benzenesulfonyl)-1H-indazol-3-ylcarbamoyl]-5-(4-methyl-piperazin-1-yl)-phenyl]-amide;
62. (R)-Tetrahydro-furan-2-carboxylic acid [2-[5-(3,5-difluoro-benzenesulfonyl)-1H-indazol-3-ylcarbamoyl]-5-(4-methyl-piperazin-1-yl)-phenyl]-amide;
63. Tetrahydro-furan-3-carboxylic acid [2-[5-(3,5-difluoro-benzenesulfonyl)-1H-indazol-3-ylcarbamoyl]-5-(4-methyl-piperazin-1-yl)-phenyl]-amide;
64. Tetrahydro-pyran-4-carboxylic acid [2-[5-(3,5-difluoro-benzenesulfonyl)-1H-indazol-3-ylcarbamoyl]-5-(4-methyl-piperazin-1-yl)-phenyl]-amide;
65. Pyridine-2-carboxylic acid [2-(5-benzenesulfonyl-1H-indazol-3-ylcarbamoyl)-5-(4-methyl-piperazin-1-yl)-phenyl]-amide;
66. Pyridine-2-carboxylic acid [2-[5-(3-fluoro-benzenesulfonyl)-1H-indazol-3-ylcarbamoyl]-5-(4-methyl-piperazin-1-yl)-phenyl]-amide;
67. Pyridine-2-carboxylic acid [2-[5-(3,5-difluoro-benzenesulfonyl)-1H-indazol-3-ylcarbamoyl]-5-(4-methyl-piperazin-1-yl)-phenyl]-amide;
68. 3H-Imidazole-4-carboxylic acid [2-(5-benzenesulfonyl-1H-indazol-3-ylcarbamoyl)-5-(4-methyl-piperazin-1-yl)-phenyl]-amide;
69. 3H-Imidazole-4-carboxylic acid [2-[5-(3-fluoro-benzenesulfonyl)-1H-indazol-3-ylcarbamoyl]-5-(4-methyl-piperazin-1-yl)-phenyl]-amide;
70. 3H-Imidazole-4-carboxylic acid [2-[5-(3,5-difluoro-benzenesulfonyl)-1H-indazol-3-ylcarbamoyl]-5-(4-methyl-piperazin-1-yl)-phenyl]-amide;
71. 1-Methyl-1H-pyrrole-2-carboxylic acid [2-(5-benzenesulfonyl-1H-indazol-3-ylcarbamoyl)-5-(4-methyl-piperazin-1-yl)-phenyl]-amide;
72. 1-Methyl-1H-pyrrole-2-carboxylic acid [2-[5-(3-fluoro-benzenesulfonyl)-1H-indazol-3-ylcarbamoyl]-5-(4-methyl-piperazin-1-yl)-phenyl]-amide;
73. 1-Methyl-1H-pyrrole-2-carboxylic acid [2-[5-(3,5-difluoro-benzenesulfonyl)-1H-indazol-3-ylcarbamoyl]-5-(4-methyl-piperazin-1-yl)-phenyl]-amide;
74. Furan-2-carboxylic acid [2-[5-(3-fluoro-benzenesulfonyl)-1H-indazol-3-ylcarbamoyl]-5-(4-methyl-piperazin-1-yl)-phenyl]-amide;
75. Furan-2-carboxylic acid [2-[5-(3,5-difluoro-benzenesulfonyl)-1H-indazol-3-ylcarbamoyl]-5-(4-methyl-piperazin-1-yl)-phenyl]-amide;
76. 5-Methyl-isoxazole-4-carboxylic acid [2-(5-benzenesulfonyl-1H-indazol-3-ylcarbamoyl)-5-(4-methyl-piperazin-1-yl)-phenyl]-amide;
77. 5-Methyl-isoxazole-4-carboxylic acid [2-[5-(3-fluoro-benzenesulfonyl)-1H-indazol-3-ylcarbamoyl]-5-(4-methyl-piperazin-1-yl)-phenyl]-amide;
78. 5-Methyl-isoxazole-4-carboxylic acid [2-[5-(3,5-difluoro-benzenesulfonyl)-1H-indazol-3-ylcarbamoyl]-5-(4-methyl-piperazin-1-yl)-phenyl]-amide;
79. N-(5-Benzenesulfonyl-1H-indazol-3-yl)-2-benzoylamino-4-(4-methyl-piperazin-1-yl)-benzamide;
80. 2-Benzoylamino-N-[5-(3-fluoro-benzenesulfonyl)-1H-indazol-3-yl]-4-(4-methyl-piperazin-1-yl)-benzamide;
81. 2-Benzoylamino-N-[5-(3,5-difluoro-benzenesulfonyl)-1H-indazol-3-yl]-4-(4-methyl-piperazin-1-yl)-benzamide;
82. N-[5-(3-Chloro-benzenesulfonyl)-1H-indazol-3-yl]-4-(4-methyl-piperazin-1-yl)-2-(tetrahydro-pyran-4-ylamino)-benzamide;
83. N-[5-(3-Methoxy-benzenesulfonyl)-1H-indazol-3-yl]-4-(4-methyl-piperazin-1-yl)-2-(tetrahydro-pyran-4-ylamino)-benzamide;
84. N-[5-(3,5-Dichloro-benzenesulfonyl)-1H-indazol-3-yl]-4-(4-methyl-piperazin-1-yl)-2-(tetrahydro-pyran-4-ylamino)-benzamide;
85. N-[5-(3-Fluoro-5-methoxy-benzenesulfonyl)-1H-indazol-3-yl]-4-(4-methyl-piperazin-1-yl)-2-(tetrahydro-pyran-4-ylamino)-benzamide;
86. N-[5-(3-Fluoro-benzenesulfonyl)-1H-indazol-3-yl]-2-(tetrahydro-pyran-4-ylamino)-benzamide;
87. N-[5-(3,5-Difluoro-benzenesulfonyl)-1H-indazol-3-yl]-2-(tetrahydro-pyran-4-ylamino)-benzamide;
88. 4-Fluoro-N-[5-(3-fluoro-benzenesulfonyl)-1H-indazol-3-yl]-2-(tetrahydro-pyran-4-ylamino)-benzamide;
89. N-[5-(3,5-Difluoro-benzenesulfonyl)-1H-indazol-3-yl]-4-fluoro-2-(tetrahydro-pyran-4-ylamino)-benzamide;
90. N-[5-(3-Fluoro-benzenesulfonyl)-1H-indazol-3-yl]-4-methoxy-2-(tetrahydro-pyran-4-ylamino)-benzamide;
91. N-[5-(3,5-Difluoro-benzenesulfonyl)-1H-indazol-3-yl]-4-methoxy-2-(tetrahydro-pyran-4-ylamino)-benzamide;
92. 4-Dimethylamino-N-[5-(3-fluoro-benzenesulfonyl)-1H-indazol-3-yl]-2-(tetrahydro-pyran-4-ylamino)-benzamide;
93. N-[5-(3,5-Difluoro-benzenesulfonyl)-1H-indazol-3-yl]-4-dimethylamino-2-(tetrahydro-pyran-4-ylamino)-benzamide;
94. N-[5-(3-Fluoro-benzenesulfonyl)-1H-indazol-3-yl]-4-morpholin-4-yl-2-(tetrahydro-pyran-4-ylamino)-benzamide;
95. N-[5-(3,5-Difluoro-benzenesulfonyl)-1H-indazol-3-yl]-4-morpholin-4-yl-2-(tetrahydro-pyran-4-ylamino)-benzamide;
96. N-[5-(3-Fluoro-benzenesulfonyl)-1H-indazol-3-yl]-4-piperazin-1-yl-2-(tetrahydro-pyran-4-ylamino)-benzamide;
97. N-[5-(3,5-Difluoro-benzenesulfonyl)-1H-indazol-3-yl]-4-piperazin-1-yl-2-(tetrahydro-pyran-4-ylamino)-benzamide;
98. 4-(4-Ethyl-piperazin-1-yl)-N-[5-(3-fluoro-benzenesulfonyl)-1H-indazol-3-yl]-2-(tetrahydro-pyran-4-ylamino)-benzamide;
99. N-[5-(3,5-Difluoro-benzenesulfonyl)-1H-indazol-3-yl]-4-(4-ethyl-piperazin-1-yl)-2-(tetrahydro-pyran-4-ylamino)-benzamide;
100. N-[5-(3-Fluoro-benzenesulfonyl)-1H-indazol-3-yl]-4-(4-propyl-piperazin-1-yl)-2-(tetrahydro-pyran-4-ylamino)-benzamide;
101. N-[5-(3,5-Difluoro-benzenesulfonyl)-1H-indazol-3-yl]-4-(4-propyl-piperazin-1-yl)-2-(tetrahydro-pyran-4-ylamino)-benzamide;
102. N-[5-(3-Fluoro-benzenesulfonyl)-1H-indazol-3-yl]-4-(4-isopropyl-piperazin-1-yl)-2-(tetrahydro-pyran-4-ylamino)-benzamide;
103. N-[5-(3,5-Difluoro-benzenesulfonyl)-1H-indazol-3-yl]-4-(4-isopropyl-piperazin-1-yl)-2-(tetrahydro-pyran-4-ylamino)-benzamide;
104. N-[5-(3-Fluoro-benzenesulfonyl)-1H-indazol-3-yl]-4-(4-methyl-[1,4]diazepan-1-yl)-2-(tetrahydro-pyran-4-ylamino)-benzamide;
105. N-[5-(3,5-Difluoro-benzenesulfonyl)-1H-indazol-3-yl]-4-(4-methyl-[1,4]diazepan-1-yl)-2-(tetrahydro-pyran-4-ylamino)-benzamide;

106. 4-(4-Ethyl-[1,4]diazepan-1-yl)-N-[5-(3-fluoro-benzenesulfonyl)-1H-indazol-3-yl]-2-(tetrahydro-pyran-4-ylamino)-benzamide;
107. N-[5-(3,5-Difluoro-benzenesulfonyl)-1H-indazol-3-yl]-4-(4-ethyl-[1,4]diazepan-1-yl)-2-(tetrahydro-pyran-4-ylamino)-benzamide;
108. 4-(2-Dimethylamino-ethoxy)-N-[5-(3-fluoro-benzenesulfonyl)-1H-indazol-3-yl]-2-(tetrahydro-pyran-4-ylamino)-benzamide;
109. N-[5-(3,5-Difluoro-benzenesulfonyl)-1H-indazol-3-yl]-4-(2-dimethylamino-ethoxy)-2-(tetrahydro-pyran-4-ylamino)-benzamide;
110. N-[5-(3-Fluoro-benzenesulfonyl)-1H-indazol-3-yl]-4-(2-pyrrolidin-1-yl-ethoxy)-2-(tetrahydro-pyran-4-ylamino)-benzamide;
111. N-[5-(3,5-Difluoro-benzenesulfonyl)-1H-indazol-3-yl]-4-(2-pyrrolidin-1-yl-ethoxy)-2-(tetrahydro-pyran-4-ylamino)-benzamide;
112. N-[5-(3-Fluoro-benzenesulfonyl)-1H-indazol-3-yl]-4-(1-methyl-piperidin-4-yloxy)-2-(tetrahydro-pyran-4-ylamino)-benzamide;
113. N-[5-(3,5-Difluoro-benzenesulfonyl)-1H-indazol-3-yl]-4-(1-methyl-piperidin-4-yloxy)-2-(tetrahydro-pyran-4-ylamino)-benzamide;
114. 4-Dimethylaminomethyl-N-[5-(3-fluoro-benzenesulfonyl)-1H-indazol-3-yl]-2-(tetrahydro-pyran-4-ylamino)-benzamide;
115. N-[5-(3,5-Difluoro-benzenesulfonyl)-1H-indazol-3-yl]-4-dimethylaminomethyl-2-(tetrahydro-pyran-4-ylamino)-benzamide;
116. N-[5-(3-Fluoro-benzenesulfonyl)-1H-indazol-3-yl]-4-pyrrolidin-1-ylmethyl-2-(tetrahydro-pyran-4-ylamino)-benzamide;
117. N-[5-(3,5-Difluoro-benzenesulfonyl)-1H-indazol-3-yl]-4-pyrrolidin-1-ylmethyl-2-(tetrahydro-pyran-4-ylamino)-benzamide;
118. N-[5-(3-Fluoro-benzenesulfonyl)-1H-indazol-3-yl]-4-piperidin-1-ylmethyl-2-(tetrahydro-pyran-4-ylamino)-benzamide;
119. N-[5-(3,5-Difluoro-benzenesulfonyl)-1H-indazol-3-yl]-4-piperidin-1-ylmethyl-2-(tetrahydro-pyran-4-ylamino)-benzamide;
120. N-[5-(3-Fluoro-benzenesulfonyl)-1H-indazol-3-yl]-4-morpholin-4-ylmethyl-2-(tetrahydro-pyran-4-ylamino)-benzamide;
121. N-[5-(3,5-Difluoro-benzenesulfonyl)-1H-indazol-3-yl]-4-morpholin-4-ylmethyl-2-(tetrahydro-pyran-4-ylamino)-benzamide;
122. N-[5-(3-Fluoro-benzenesulfonyl)-1H-indazol-3-yl]-4-(1-methyl-piperidin-4-ylamino)-2-(tetrahydro-pyran-4-ylamino)-benzamide;
123. N-[5-(3,5-Difluoro-benzenesulfonyl)-1H-indazol-3-yl]-4-(1-methyl-piperidin-4-ylamino)-2-(tetrahydro-pyran-4-ylamino)-benzamide;
124. N-[5-(3-Fluoro-benzenesulfonyl)-1H-indazol-3-yl]-2,4-bis-(tetrahydro-pyran-4-ylamino)-benzamide;
125. N-[5-(3,5-Difluoro-benzenesulfonyl)-1H-indazol-3-yl]-2,4-bis-(tetrahydro-pyran-4-ylamino)-benzamide;
126. 4-(2-Dimethylamino-1-methyl-ethylamino)-N-[5-(3-fluoro-benzenesulfonyl)-1H-indazol-3-yl]-2-(tetrahydro-pyran-4-ylamino)-benzamide;
127. N-[5-(3,5-Difluoro-benzenesulfonyl)-1H-indazol-3-yl]-4-(2-dimethylamino-1-methyl-ethylamino)-2-(tetrahydro-pyran-4-ylamino)-benzamide;
128. 4-(2-Diethylamino-1-methyl-ethylamino)-N-[5-(3-fluoro-benzenesulfonyl)-1H-indazol-3-yl]-2-(tetrahydro-pyran-4-ylamino)-benzamide;
129. 4-(2-Diethylamino-1-methyl-ethylamino)-N-[5-(3,5-difluoro-benzenesulfonyl)-1H-indazol-3-yl]-2-(tetrahydro-pyran-4-ylamino)-benzamide;
130. 4-(2-Dimethylamino-ethylamino)-N-[5-(3-fluoro-benzenesulfonyl)-1H-indazol-3-yl]-2-(tetrahydro-pyran-4-ylamino)-benzamide;
131. N-[5-(3,5-Difluoro-benzenesulfonyl)-1H-indazol-3-yl]-4-(2-dimethylamino-ethylamino)-2-(tetrahydro-pyran-4-ylamino)-benzamide;
132. 4-[(2-Dimethylamino-ethyl)-methyl-amino]-N-[5-(3-fluoro-benzenesulfonyl)-1H-indazol-3-yl]-2-(tetrahydro-pyran-4-ylamino)-benzamide;
133. N-[5-(3,5-Difluoro-benzenesulfonyl)-1H-indazol-3-yl]-4-[(2-dimethylamino-ethyl)-methyl-amino]-2-(tetrahydro-pyran-4-ylamino)-benzamide;
134. N-[5-(3-Fluoro-benzenesulfonyl)-1H-indazol-3-yl]-4-{[2-(isopropyl-methyl-amino)-ethyl]-methyl-amino}-2-(tetrahydro-pyran-4-ylamino)-benzamide;
135. N-[5-(3,5-Difluoro-benzenesulfonyl)-1H-indazol-3-yl]-4-{[2-(isopropyl-methyl-amino)-ethyl]-methyl-amino}-2-(tetrahydro-pyran-4-ylamino)-benzamide;
136. N-[5-(3-Fluoro-benzenesulfonyl)-1H-indazol-3-yl]-4-[methyl-(2-piperidin-1-yl-ethyl)-amino]-2-(tetrahydro-pyran-4-ylamino)-benzamide;
137. N-[5-(3,5-Difluoro-benzenesulfonyl)-1H-indazol-3-yl]-4-[methyl-(2-piperidin-1-yl-ethyl)-amino]-2-(tetrahydro-pyran-4-ylamino)-benzamide;
138. N-[5-(3-Fluoro-benzenesulfonyl)-1H-indazol-3-yl]-4-[methyl-(2-morpholin-4-yl-ethyl)-amino]-2-(tetrahydro-pyran-4-ylamino)-benzamide;
139. N-[5-(3,5-Difluoro-benzenesulfonyl)-1H-indazol-3-yl]-4-[methyl-(2-morpholin-4-yl-ethyl)-amino]-2-(tetrahydro-pyran-4-ylamino)-benzamide;
140. 4-[(2-Dimethylamino-ethyl)-ethyl-amino]-N-[5-(3-fluoro-benzenesulfonyl)-1H-indazol-3-yl]-2-(tetrahydro-pyran-4-ylamino)-benzamide;
141. N-[5-(3,5-Difluoro-benzenesulfonyl)-1H-indazol-3-yl]-4-[(2-dimethylamino-ethyl)-ethyl-amino]-2-(tetrahydro-pyran-4-ylamino)-benzamide;
142. 4-[(3-Dimethylamino-propyl)-methyl-amino]-N-[5-(3-fluoro-benzenesulfonyl)-1H-indazol-3-yl]-2-(tetrahydro-pyran-4-ylamino)-benzamide;
143. N-[5-(3,5-Difluoro-benzenesulfonyl)-1H-indazol-3-yl]-4-[(3-dimethylamino-propyl)-methyl-amino]-2-(tetrahydro-pyran-4-ylamino)-benzamide;
144. 4-(4-Dimethylamino-piperidin-1-yl)-N-[5-(3-fluoro-benzenesulfonyl)-1H-indazol-3-yl]-2-(tetrahydro-pyran-4-ylamino)-benzamide;
145. N-[5-(3,5-Difluoro-benzenesulfonyl)-1H-indazol-3-yl]-4-(4-dimethylamino-piperidin-1-yl)-2-(tetrahydro-pyran-4-ylamino)-benzamide;
146. N-[5-(3-Fluoro-benzenesulfonyl)-1H-indazol-3-yl]-4-(4-pyrrolidin-1-yl-piperidin-1-yl)-2-(tetrahydro-pyran-4-ylamino)-benzamide;
147. N-[5-(3,5-Difluoro-benzenesulfonyl)-1H-indazol-3-yl]-4-(4-pyrrolidin-1-yl-piperidin-1-yl)-2-(tetrahydro-pyran-4-ylamino)-benzamide;
148. N-[5-(3-Fluoro-benzenesulfonyl)-1H-indazol-3-yl]-4-[methyl-(1-methyl-pyrrolidin-3-yl)-amino]-2-(tetrahydro-pyran-4-ylamino)-benzamide;
149. N-[5-(3,5-Difluoro-benzenesulfonyl)-1H-indazol-3-yl]-4-[methyl-(1-methyl-pyrrolidin-3-yl)-amino]-2-(tetrahydro-pyran-4-ylamino)-benzamide;
150. N-[5-(3,5-Difluoro-benzenesulfonyl)-1H-indazol-3-yl]-2-(2-methoxy-ethylamino)-4-(4-methyl-piperazin-1-yl)-benzamide;

151. N-[5-(3-Fluoro-benzenesulfonyl)-1H-indazol-3-yl]-2-(2-methoxy-ethylamino)-4-(4-methyl-piperazin-1-yl)-benzamide;
152. N-[5-(3,5-Difluoro-benzenesulfonyl)-1H-indazol-3-yl]-4-[(2-dimethylamino-ethyl)-methyl-amino]-2-(2-methoxy-ethylamino)-benzamide;
153. 4-[(2-Dimethylamino-ethyl)-methyl-amino]-N-[5-(3-fluoro-benzenesulfonyl)-1H-indazol-3-yl]-2-(2-methoxy-ethylamino)-benzamide;
154. N-[5-(3,5-Difluoro-benzenesulfonyl)-1H-indazol-3-yl]-4-[(3-dimethylamino-propyl)-methyl-amino]-2-(2-methoxy-ethylamino)-benzamide;
155. 4-[(3-Dimethylamino-propyl)-methyl-amino]-N-[5-(3-fluoro-benzenesulfonyl)-1H-indazol-3-yl]-2-(2-methoxy-ethylamino)-benzamide;
156. N-[5-(3,5-Difluoro-benzenesulfonyl)-1H-indazol-3-yl]-4-[(2-dimethylamino-1-methyl-ethyl)-methyl-amino]-2-(2-methoxy-ethylamino)-benzamide;
157. 4-[(2-Dimethylamino-1-methyl-ethyl)-methyl-amino]-N-[5-(3-fluoro-benzenesulfonyl)-1H-indazol-3-yl]-2-(2-methoxy-ethylamino)-benzamide;
158. N-[5-(3,5-Difluoro-benzenesulfonyl)-1H-indazol-3-yl]-2-(2-methoxy-1-methyl-ethylamino)-4-(4-methyl-piperazin-1-yl)-benzamide;
159. N-[5-(3-Fluoro-benzenesulfonyl)-1H-indazol-3-yl]-2-(2-methoxy-1-methyl-ethylamino)-4-(4-methyl-piperazin-1-yl)-benzamide;
160. N-[5-(3,5-Difluoro-benzenesulfonyl)-1H-indazol-3-yl]-4-[(2-dimethylamino-ethyl)-methyl-amino]-2-(2-methoxy-1-methyl-ethylamino)-benzamide;
161. 4-[(2-Dimethylamino-ethyl)-methyl-amino]-N-[5-(3-fluoro-benzenesulfonyl)-1H-indazol-3-yl]-2-(2-methoxy-1-methyl-ethylamino)-benzamide;
162. N-[5-(3,5-Difluoro-benzenesulfonyl)-1H-indazol-3-yl]-4-[(3-dimethylamino-propyl)-methyl-amino]-2-(2-methoxy-1-methyl-ethylamino)-benzamide;
163. 4-[(3-Dimethylamino-propyl)-methyl-amino]-N-[5-(3-fluoro-benzenesulfonyl)-1H-indazol-3-yl]-2-(2-methoxy-1-methyl-ethylamino)-benzamide;
164. N-[5-(3,5-Difluoro-benzenesulfonyl)-1H-indazol-3-yl]-4-[(2-dimethylamino-1-methyl-ethyl)-methyl-amino]-2-(2-methoxy-1-methyl-ethylamino)-benzamide;
165. 4-[(2-Dimethylamino-1-methyl-ethyl)-methyl-amino]-N-[5-(3-fluoro-benzenesulfonyl)-1H-indazol-3-yl]-2-(2-methoxy-1-methyl-ethylamino)-benzamide;
166. N-[5-(3,5-Difluoro-benzenesulfonyl)-1H-indazol-3-yl]-4-dimethylaminomethyl-2-(2-methoxy-1-methyl-ethylamino)-benzamide;
167. N-[5-(3,5-Difluoro-benzenesulfonyl)-1H-indazol-3-yl]-2-((S)-2-methoxy-1-methyl-ethylamino)-4-(4-methyl-piperazin-1-yl)-benzamide;
168. N-[5-(3-Fluoro-benzenesulfonyl)-1H-indazol-3-yl]-2-((S)-2-methoxy-1-methyl-ethylamino)-4-(4-methyl-piperazin-1-yl)-benzamide;
169. N-[5-(3,5-Difluoro-benzenesulfonyl)-1H-indazol-3-yl]-4-[(2-dimethylamino-ethyl)-methyl-amino]-2-((S)-2-methoxy-1-methyl-ethylamino)-benzamide;
170. 4-[(2-Dimethylamino-ethyl)-methyl-amino]-N-[5-(3-fluoro-benzenesulfonyl)-1H-indazol-3-yl]-2-((S)-2-methoxy-1-methyl-ethylamino)-benzamide;
171. N-[5-(3,5-Difluoro-benzenesulfonyl)-1H-indazol-3-yl]-4-[(3-dimethylamino-propyl)-methyl-amino]-2-((S)-2-methoxy-1-methyl-ethylamino)-benzamide;
172. 4-[(3-Dimethylamino-propyl)-methyl-amino]-N-[5-(3-fluoro-benzenesulfonyl)-1H-indazol-3-yl]-2-((S)-2-methoxy-1-methyl-ethylamino)-benzamide;
173. N-[5-(3,5-Difluoro-benzenesulfonyl)-1H-indazol-3-yl]-4-[(2-dimethylamino-1-methyl-ethyl)-methyl-amino]-2-((S)-2-methoxy-1-methyl-ethylamino)-benzamide;
174. 4-[(2-Dimethylamino-1-methyl-ethyl)-methyl-amino]-N-[5-(3-fluoro-benzenesulfonyl)-1H-indazol-3-yl]-2-((S)-2-methoxy-1-methyl-ethylamino)-benzamide;
175. N-[5-(3,5-Difluoro-benzenesulfonyl)-1H-indazol-3-yl]-2-((R)-2-methoxy-1-methyl-ethylamino)-4-(4-methyl-piperazin-1-yl)-benzamide;
176. N-[5-(3-Fluoro-benzenesulfonyl)-1H-indazol-3-yl]-2-((R)-2-methoxy-1-methyl-ethylamino)-4-(4-methyl-piperazin-1-yl)-benzamide;
177. N-[5-(3,5-Difluoro-benzenesulfonyl)-1H-indazol-3-yl]-4-[(2-dimethylamino-ethyl)-methyl-amino]-2-((R)-2-methoxy-1-methyl-ethylamino)-benzamide;
178. 4-[(2-Dimethylamino-ethyl)-methyl-amino]-N-[5-(3-fluoro-benzenesulfonyl)-1H-indazol-3-yl]-2-((R)-2-methoxy-1-methyl-ethylamino)-benzamide;
179. N-[5-(3,5-Difluoro-benzenesulfonyl)-1H-indazol-3-yl]-4-[(3-dimethylamino-propyl)-methyl-amino]-2-((R)-2-methoxy-1-methyl-ethylamino)-benzamide;
180. 4-[(3-Dimethylamino-propyl)-methyl-amino]-N-[5-(3-fluoro-benzenesulfonyl)-1H-indazol-3-yl]-2-((R)-2-methoxy-1-methyl-ethylamino)-benzamide;
181. N-[5-(3,5-Difluoro-benzenesulfonyl)-1H-indazol-3-yl]-4-[(2-dimethylamino-1-methyl-ethyl)-methyl-amino]-2-((R)-2-methoxy-1-methyl-ethylamino)-benzamide;
182. 4-[(2-Dimethylamino-1-methyl-ethyl)-methyl-amino]-N-[5-(3-fluoro-benzenesulfonyl)-1H-indazol-3-yl]-2-((R)-2-methoxy-1-methyl-ethylamino)-benzamide;
183. N-[5-(3,5-Difluoro-benzenesulfonyl)-1H-indazol-3-yl]-2-(2-methoxy-1-methoxymethyl-ethylamino)-4-(4-methyl-piperazin-1-yl)-benzamide;
184. N-[5-(3-Fluoro-benzenesulfonyl)-1H-indazol-3-yl]-2-(2-methoxy-1-methoxymethyl-ethylamino)-4-(4-methyl-piperazin-1-yl)-benzamide;
185. N-[5-(3,5-Difluoro-benzenesulfonyl)-1H-indazol-3-yl]-4-[(2-dimethylamino-ethyl)-methyl-amino]-2-(2-methoxy-1-methoxymethyl-ethylamino)-benzamide;
186. 4-[(2-Dimethylamino-ethyl)-methyl-amino]-N-[5-(3-fluoro-benzenesulfonyl)-1H-indazol-3-yl]-2-(2-methoxy-1-methoxymethyl-ethylamino)-benzamide;
187. N-[5-(3,5-Difluoro-benzenesulfonyl)-1H-indazol-3-yl]-4-[(3-dimethylamino-propyl)-methyl-amino]-2-(2-methoxy-1-methoxymethyl-ethylamino)-benzamide;
188. 4-[(3-Dimethylamino-propyl)-methyl-amino]-N-[5-(3-fluoro-benzenesulfonyl)-1H-indazol-3-yl]-2-(2-methoxy-1-methoxymethyl-ethylamino)-benzamide;
189. N-[5-(3,5-Difluoro-benzenesulfonyl)-1H-indazol-3-yl]-4-[(2-dimethylamino-1-methyl-ethyl)-methyl-amino]-2-(2-methoxy-1-methoxymethyl-ethylamino)-benzamide;
190. 4-[(2-Dimethylamino-1-methyl-ethyl)-methyl-amino]-N-[5-(3-fluoro-benzenesulfonyl)-1H-indazol-3-yl]-2-(2-methoxy-1-methoxymethyl-ethylamino)-benzamide;
191. N-[5-(3-Fluoro-benzenesulfonyl)-1H-indazol-3-yl]-2-(2-methoxy-1,1-dimethyl-ethylamino)-4-(4-methyl-piperazin-1-yl)-benzamide;
192. N-[5-(3,5-Difluoro-benzenesulfonyl)-1H-indazol-3-yl]-2-(2-methoxy-1,1-dimethyl-ethylamino)-4-(4-methyl-piperazin-1-yl)-benzamide;
193. N-[5-(3-Fluoro-benzenesulfonyl)-1H-indazol-3-yl]-2-((R)-3-methoxy-1-methyl-propylamino)-4-(4-methyl-piperazin-1-yl)-benzamide;

194. N-[5-(3,5-Difluoro-benzenesulfonyl)-1H-indazol-3-yl]-2-((R)-3-methoxy-1-methyl-propylamino)-4-(4-methyl-piperazin-1-yl)-benzamide;
195. N-[5-(3-Fluoro-benzenesulfonyl)-1H-indazol-3-yl]-2-((R)-1-methoxymethyl-propylamino)-4-(4-methyl-piperazin-1-yl)-benzamide;
196. N-[5-(3,5-Difluoro-benzenesulfonyl)-1H-indazol-3-yl]-2-((R)-1-methoxymethyl-propylamino)-4-(4-methyl-piperazin-1-yl)-benzamide;
197. 2-Fluoro-N-[5-(3-fluoro-benzenesulfonyl)-1H-indazol-3-yl]-6-(tetrahydro-pyran-4-ylamino)-benzamide;
198. N-[5-(3,5-Difluoro-benzenesulfonyl)-1H-indazol-3-yl]-2-fluoro-6-(tetrahydro-pyran-4-ylamino)-benzamide;
199. 2-Fluoro-N-[5-(3-fluoro-benzenesulfonyl)-1H-indazol-3-yl]-4-(4-methyl-piperazin-1-yl)-6-(tetrahydro-pyran-4-ylamino)-benzamide;
200. N-[5-(3,5-Difluoro-benzenesulfonyl)-1H-indazol-3-yl]-2-fluoro-4-(4-methyl-piperazin-1-yl)-6-(tetrahydro-pyran-4-ylamino)-benzamide;
201. N-[5-(3-Fluoro-benzenesulfonyl)-1H-indazol-3-yl]-3-(tetrahydro-pyran-4-ylamino)-isonicotinamide;
202. N-[5-(3,5-Difluoro-benzenesulfonyl)-1H-indazol-3-yl]-3-(tetrahydro-pyran-4-ylamino)-isonicotinamide;
203. N-[5-(3-Fluoro-benzenesulfonyl)-1H-indazol-3-yl]-3-(2-methoxy-1-methyl-ethylamino)-isonicotinamide;
204. N-[5-(3,5-Difluoro-benzenesulfonyl)-1H-indazol-3-yl]-3-(2-methoxy-1-methyl-ethylamino)-isonicotinamide;
205. N-[5-(3-Fluoro-benzenesulfonyl)-1H-indazol-3-yl]-2-(tetrahydro-pyran-4-ylamino)-nicotinamide;
206. N-[5-(3,5-Difluoro-benzenesulfonyl)-1H-indazol-3-yl]-2-(tetrahydro-pyran-4-ylamino)-nicotinamide;
207. N-[5-(3-Fluoro-benzenesulfonyl)-1H-indazol-3-yl]-6-(4-methyl-piperazin-1-yl)-2-(tetrahydro-pyran-4-ylamino)-nicotinamide;
208. N-[5-(3,5-Difluoro-benzenesulfonyl)-1H-indazol-3-yl]-6-(4-methyl-piperazin-1-yl)-2-(tetrahydro-pyran-4-ylamino)-nicotinamide;
209. N-[5-(3-Fluoro-benzenesulfonyl)-1H-indazol-3-yl]-3-[(1H-pyrrole-2-carbonyl)-amino]-isonicotinamide;
210. N-[5-(3,5-Difluoro-benzenesulfonyl)-1H-indazol-3-yl]-3-[(1H-pyrrole-2-carbonyl)-amino]-isonicotinamide;
211. N-[5-(3-Fluoro-benzenesulfonyl)-1H-indazol-3-yl]-2-[(1H-pyrrole-2-carbonyl)-amino]-nicotinamide;
212. N-[5-(3,5-Difluoro-benzenesulfonyl)-1H-indazol-3-yl]-2-[(1H-pyrrole-2-carbonyl)-amino]-nicotinamide;
213. 3-Amino-N-[5-(3,5-difluoro-benzenesulfonyl)-1H-indazol-3-yl]-isonicotinamide;
214. N-[5-(3,5-Difluoro-benzenesulfonyl)-1H-indazol-3-yl]-4-fluoro-2-nitro-benzamide;
215. 2-Amino-N-[5-(3,5-difluoro-benzenesulfonyl)-1H-indazol-3-yl]-4-[methyl-(2-piperidin-1-yl-ethyl)-amino]-benzamide;
216. N-[5-(3,5-Difluoro-benzenesulfonyl)-1H-indazol-3-yl]-4-[(3-dimethylamino-propyl)-methyl-amino]-2-isobutylamino-benzamide;
217. N-[5-(3,5-difluoro-benzenesulfonyl)-1H-indazol-3-yl]-4-[methyl-(2-piperidin-1-yl-ethyl)-amino]-2-nitro-benzamide;
218. N-[5-(3-Fluoro-benzenesulfonyl)-1H-indazol-3-yl]-4-nitro-2-(tetrahydro-pyran-4-ylamino)-benzamide;
219. N-[5-(3,5-Difluoro-benzenesulfonyl)-1H-indazol-3-yl]-4-(4-pyrrolidin-1-yl-piperidine-1-carbonyl)-benzamide;
220. N-[5-(3,5-Difluoro-benzenesulfonyl)-1H-indazol-3-yl]-4-((R)-2-pyrrolidin-1-ylmethyl-pyrrolidine-1-carbonyl)-benzamide;
221. N-[5-(3,5-Difluoro-benzenesulfonyl)-1H-indazol-3-yl]-4-((S)-2-pyrrolidin-1-ylmethyl-pyrrolidine-1-carbonyl)-benzamide;
222. 1-Piperidin-4-yl-1H-pyrazole-4-carboxylic acid [5-(3,5-difluoro-benzenesulfonyl)-1H-indazol-3-yl]-amide;
223. N-[5-(3,5-Difluoro-benzenesulfonyl)-1H-indazol-3-yl]-2-(2-fluoro-ethylamino)-4-(4-methyl-piperazin-1-yl)-benzamide;
224. N-[5-(3-Fluoro-benzenesulfonyl)-1H-indazol-3-yl]-2-(2-fluoro-ethylamino)-4-(4-methyl-piperazin-1-yl)-benzamide;
225. N-(5-Benzenesulfonyl-1H-indazol-3-yl)-2-(2-fluoro-ethylamino)-4-(4-methyl-piperazin-1-yl)-benzamide;
226. N-[5-(3,5-Difluoro-benzenesulfonyl)-1H-indazol-3-yl]-2-(2-fluoro-1-fluoromethyl-ethylamino)-4-(4-methyl-piperazin-1-yl)-benzamide;
227. N-[5-(3-Fluoro-benzenesulfonyl)-1H-indazol-3-yl]-2-(2-fluoro-1-fluoromethyl-ethylamino)-4-(4-methyl-piperazin-1-yl)-benzamide and
228. N-(5-Benzenesulfonyl-1H-indazol-3-yl)-2-(2-fluoro-1-fluoromethyl-ethylamino)-4-(4-methyl-piperazin-1-yl)-benzamide.

The present invention also provides a process for the preparation of a compound of formula (I) as defined above, characterized in that the process comprises:

g) hydrolysing a compound of formula (X):

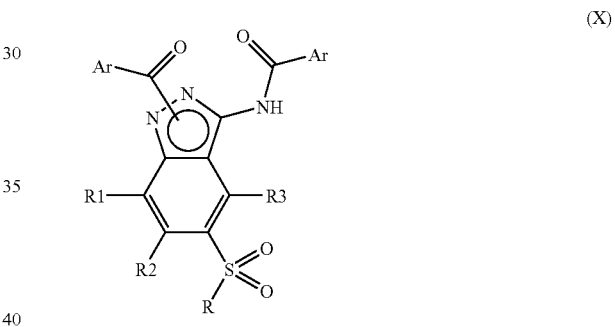

wherein Ar, R1, R2, R3 and R are as defined above, or m) deprotecting a compound of formula (XVII):

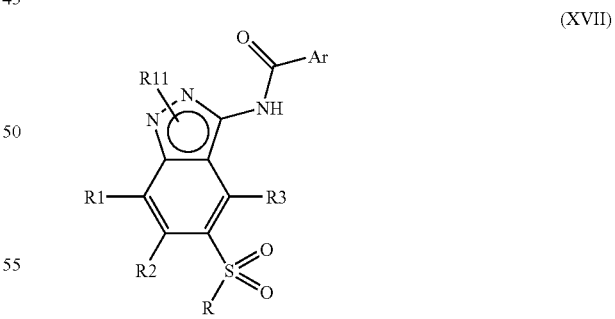

wherein R1, R2, R3, R, and Ar are as defined above, and R11 is benzyl, 4-methoxybenzyl, 2,4-dimethoxybenzyl, or triphenylmethyl;

optionally separating the resulting compound of formula (I) into the single isomers; converting the resulting compound of formula (I) into a different compound of formula (I) and/or into a pharmaceutically acceptable salt if desired.

The present invention further provides a process for the preparation of a compound of formula (I) as defined above, characterized in that the compound of formula (X) as defined above is prepared according to a process which comprises:
a) converting a compound of formula (II):

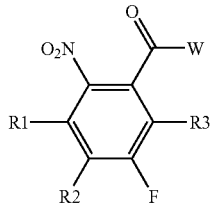

(II)

wherein R1, R2 and R3 are as defined above and W is hydroxy, halogen or a suitable leaving group, into a compound of formula (III):

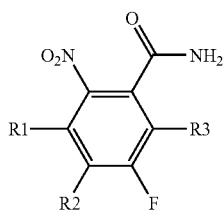

(III)

wherein R1, R2 and R3 are as defined above;
b) reacting the compound of formula (III) as defined above, with a compound of formula (IV):

(IV)

wherein R is as defined above;
c) reducing the resulting compound of formula (V):

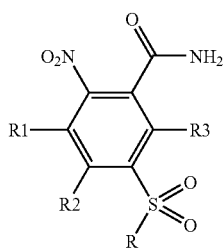

(V)

wherein R1, R2, R3 and R are as defined above;

d) dehydrating the resulting compound of formula (VI):

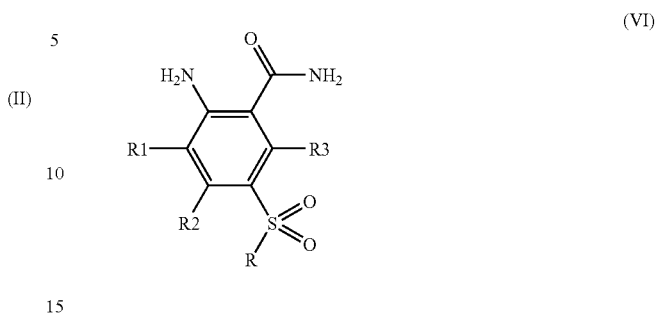

(VI)

wherein R1, R2, R3 and R are as defined above;
e) converting the amino group of the resulting compound of formula (VII):

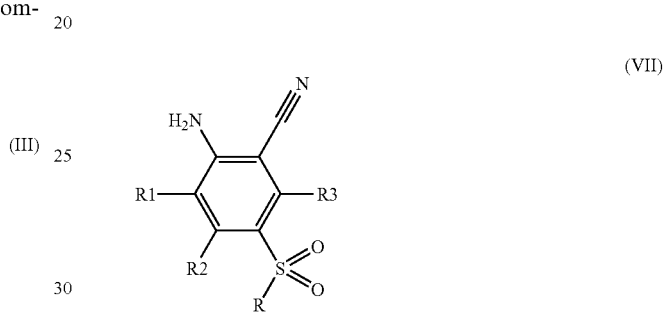

(VII)

wherein R1, R2, R3 and R are as defined above, into a hydrazino group and intramolecularly cyclising it on the cyano group;
f) acylating the resulting compound of formula (VIII):

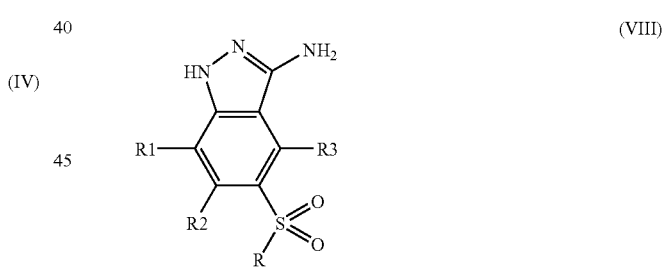

(VIII)

wherein R1, R2, R3 and R are as defined above, with a compound of formula (IX):

$$Ar\underset{O}{\overset{}{\underset{\|}{C}}}W$$

(IX)

wherein Ar and W are as defined above, to give a compound of formula (X) as defined above.

The present invention further provides a process for the preparation of a compound of formula (I) as defined above, characterized in that the compound of formula (VIII) as defined above, is prepared with a process that comprises:

h) reacting the compound of formula (XI):

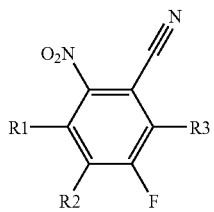

wherein R1, R2, and R3 are as defined above, with a compound of formula (XII):

wherein R is as defined above;
i) oxidizing the resulting compound of formula (XIII):

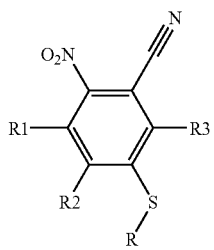

wherein R1, R2, R3 and R are as defined above;
j) reacting the resulting compound of formula (XIV):

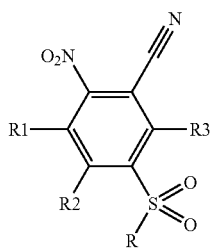

wherein R1, R2, R3 and R are as defined above, with hydrazine to give a compound of formula (VIII) as defined above; or
j') converting the compound of formula (XIV) as defined above into a hydrazine derivative of formula (XXIV):

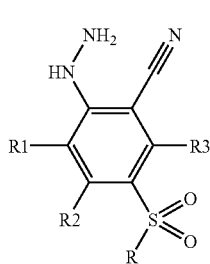

wherein R, R1, R2, R3 are as defined above, and intramolecularly cyclising the compound of formula (XXIV) as defined above, to give a compound of formula (VIII) as defined above.

The present invention further provides a process for the preparation of a compound of formula (I) as defined above, characterized in that the compound of formula (XVII) as defined above, is prepared according to a process which comprises:

k) reacting the compound of formula (XIV) as defined above, with a hydrazine derivative of formula (XV):

R11-NH.NH₂ (XV)

wherein R11 is selected from benzyl, 4-methoxybenzyl, 2,4-dimethoxybenzyl, and triphenylmethyl;
l) acylating the resulting compound of formula (XVI):

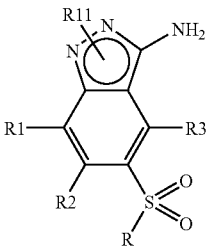

wherein R1, R2, R3, R and R11 are as defined above, with a compound of formula (IX) as defined above, to give a compound of formula (XVII) as defined above; and
optionally converting the resulting compound of formula (XVII) into another compound of formula (XVII).

The present invention further provides an alternative process for the preparation of a compound of formula (I) as defined above, characterized in that compound of formula (XVI) as defined above is prepared according to a process that comprises:

n) protecting the compound of formula (VIII) as defined above, as the phthalimido compound of formula (XVIII):

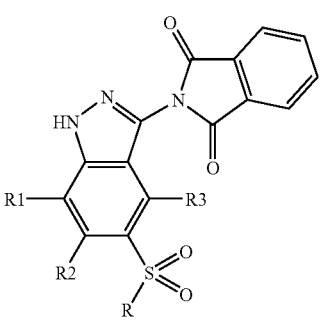

wherein R1, R2, R3 and R are as defined above;
o) alkylating the compound of formula (XVIII) as defined above with a compound of formula (XIX):

R11-Z (XIX)

wherein R11 is as defined above and Z is halogen or a suitable leaving group;

p) deprotecting the resulting compound of formula (XX):

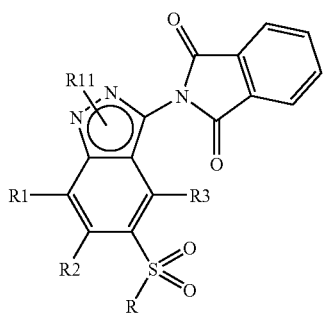

(XX)

wherein R1, R2, R3, R and R11 are as defined above, by removing the phthalimido group to give a compound of formula (XVI) as defined above.

The present invention further provides an alternative process for the preparation of a compound of formula (I) as defined above, characterized in that the compound of formula (XVI) as defined above, is prepared according to a process that comprises:

q) exhaustively trifluoroacetylating the compound of formula (VIII) as defined above; selectively hydrolysing under mild conditions the resulting compound for removing the trifluoroacetyl group on the pyrazole ring nitrogen, to give the compound of formula (XXI):

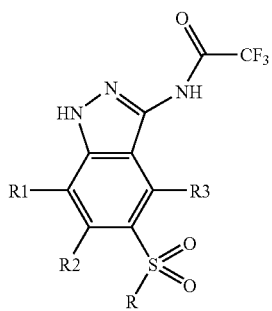

(XXI)

wherein R1, R2, R3 and R are as defined above;
r) protecting the compound of formula (XXI) as defined above, by reaction with a compound of formula (XIX) as defined above;
s) deprotecting the resulting compound of formula (XXII):

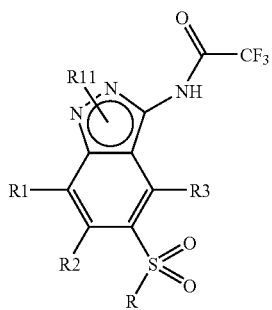

(XXII)

wherein R1, R2, R3, R and R11 are as defined above, by removing the trifluoroacetyl group to give a compound of formula (XVI) as defined above.

It is to be noted that a compound of formula (X), as above defined can be in any one of its isomeric forms a or b:

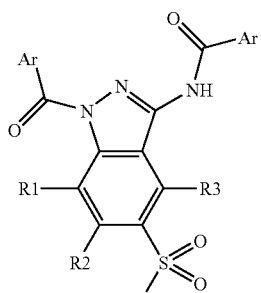

a

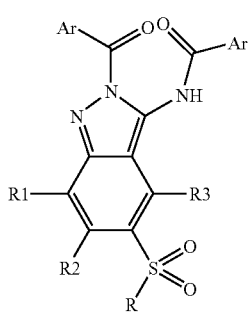

b

Analogously, a compound of formula (XVI), (XVII), (XX) or (XXII), as defined above, can be in any one of its isomeric forms c or d:

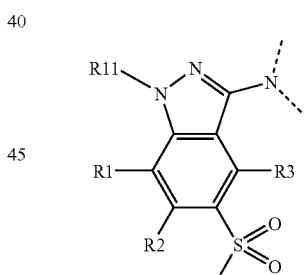

c

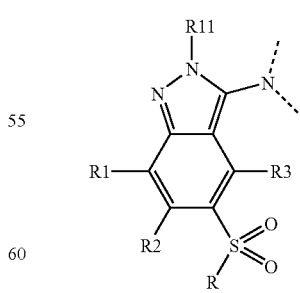

d

As said above, a compound of formula (XVII) may be converted into another compound of formula (XVII), said conversion is carried out by one or more of the following reactions:

1) reducing a compound of formula (XVII) wherein Ar is a substituted aryl and one of the substituents is $NO_2$, for obtaining a compound of formula (XVII) wherein such substituent is $NH_2$;
2) acylating a compound of formula (XVII), wherein Ar is a substituted aryl and one of the substituents is $NH_2$, by reaction with an acylating agent of formula (XXIII)

(XXIII)

wherein R4 and W are as defined above, for obtaining a compound of formula (XVII) wherein such substituent is a NHCOR4 residue, wherein R4 is as defined above;
3) reacting a compound of formula (XVII), wherein Ar is a substituted aryl and one of the substituents is $NH_2$, with a suitable aldehyde or ketone in the presence of a reducing agent, for obtaining a compound of formula (XVII), wherein such substituent is a NR5R6 group, wherein one of the R5 or R6 is hydrogen and the other is an optionally further substituted straight or branched $C_1$-$C_6$ alkyl, $C_3$-$C_6$ cycloalkyl, heterocyclyl, R8R9N—$C_2$-$C_6$ alkyl, R8O—$C_2$-$C_6$ alkyl, wherein R8 and R9 are as defined above;
4) hydrolyzing a compound of formula (XVII), wherein Ar is a substituted aryl and one of the substituents is COR4, wherein R4 is OR7 and R7 is methyl or ethyl, for obtaining a compound of formula (XVII), wherein such substituent COR4 represents COOH;
5) amidating a compound of formula (XVII), wherein Ar is a substituted aryl and one of the substituents is COR4, wherein R4 is OR7 and R7 is hydrogen, with an amine of formula NHR5R6, wherein R5 and R6 are as defined above, for obtaining a compound of formula (XVII), wherein such substituent is CONR5R6, wherein R5 and R6 are as defined above.

As said above, a compound of formula (I) may be converted into another compound of formula (I), said conversion is carried out by one or more of the following reactions:
6) reducing a compound of formula (I) wherein Ar is a substituted aryl and one of the substituents is $NO_2$, for obtaining a compound of formula (I) wherein such substituent is $NH_2$;
7) acylating a compound of formula (I), wherein Ar is a substituted aryl and one of the substituents is $NH_2$, by reaction with an excess of a compound of formula (XXIII)

(XXIII)

wherein R4 and W are defined above, followed by selective deprotection of the acyl group on the pyrazole ring, for obtaining a compound of formula (I) wherein such substituent is a NHCOR4 residue, wherein R4 is as defined above;
8) reacting a compound of formula (I), wherein Ar is a substituted aryl and one of the substituents is $NH_2$, with a suitable aldehyde or ketone in the presence of a reducing agent, for obtaining a compound of formula (I), wherein such substituent is a NR5R6 group, wherein one of the R5 or R6 are defined as in conversion 3).

The synthesis of a compound of formula (I), according to the synthetic processes described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to the step a) of the process, the transformation of a compound of formula (II) into a compound of formula (III) can be accomplished in a variety of ways and experimental conditions, which are widely known in the art for the preparation of primary carboxamides. As an example, a compound of formula (II) can be converted into its corresponding acyl chloride in the presence of thionyl chloride or oxalyl chloride, in a suitable solvent, such as toluene, dichloromethane, chloroform, diethyl ether, tetrahydrofuran, 1,4-dioxane, at a temperature ranging from about −10° C. to reflux and for a period of time varying from about 1 hour to about 96 hours. The acyl chloride can be isolated by evaporation of the solvent and further reacted with 33% ammonium hydroxide solution in a suitable solvent, such as toluene, dichloromethane, chloroform, diethyl ether, tetrahydrofuran, 1,4-dioxane, at a temperature ranging from about −10° C. to reflux and for a period of time varying from about 1 hour to about 96 hours. Alternatively, a compound of formula (II) can be reacted with the ammonium salt of 1-hydroxybenzotriazole, in the presence of a carbodiimide such as dicyclohexyl carbodiimide, diisopropyl carbodiimide, 1-ethyl-3-(3'-dimethylamino)carbodiimide hydrochloric acid salt. Preferably, this reaction is carried out in a suitable solvent such as, for instance, tetrahydrofuran, dichloromethane, toluene, 1,4-dioxane, and in the presence of a proton scavenger such as, for example, triethylamine, N,N-diisopropylethylamine, at a temperature ranging from room temperature to reflux, for a time ranging from about 30 min. to about 96 hours.

According to the step b) of the process, the reaction of a compound of formula (III) with a sulfinic acid of formula (IV) may be carried out in a variety of ways and experimental conditions, which are widely known in the art for nucleophilic aromatic substitution. Preferably, this reaction is carried out in a suitable solvent such as, for instance, toluene, tetrahydrofuran, 1,4-dioxane, dimethyl sulfoxide or acetonitrile, in the presence of a base such as sodium, potassium or cesium carbonate, at a temperature ranging from about −10° C. to reflux and for a period of time varying from about 1 hour to about 96 hours. Phase transfer catalysts may also be added to improve reactivity. Alternatively, the reaction may be performed with a preformed salt of the sulfinic acid of formula (IV) and in this case the addition of the base may be avoided.

According to the step c) of the process, the reduction of a compound of formula (V) into a compound of formula (VI) can be carried out in a variety of ways, according to conventional methods for reducing a nitro to an amino group. Preferably, this reaction is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to the step d) of the process, the dehydration of a compound of formula (VI) to give a cyano derivative of formula (VII) can be carried out by reaction with a dehydrating agent such as, for instance, phosphorus oxychloride, thionyl chloride or trifluoroacetic anhydride at a temperature ranging from 0° C. to reflux and for a period of time varying from 1 hour to about 48 hours. A suitable solvent can optionally be added such as, for instance, diethylether, 1,4-dioxane, dichloromethane, chloroform or acetonitrile.

According to the step e) of the process, the transformation of a compound of formula (VII) into a compound of formula (VIII) can be accomplished in a variety of ways and experimental conditions, which are widely known in the art for the preparation of 3-aminopyrazoles. Preferably, this reaction is carried out by classic diazotation in aqueous solution of the aniline with nitrous acid, which is generated in situ from a nitrite salt and a strong mineral acid such as concentrated hydrochloric acid or concentrated sulfuric acid, at a temperature ranging from 0° C. to room temperature and for a time varying from about 1 hour to about 96 hours. The aryl diazonium salt is then reduced to the corresponding hydrazine derivative with tin(II) chloride which, under basic conditions, spontaneously affords the 3-aminopyrazole ring at a temperature ranging from 0° C. to room temperature and for a time varying from about 1 hour to about 96 hours.

According to the step f) of the process, the reaction between a compound of formula (VIII) and a compound of formula (IX) can be carried out in a variety of ways, according to conventional methods for acylating amino derivatives. As an example, a compound of formula (VIII) may be reacted with an excess of acyl chloride of formula (IX), in which case W represents a chlorine atom. Preferably, this reaction is carried out in a suitable solvent such as, for instance, tetrahydrofuran, dichloromethane, toluene, 1,4-dioxane, and in the presence of a proton scavenger such as, for example, triethylamine, N,N-diisopropylethylamine, pyridine, at a temperature ranging from room temperature to reflux, for a time ranging from about 30 min. to about 96 hours.

It is known to the skilled person that when a compound of formula (IX) carries functional groups that may interfere with the above reaction, such groups have to be protected before carrying out the reaction. In particular, when a compound of formula (IX) is substituted by residues of general formula NR5R6, OR7, SR7, R8R9N—$C_1$-$C_6$ alkyl, or R8O—$C_1$-$C_6$ alkyl wherein R7 or at least one of R5 and R6 or at least one of R8 and R9 represent hydrogen, such groups may be protected as known in the art. Introduction of a nitrogen protecting group may also be required for a compound of formula (IX) that bears residues such as NHCOR4, NHSOR10 or NHSO$_2$R10.

It is also known to the skilled person that such protecting group may be removed just after the reaction of a compound of formula (IX) with a compound of formula (VIII) or at a later stage in the synthetic process.

According to the step g) of the process, a compound of formula (X) is transformed into a compound of formula (I) by selective cleavage of the acyl residue on the pyrazole nitrogen atom. As an example, this reaction may be carried out under basic conditions, for instance in the presence of sodium hydroxide, potassium hydroxide, lithium hydroxide or barium hydroxide, or of a tertiary amine such as triethylamine, or of hydrazine, and in a suitable solvent such as methanol, ethanol, tetrahydrofuran, N,N-dimethylformamide, water and mixtures thereof. Typically, the reaction is carried out at a temperature ranging from room temperature to about 60° C. and for a time varying from about 30 minutes to about 96 hours.

According to the step h) of the process, the reaction of a compound of formula (XI) with a thiol of formula (XII), may be carried out in a variety of ways and experimental conditions, which are widely known in the art for nucleophilic aromatic substitution. Preferably, this reaction is carried out in a suitable solvent such as, for instance, toluene, tetrahydrofuran, 1,4-dioxane, dimethyl sulfoxide or acetonitrile, in the presence of a base such as sodium, potassium, lithium or cesium carbonate, at a temperature ranging from about −50° C. to reflux and for a period of time varying from about 1 hour to about 96 hours. Phase transfer catalysts may also be added to improve reactivity.

According to the step i) of the process, the oxidation of a compound of formula (XIII) to a compound of formula (XIV) can be carried out in a variety of ways, according to conventional methods for oxidizing sulfides to sulfones. Preferably, this reaction is carried out in a suitable solvent such as, for instance, methanol, ethanol, tert-butanol, water, tetrahydrofuran, 1,4-dioxane, acetic acid, trifluoroacetic acid, dichloromethane, acetonitrile, or a mixture thereof, in the presence of a suitable oxidizing agent, such as, for instance, 3-chloroperbenzoic acid, hydrogen peroxide, urea hydrogen peroxide, oxone, potassium permanganate, sodium periodate, periodic acid and catalytic chromium(VI) oxide. Typically, the reaction is carried out at a temperature ranging from −78° C. to reflux and for a time varying from about 30 minutes to about 96 hours.

According to the step j) of the process, the reaction of a compound of formula (XIV), with hydrazine, may be carried out in a variety of ways and experimental conditions.

Preferably, this reaction is carried out in a suitable solvent such as, for instance, toluene, tetrahydrofuran, 1,4-dioxane, dimethyl sulfoxide, acetonitrile, methanol, ethanol or n-butanol at a temperature ranging from 0° C. to reflux and for a period of time varying from about 1 hour to about 96 hours.

According to step j') of the process the reaction may be carried out in two steps which comprise conversion of a compound of formula (XIV) into a hydrazine derivative of formula (XXIV)

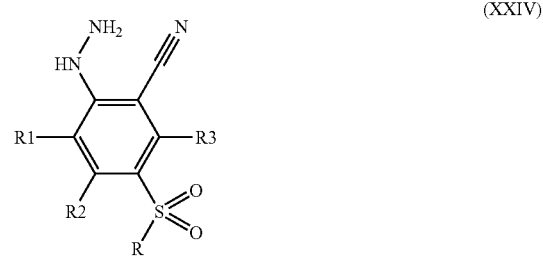

(XXIV)

wherein R, R1, R2, R3 are as defined above, by reaction with hydrazine in a suitable solvent, such as water, methanol, ethanol, diethylether, tetrahydrofuran, 1,4-dioxane or mixtures thereof, at a temperature ranging from 0° C. to reflux and for a period of time varying from about 1 hour to about 96 hours and subsequent intramolecular cyclization of the compound of formula (XXIV) into a compound of formula (VIII). Preferably, this cyclization step can be carried out with the catalysis of an organic or inorganic acid such as acetic acid, trifluoroacetic acid and hydrochloric acid, or silica gel in a suitable solvent such as methanol, ethanol, diethylether, tetrahydrofuran, 1,4-dioxane or mixtures thereof at a temperature ranging from 0° C. to reflux and for a period of time varying from about 1 hour to about 96 hours.

According to the step k) of the process, the reaction of a compound of formula (XIV) with a compound of formula (XV) may be carried out in a variety of ways and experimental conditions. Preferably, this reaction is carried out in a suitable solvent such as, for instance, toluene, tetrahydrofuran, 1,4-dioxane, dimethyl sulfoxide, acetonitrile, methanol, ethanol or n-butanol at a temperature ranging from 0° C. to reflux and for a period of time varying from about 1 hour to about 96 hours. The addition of an acid such as, for example, hydrochloric acid or acetic acid, may be required in order to catalyse the reaction.

According to the step l) of the process, the reaction between a compound of formula (XVI) and a compound of formula (IX) can be carried out in a way analogous to that specified above under f).

According to the step m) of the process, a compound of formula (XVII) is transformed into a compound of formula (I) by deprotection of the pyrazole nitrogen atom according to conventional methods enabling the selective hydrolysis of benzyl, 4-methoxybenzyl, 2,4-dimethoxybenzyl, and triphenylmethyl protecting groups. As an example, this reaction may be run under acidic conditions, for example in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to about 40° C. and for a period of time varying from about 1 hour to about 48 hours.

According to the step n) of the process, a compound of formula (VIII) is transformed into a compound of formula (XVIII) by protection of the primary amino group as phthalimido derivative, according to conventional methods. For example the reaction may be carried out by treatment with phthalic anhydride in a suitable solvent such as pyridine, N,N-dimethylformamide or acetic acid. Typically, the reaction is carried out at a temperature ranging from room temperature to about 110° C. and for a time varying from about 30 minutes to about 96 hours.

According to the step o) of the process, the reaction of a compound of formula (XVIII) with a compound of formula (XIX) may be carried out in a variety of ways and experimental conditions. For example, when R11 is a triphenylmethyl group the reaction may be carried out by treatment with trityl chloride in a suitable solvent such as, for instance, tetrahydrofuran, dichloromethane, toluene, 1,4-dioxane, and in the presence of a proton scavenger such as, for example, triethylamine, N,N-diisopropylethylamine, pyridine, at a temperature ranging from room temperature to reflux, for a time ranging from about 30 min. to about 96 hours.

According to the step p) of the process, a compound of formula (XX) is transformed into a compound of formula (XVI) by selective removal of the phthalimido group, according to conventional methods. For example, the reaction may be carried out by treatment with hydrazine in a suitable solvent such as, for instance, tetrahydrofuran, dichloromethane, toluene, 1,4-dioxane, at a temperature ranging from room temperature to reflux, for a time ranging from about 30 min. to about 96 hours.

According to the step q) of the process, a compound of formula (VIII) is transformed into a compound of formula (XXI) by protection of the primary amino group as trifluoroacetamido derivative, according to conventional methods. For example the reaction may be carried out by treatment with an excess of trifluoroacetic anhydride or trifluoroacetyl chloride in a suitable solvent such as acetonitrile, tetrahydrofuran, toluene, dichloromethane. Typically, the reaction is carried out at a temperature ranging from 0° C. to about 110° C. and for a time varying from about 30 minutes to about 96 hours. Work-up of the reaction mixture with a protic solvent, such as, for instance, water, methanol ethanol or mixtures thereof, or with a water solution of sodium hydrogenocarbonate leads to selective hydrolysis of the trifluoroacetyl group on the pyrazole ring.

According to the step r) of the process, the reaction of a compound of formula (XXI) with a compound of formula (XIX) may be carried out in a variety of ways and experimental conditions. For example when R11 is triphenylmethyl, the reaction may be carried out by treatment with trityl chloride, in a suitable solvent such as, for instance, tetrahydrofuran, dichloromethane, toluene, 1,4-dioxane, and in the presence of a proton scavenger such as, for example, triethylamine, N,N-diisopropylethylamine, pyridine, at a temperature ranging from room temperature to reflux, for a time ranging from about 30 min. to about 96 hours.

According to step s) of the process, a compound of formula (XXII) is transformed into a compound of formula (XVI) by removal of the trifluoroacetyl group, according to conventional methods. For example, the reaction may be carried out by treatment with an organic or inorganic base such as potassium carbonate, sodium hydroxide, ammonia, triethylamine, N,N-diisopropylethylamine in a suitable solvent such as, for instance, tetrahydrofuran, dichloromethane, toluene, 1,4-dioxane, methanol, ethanol, water or mixtures thereof at a temperature ranging from room temperature to reflux, for a time ranging from about 30 min. to about 96 hours.

According to the conversion described under 1) the reduction of a compound of formula (XVII), wherein Ar is a substituted aryl and one of the substituents is nitro, to a compound of formula (XVII), wherein such substituent is amino, can be carried out in a way analogous to that specified above under c).

According to the conversion described under 2) the acylation of a compound of formula (XVII), wherein Ar is a substituted aryl and one of the substituents is amino, can be accomplished in a way analogous to that specified above under f).

According to the conversion described under 3) the reaction of a compound of formula (XVII), wherein Ar is a substituted aryl and one of the substituents is amino, with an aldehyde or a ketone, can be conducted in a variety of ways, according to conventional methods for carrying out reductive alkylations. Preferably, this reaction is carried out in a suitable solvent such as, for instance, methanol, N,N-dimethylformamide, dichloromethane, tetrahydrofuran, or a mixture thereof, in the presence of a suitable reducing agent such as, for instance, sodium borohydride, tetra-alkylammonium borohydride, sodium cyanoborohydride, sodium triacetoxyborohydride, tetramethylammonium triacetoxy borohydride and in presence of an acid catalyst, such as, for instance, acetic acid or trifluoroacetic acid, at a temperature ranging from about 0° C. to reflux and for a time varying from about 1 hour to about 96 hours.

According to the conversion described under 4), hydrolysis of a compound of formula (XVII), wherein Ar is a substituted aryl and one of the substituents is COR4, wherein R4 is OR7 and R7 is methyl or ethyl, can be conducted in a variety of ways, according to conventional methods for hydrolysing carboxylic ester. Preferably this reaction is carried out in a suitable solvent, such as, for instance, water, methanol, ethanol or a mixture thereof, in the presence of an inorganic base such as sodium, lithium or potassium hydroxide at a temperature ranging from about 0° C. to reflux and for a time varying from about 1 hour to about 96 hours.

According to the conversion described under 5), amidation of a compound of formula (XVII), wherein Ar is a substituted aryl and one of the substituents is COR4, wherein R4 is OR7 and R7 is hydrogen, with an amine of formula NHR5R6, wherein R5 and R6 are as defined above, can be conducted in a variety of ways, according to conventional methods for converting carboxylic acids into carboxamides. Preferably this reaction is carried out in a suitable solvent, such as, for instance, tetrahydrofuran, dichloromethane, toluene, 1,4-dioxane, N,N-dimethylformamide in the presence of a coupling agent such as, for example, O-benzotriazol-1-yl-N,N,N',N'-tetramethyluronium tetrafluoroborate (TBTU) or a carbodiimide such as, for instance, N,N'-dicyclohexylcarbodiimide or 1-ethyl-3-(3-dimethylaminopropyl)carbodiimide hydrochloride (EDC) optionally in the presence of an additive such as 1-hydroxybenzotriazole, at a temperature ranging from about 0° C. to reflux and for a time varying from about 1 hour to about 96 hours. A proton scavenger can also be added such as, for example, triethylamine, N,N-diisopropylethylamine or pyridine.

According to the conversion described under 6) the reduction of a compound of formula (I), wherein Ar is a substituted aryl and one of the substituents is nitro, to a compound of formula (I) wherein such substituent is amino, can be carried out in a way analogous to that specified above under c).

According to the conversions described under 7) a compound of formula (I) can be converted into another compound of formula (I) in a way analogous to that specified above under 2) employing an excess of a carboxylic acid derivative of formula (XXIII), wherein W is as defined above, followed by the selective cleavage of the acyl group on the pyrazole ring according to the procedure described under g).

According to the conversions described under 8) a compound of formula (I) can be converted into another compound of formula (I) in a way analogous to that specified above under 3).

The deprotection of a compound of formula (XVII) or (I) wherein Ar is a substituted aryl and one of the substituents is a protected amino group, can be made in a variety of ways according to conventional methods for deprotecting amino groups. Depending on the amino protecting group, this reaction can be conducted in different ways. In one aspect, such reaction can be carried out by treatment with an inorganic acid, such as hydrochloric, sulphuric or perchloric acid, or an organic acid, such as trifluoroacetic or methanesulfonic acid, in a suitable solvent, such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −10° C. to 80° C., and for a period of time ranging from 30 minutes to 48 hours. In another aspect, such reaction can be carried out by treatment with an inorganic base, such as lithium or sodium or potassium hydroxide, or sodium or potassium or cesium carbonate, or with an organic base, such as triethylamine or N,N-diisopropylethylamine, or with anhydrous hydrazine or hydrazine hydrate in a suitable solvent such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −10° C. to 80° C., and for a period of time ranging from 30 minutes to 72 hours. In still another option, such reaction can be carried out by treatment with hydrogen or cyclohexene or cyclohexadiene and a hydrogenation catalyst, such as palladium on carbon, or with a metal, such as zinc, and an inorganic or organic acid, such as hydrochloric or acetic acid, in a suitable solvent such as water, methanol, ethanol, 1,4-dioxane, tetrahydrofuran or mixture thereof, at a temperature ranging from −10° C. to 80° C., and for a period of time ranging from 30 minutes to 72 hours.

Substituted indazole derivatives can be prepared using standard procedures in organic synthesis as reported, for instance, in Smith, Michael—*March's Advanced Organic Chemistry: reactions mechanisms and structure*—$5^{th}$ *Edition*, Michael B. Smith and Jerry March, John Wiley & Sons Inc., New York (NY), 2001. It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M. —*Protective Groups in Organic Synthesis, Third Edition*, John Wiley & Sons Inc., New York (NY), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H., —*Enantiomers, Racemates, and Resolutions*, John Wiley & Sons Inc., New York (NY), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The starting materials of the process of the present invention, i.e. compounds of formula (II), (IV), (IX), (XI), (XII), (XV), (XIX) and (XXIII), are either known or can be prepared according to known methods.

For example, the compounds of formula (IV) are either known or can be easily obtained by reduction of the corresponding sulfonyl chlorides. The compounds of formula (IX) and (XXIII), for instance those wherein W and Z represents a halogen atom, e.g. a chlorine atom, are either known or can be easily obtained from the corresponding carboxylic acids, that are either known or can be prepared by working according to conventional synthetic methods.

Pharmacology

The short forms and abbreviations used herein have the following meaning:

| | |
|---|---|
| Ci | Curie |
| DMSO | dimethylsulfoxide |
| ID | identity |
| KDa | kiloDalton |
| microCi | microCurie |
| mg | milligram |
| microg | microgram |
| mL | milliliter |
| microL | microliter |
| M | molar |
| mM | millimolar |
| microM | micromolar |
| nM | nanomolar |

Assays

Compounds of the present invention were tested in biochemical as well as in cell-based assays, as described below.

Preparation of IGF-1R for Use in Biochemical Assay

Cloning and Expression

Human cDNA was used as template for amplification by polymerase chain reaction (PCR) of the predicted cytoplasmic portion of IGF-1R (amino acid residues 960-1367 of precursor protein; see NCBI Entrez Protein Accession #P08069) which includes the entire kinase domain. PCR was conducted using the forward primer sequence 5'-CTCG-GATCCAGAAAGAGAAATAACAGCAGGCTG-3' [SEQ ID NO: 1] and the reverse primer sequence 5'-CTCGGATC-CTCAGCAGGTCGAAGACTGGGGCAGCGG-3'[SEQ ID NO: 2].

In order to facilitate subsequent cloning steps, both primers comprise a BamHI restriction endonuclease site sequence. This PCR product was cloned in frame using BamHI sticky ends into a transfer vector for the baculovirus expression system, pVL1392 (Pharmingen), previously modified by insertion into the pVL1392 multiple cloning site of sequences encoding Glutathione S-transferase (GST) fusion protein, PreScission protease cleavage site and partial MCS cassette derived from the pGex-6P plasmid (Amersham BioSciences). Insertion of the IGF-1R PCR product described above into the pGex-6P derived BamHI site of the modified pVL1392 vector results in an open reading frame corresponding to the pGEX-6P GST protein and PreScission peptide fused with the human IGF-1R cytoplasmic domain. In order to obtain fusion protein, Sf21 insect cells (Invitrogen) are cotransfected with 2 microg of purified plasmid and 1 microg of virus DNA (BaculoGold™ Transfection Kit, Pharmingen), as described in the Baculovirus Instruction manual (Pharmingen). A first amplification of the virus is performed using 600 microL of cotransfected virus on $6 \times 10^6$ Sf21 in a monolayer culture, in 12 mL of medium (TNM-FH Grace's medium—Pharmingen). After 3 days the medium is collected, centrifuged and transferred to a sterile tube. A second amplification is prepared with the same method using 2 mL on $3 \times 10^7$ cells, diluted in 40 mL of medium. For the third amplification of virus, 1 mL of supernatant from the second round are used per $3 \times 10^7$ cells diluted in 40 mL of medium.

Protein expression is performed in H5 insect cells infected with 14 mL virus/$1 \times 10^9$ insect cells (MOI=1.5) for 65 h with shaking at 27° C. Cells are harvested by centrifugation at 1200×g for 10 minutes.

Protein Purification

Cells were resuspended in phosphate buffered saline solution (PBS), 20 mM dithiothreitol (DTT), 0.2% CHAPS, 20% glycerol, 1 mM OVA, "Complete" protease inhibitor cocktail (1 tablet/50 mL buffer; Roche Diagnostics, Milan, Italy) and lysed by liquid extrusion with a Gaulin homogenizer (Niro Soavi, Italy). The lysate was centrifuged at 14000×g for 45 minutes and the supernatant was loaded onto a column containing 10 mL Glutathione Sepharose (Amersham Biosciences). The column was first washed with PBS buffer for 5 column volumes, then with 100 mM Tris pH 8.0, 20% glycerol for 5 column volumes, and lastly eluted with 10 mM glutathione in 100 mM Tris pH 8.0, 20% glycerol. Fractions of 10 mL were collected, and protein-rich fractions were pooled. Typically, 20 mg of fusion protein were recovered from $1 \times 10^9$ cells, and this was typically >85% pure as judged by SDS-PAGE followed by Coomassie staining Purified protein was stored at −80° C. prior to its use in biochemical assays.

Biochemical Assay for Inhibitors of IGF-1R Kinase Activity

The inhibitory activity of putative kinase inhibitors and the potency of selected compounds were determined using a trans-phosphorylation assay.

A specific substrate was incubated with the kinase in appropriate buffer conditions in the presence of ATP traced with $^{33}$P-γ-ATP (gamma phosphate-labeled, Redivue™ Code Number AH9968, 1000-3000 Ci/mmole, Amersham Biosciences Piscataway, N.J., USA), optimal cofactors and test compound.

At the end of the phosphorylation reaction, more than 98% cold and radioactive ATP were captured by an excess of Dowex ion exchange resin. The resin was allowed to settle to the bottom of reaction wells by gravity. Supernatant, containing substrate peptide, was subsequently withdrawn and transferred into a counting plate, and radioactivity (corresponding to phosphate incorporated into peptide) was evaluated by β-counting.

Reagents/Assay Conditions i. Dowex Resin Preparation 500 g of wet resin (SIGMA, custom prepared DOWEX resin 1×8 200-400 mesh, 2.5 Kg) were weighed out and diluted to 2 L in 150 mM sodium formate, pH 3.00.

The resin was allowed to settle for several hours and then the supernatant was discarded. This washing procedure was repeated three times over two days. Finally, the resin was allowed to settle, supernatant was discarded and two volumes (with respect to the resin volume) of 150 mM sodium formate buffer were added. The final pH was circa 3.0. The washed resin was kept at 4° C. before use, and was stable for more than one week.

ii. Kinase Buffer (KB)

Kinase buffer was composed of 50 mM HEPES pH 7.9 containing 3 mM MgCl$_2$, 1 mM DTT, 3 microM Na$_3$VO$_4$, and 0.2 mg/mL BSA. 3×KB is buffer of the same composition and pH as KB, but with three times the concentration of each component.

iii. Enzyme Pre-Activation and Preparation of 3× Enzyme Mix.

Prior to starting the kinase inhibition assay, IGF-1R was pre-phosphorylated in order to linearize reaction kinetics. To achieve this, the desired total quantity of enzyme was prepared at an enzyme concentration of 360 nM in KB containing 100 microM ATP, and this preparation was incubated for 30 min at 28° C. 3× Enzyme Mix was obtained by diluting this preactivated enzyme 20-fold in 3×KB.

iv. Assay Conditions

The kinase assay was run with a final enzyme concentration of 6 nM, in the presence of 6 microM ATP, 1 nM $^{33}$P-γ-ATP and 10 microM substrate, a carboxy-terminally biotinylated peptide of the following sequence: KKKSPGEYVNIEFGGGGGK-biotin. The peptide was obtained in batches of >95% peptide purity from American Peptide Company, Inc. (Sunnyvale, Calif., USA).

Robotized Dowex Assay

Test reactions were performed in a total final volume of 21 microL consisting of:

a) 7 microL/well of 3× Enzyme Mix (18 nM preactivated enzyme in 3× kinase buffer), b) 7 microL/well of 3× substrate/ATP mix (30 microM substrate, 18 microM ATP, 3 nM $^{33}$P-γ-ATP in double-distilled water (ddH$_2$O), c) 7 microL/well 3× test compounds diluted into ddH$_2$O-3% DMSO.

Compound Dilution and Assay Scheme is Reported Below.

i. Dilution of Compounds 10 mM stock solutions of test compounds in 100% DMSO were distributed into 96 well 12×8 format microtiter plates.

For % inhibition studies, dilution plates at 1 mM, 100 microM and 10 microM were prepared in 100% DMSO, then diluted to 3× final desired concentration (30, 3 and 0.3 microM) in ddH$_2$O, 3% DMSO. A Multimek 96 (Beckman Coulter, Inc. 4300 N. Harbor Boulevard, P.O. Box 3100 Fullerton, Calif. 92834-3100 USA) was used for compound pipetting into test plates.

For 1050 determination, starting solutions of 30 microM compound in 3% DMSO were derived from 1 mM/100% DMSO stock solutions. These 30 microM starting solutions were used for generation of a further 9 serial ⅓ dilutions in ddH$_2$0, 3% DMSO, so as to generate a 10-point dilution curve at 3× the final assay concentration. Serial dilution was conducted in 96-well plates using a Biomek 2000 (Beckman Coulter) system. Dilution curves of 7 compounds/plate were prepared, and each plate also included a 10-point dilution curve of Staurosporine, as well as several negative and positive control wells.

ii. Assay Scheme 7 microL of each test compound dilution (or control) in ddH$_2$O, 3% DMSO were pipetted into each well of a 384-well, V-bottom assay plate, which was then transferred to a PlateTrak 12 robotized station (Perkin Elmer, 45 William Street Wellesley, Mass. 02481-4078, USA) equipped with one 384-tip pipetting head for starting the assay, plus one 96-tip head for dispensing the resin) prepared with reservoirs containing sufficient 3× Enzyme mix and 3×ATP mix (3×) to complete the assay run.

At the start of the assay the liquid handling system aspirates 7 microL of ATP mix, introduces an air gap inside the tips (5 microL) and then aspirates 7 microL of 3× Enzyme Mix. To start the reaction, tips contents were dispensed into the test wells already containing 7 microL test compound (at 3× desired final concentration), followed by 3 cycles of mixing, so as to restore desired final concentration for all reaction components.

Plates were incubated for 60 minutes at room temperature, and then the reaction was stopped by pipetting 70 microL of Dowex resin suspension into the reaction mix, followed by three cycles of mixing. After stopping the reaction, plates were allowed to rest for one hour in order to maximize ATP capture. At this point, 20 microL of supernatant were transferred from each well into wells of 384-Optiplates (Perkin Elmer) containing 70 microL/well of Microscint 40 (Perkin Elmer); after 5 min of orbital shaking the plates were read on a Perkin-Elmer Top Count radioactivity counter.

iii. Data Analysis

Data were analysed using a customized version of the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted.

Compounds showing desired inhibition were further analysed in order to study the potency of the inhibitor through IC$_{50}$ calculation. In this case, inhibition data obtained using serial dilutions of the inhibitor were fitted by non-linear regression using the following equation:

$$v = v_0 + \frac{(v_0 - v_b)}{1 + 10^{n(\log IC_{50} - \log[I])}}$$

where $v_b$ is the baseline velocity, v is the observed reaction velocity, $v_o$ is the velocity in the absence of inhibitors, and [I] is the inhibitor concentration.

Cell-Based Assays for Inhibitors of IGF-1R Kinase Activity
Western Blot Analysis of Receptor Phosphorylation Following Stimulation with IGF-1 in MCF-7 Human Breast Cancer Cells MCF-7 cells (ATCC# HTB-22) were seeded in 12-well tissue culture plates at 2×10$^5$ cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing ⅟$_{1000}$ rabbit anti-phospho IGF-1R Tyr1131/InsR Tyr 1146 antibody (product #3021, Cell Signaling Technology, Beverly, Mass., USA) for the detection of phosphorylated IGF-1R, or ⅟$_{1000}$ dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+ 0.15% Tween 20, and incubated for 1 hour in washing buffer containing ⅟$_{5000}$ dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% CO$_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at ⅟$_{200}$ dilution in PBS/1% milk/

0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+ 1/500 Goat anti-rabbit Cy5™-conjugated secondary antibody (Amersham Biosciences, Little Chalfont, Buckinghamshire, UK). Wells were then washed ×2 with PBS, and 40 microL PBS were dispensed in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

Preparation of ALK Cytoplasmic Domain for Use in Biochemical Assay

Cloning and Expression

ALK cytoplasmic domain, corresponding to residues 1060-1620 (the numbers of the amino acid residues refer to the Genbank accession number NP 004295.2) was PCR amplified from a human testis cDNA library.

Amplification was performed using the forward oligonucleotide:

[SEQ ID NO: 3]
5'GGGGACAAGTTTGTACAAAAAAGCAGGCTTACTGGAAGTTCTGTTCCA

GGGGCCCCGCCGGAAGCACCAGGAGCTG-3' and the reverse oligonucleotide:

[SEQ ID NO: 4]
5'GGGGACCACTTTGTACAAGAAAGCTGGGTTTCAGGGCCCAGGCTGGTT

CATGCTATT-3'.

For cloning purposes, the oligonucleotides included attB sites in order to obtain an attB-flanked PCR product suitable for cloning using the Gateway technology (Invitrogen). Furthermore, for purification purposes, forward primer included a PreScission cleavage site (Amersham Biosciences). The resulting PCR product was cloned in the baculovirus expression vector pVL1393 (Invitrogen), Gateway-modified. For expression and purification purposes, a GST tag was added N-terminal to the ALK cytoplasmic domain. Cloning was performed according to the protocols described in the Gateway manual (Invitrogen).

Baculovirus was generated by cotransfecting Sf9 insect cells with expression vector and the viral DNA using the BaculoGold™ transfection kit (Pharmingen).

Viral supernatant was recovered after 5 days and subjected to 3 rounds of amplification to increase viral titer.

Recombinant protein was produced by infecting Sf21 insect cells at the density of $1 \times 10^6$ cells/mL with 30 mL viral supernatant per billion cells with shaking at 27° C. After 48 hours of infections the cells were recovered, pelleted and frozen at −80° C.

Protein Purification

Cells were resuspended in lysis buffer (Tris-HCl 50 mM pH8, NaCl 150 mM, CHAPS 0.2%, DTT 20 mM, glycerol 20%, "Complete" protease inhibitor cocktail (Roche Diagnostics), $Na_3VO_4$ 1 mM and lysed by liquid extrusion with a Gaulin homogenizer (Niro Soavi Italy). The lysate was cleared by centrifugation at 20000 g for 30 minutes and loaded on a Glutathione Sepharose 4B (Amersham Biosciences) column.

After extensive wash, recombinant protein was eluted with 10 mM Glutathione in 100 mM Tris-HCl pH8, 10% glycerol.

Affinity purified GST-ALK was loaded on a Heparin Sepharose™ FF (Amersham Biosciences) column and eluted with 50 mM NaCl, 25 mM TRIS pH 7.5, 2 mM DTT, 20% glycerol.

The eluted fractions were pooled and dialyzed against 150 mM NaCl, 50 mM Tris-HCl pH 7.4, 2 mM DTT, 20% glycerol.

Purified protein was stored at −80° C. prior its use in biochemical assay.

Biochemical Assay for Inhibitors of ALK Kinase Activity

The in vitro kinase inhibition assay was conducted in the same way as described for IGF-1R. As for IGF-1R, ALK enzyme needs pre-activation in order to linearize reaction kinetics.

i. Kinase Buffer (KB) for ALK

Kinase buffer was composed of 50 mM HEPES pH 7.5 containing 1 mM $MnCl_2$, 5 mM $MgCl_2$, 1 mM DTT, 3 microM $Na_3VO_4$, and 0.2 mg/mL BSA. 3×KB is buffer of the same composition and pH as KB, but with three times the concentration of each component.

ii. Assay Conditions

The kinase assay was run with a final enzyme concentration of 20 nM, in the presence of 8 microM ATP, 1 nM $^{33}P$-γ-ATP and 2 microM MBP. The MBP was purchased from Sigma-Aldrich, St. Louis, Mo., USA.

Cell-Based Assays for Inhibitors of ALK Kinase Activity

Western Blot Analysis of ALK and STAT3 Phosphorylation in Karpas-299, SR-786 and SUP-M2 Anaplastic Large Cell Lymphoma Cell Lines Karpas-299, SR-786 and SUP-M2 cells (DSMZ, Braunschwiegh, Germany) were seeded in 6-well tissue culture plates at $5 \times 10^5$ cells/mL in RPMI-1640 medium+2 mM glutamine+10% to 15% FCS (EuroClone, Italy), and incubated overnight at 37° C., 5% $CO_2$, 100% relative humidity. After this incubation, cells were treated with desired concentrations of compound for 2 hours at 37° C. Cells were collected by centrifugation at 248×g for 5 minutes, washed with cold PBS, centrifuged again at 248×g for 5 minutes and then lysed in 100 mM Tris-HCl pH 7.4, 2% SDS, 1 mM $Na_3VO_4$, protease inhibitor cocktail [Sigma-Aldrich product #P8340], phosphatase inhibitor cocktail [Sigma-Aldrich products #P2850+#P5726]). After brief sonication, cell lysates were cleared by centrifugation at 10,000×g for 20 minutes at room temperature and 20 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% Non-fat Dry Milk [#1706404 Bio-rad, Hercules, Calif., USA]+0.1% Tween 20), and probed over night in TBS+5% BSA+0.1% Tween 20 at 4° C. containing 1/500 anti-phosho-ALK Tyr 1604 antibody (product #3341 Cell Signaling Technology, Beverly, Mass., USA) for detection of phosphorylated ALK or 1/500 mouse anti-ALK antibody (product #35-4300, Zymed Laboratories, South San Francisco, Calif., USA) for the detection of total ALK or 1/500 mouse anti-phospho STAT3 Tyr 705 antibody (product #612357, BD Transduction Laboratories, Canada) for detection of phosphorylated STAT3 or 1/1000 mouse anti-STAT3 antibody (product #610190 BD Transduction Laboratories, Canada) for detection of total STAT3.

In all cases, filters were then washed for 20 minutes with several changes of TBS+0.1% Tween 20, and incubated for 1 hour in TBS+5% Non-fat Dry Milk+0.1% Tween 20 containing 1/10000 dilution of horseradish peroxidase conjugated anti-rabbit or mouse IgG (Amersham, product # NA934), then were washed again and developed using the ECL chemiluminescence system (Amersham) according to manufacturer's recommendations. Unless otherwise stated, reagents used were from Sigma-Aldrich, St. Louis, Mo., USA.

In Vitro Cell Proliferation Assay for Inhibitors of ALK Kinase Activity

The human ALCL cell lines Karpas-299, SR-786 and SUP-M2 were seeded in 96 well plates (PerkinElmer, Wellesley, Mass., USA) $1\times10^5$ cells/mL in RPMI-1640 medium+2 mM glutamine+10% to 15% FCS (EuroClone, Italy), (100 microL/well) and maintained at 37° C., 5% $CO_2$, 100% relative humidity. The following day, plates were treated in duplicate with an appropriate dilution of compounds starting from a 10 mM stock solution in DMSO (final DMSO concentration: 0.1%). Eight untreated control wells were included in each plate. After 72 hours of treatment, 50 microL of CellTiter-Glo Assay (Promega, Madison, Wis., USA) were added to each well and after agitation the luminescence signal is measured using an Envision Detector (PerkinElmer Wellesley, Mass., USA).

$IC_{50}$ values were calculated by LSW/Data Analysis using Microsoft Excel sigmoidal curve fitting.

Biochemical Assay for Inhibitors of Aurora-2 Kinase Activity

The in vitro kinase inhibition assay was conducted mimilarly as described for IGF-1R. At variance with IGF-1R, however Aurora-2 enzyme does not require pre-activation.

i. Kinase Buffer (KB) for Aurora-2

The kinase buffer was composed of 50 mM HEPES, pH 7.0, 10 mM $MgCl_2$, 1 mM DTT, 3 microM $Na_3VO_4$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}P$-γ-ATP, and 8 microM substrate, composed of 4 LRRWSLG repeats.

Cell-Based Assays for Inhibitors of Aurora-2 Kinase Activity
In Vitro Cell Proliferation Assay for Inhibitors of Aurora-2 Kinase Activity The human colon cancer cell line HCT-116 was seeded at 5000 cells/$cm^2$ in 24 well plates (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicate with 5 mL of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of CTR=(Treated−Blank)/(Control−Blank)/100.

$IC_{50}$ values were calculated by LSW/Data Analysis using Microsoft Excel sigmoidal curve fitting.

Biochemical and cell-based assay data for representative compounds are reported in Table 1.

TABLE 1

| Compound | IGF1R $IC_{50}(\mu M)$ | ALK $IC_{50}(\mu M)$ | Aur2 $IC_{50}(\mu M)$ | IGF1-induced S6 phosphorylation $IC_{50}(\mu M)$ |
|---|---|---|---|---|
| 1 | 0.85 | 0.34 | 0.026 | >10 |
| 36 | 0.23 | 0.17 | 0.019 | 1.2 |
| 33 | 0.036 | 0.034 | 0.009 | 0.27 |

The same compounds were tested for inhibition of IGF 1-induced IGF-1R phosphorylation in MCF-7 cells and results are shown in FIG. 1.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route. For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

Figure 1:
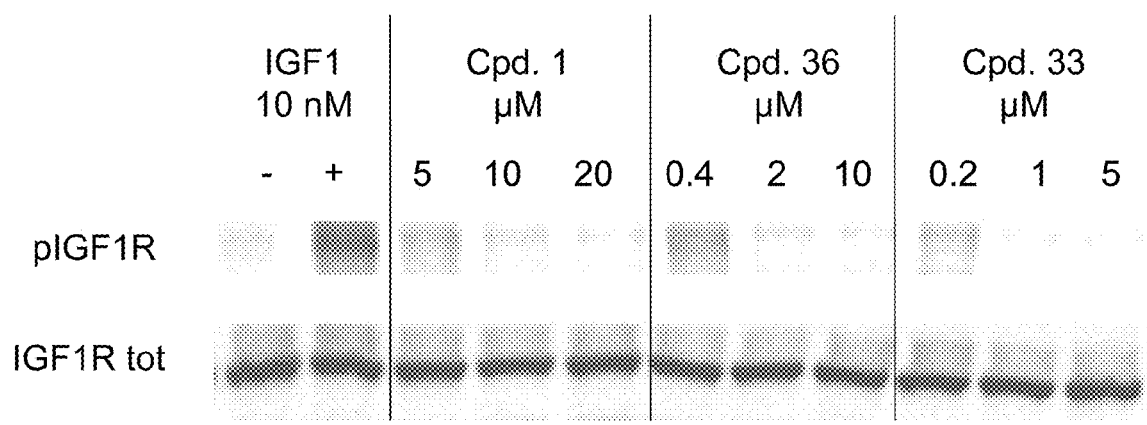
FIG. 1 shows the inhibition of IGF1R auto-phosphorylation in MCF7 starved cells stimulated with 10 nM IGF1 by compounds of formula (I), exemplified by compound 1, 36 and 33.

Treatment of starved MCF7 cells with 10 nM IGF1 induced receptor auto-phosphorylation as shown by the appearance of a more intense band of phosphorylated IGF1R (pIGF1R). Incubation of cells with increasing concentrations of compound 1, 36, and 33 prior to treatment with IGF1 resulted in inhibition of IGF1-induced IGF1R auto-phosphorylation as shown by the disappearance of the band of phosphorylated IGF1R (pIGF1R).

EXPERIMENTAL SECTION

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Acid method: mobile phase A was water-0.01% trifluoroacetic acid, and mobile phase B was acetonitrile; gradient from 10 to 90% B in 8 min, hold 90% B 2 min; flow rate 20 mL/min. Basic method: mobile phase A was water-0.1% $NH_3$, and mobile phase B was acetonitrile; gradient from 10 to 100% B in 8 min, hold 100% B 2 min; flow rate 20 mL/min.

1H-NMR spectrometry was performed on a Mercury VX 400 operating at 400.45 MHz equipped with a 5 mm double resonance probe [1H (15N-31P) ID_PFG Varian].

Example 1

Preparation of
5-benzenesulfonyl-1H-indazol-3-ylamine [(VIII),
R1=R2=R3=H, R=phenyl]

Step 1. 5-fluoro-2-nitro-benzamide [(III),
R1=R2=R3=H]

5-Fluoro-2-nitro-benzoic acid (17.9 g, 96.8 mmol) was heated in thionyl chloride (35 mL, 5 mol eq.) for two hours at 85° C. (oil bath temperature). The reaction mixture was evaporated, taken up and evaporated twice with dry toluene. The resulting acid chloride was dissolved in dry dioxane (180 mL) and added to an ice-water bath cooled solution of 33% $NH_4OH$ (23.5 mL, 2 mol eq.) in dioxane (180 mL). The reaction was allowed to warm up gradually to room temperature and then evaporated to dryness. The crystalline residue was triturated in water (50 mL), collected by filtration, washed with a small amount of water and dried in vacuo at 80° C. to constant weight (17.56 g, 98.5%).

1H-NMR (400 MHz), δ (ppm, DMSO-$d_6$): 8.12-8.19 (m, 2H), 7.79 (bs, 1H), 7.50-7.57 (m, 2H).

Step 2. 5-benzenesulfonyl-2-nitro-benzamide [(V),
R1=R2=R3=H, R=phenyl]

5-Fluoro-2-nitro-benzamide (2.5 g, 13.59 mmol) in DMSO (40 mL) was treated with solid 97% $PhSO_2Na$ (2.48 g, 14.95 mmol) and heated at 50° C. (oil bath temperature) for 60 hours. The reaction was added dropwise into 40 mL of iced water. Filtration of the solid afforded 3.55 g (85% yield) of title compound.

1H-NMR (400 MHz), δ (ppm, DMSO-$d_6$): 8.41 (bs, 1H), 8.25, 8.27 (m, 1H), 8.21, 8.19 (m, 1H), 8.19 (m, 1H), 8.07 (m, 2H), 7.92 (bs, 1H), 7.78 (m, 1H), 7.69 (m, 2H).

Step 3. 2-amino-5-benzenesulfonyl-benzamide [(VI),
R1=R2=R3=H, R=phenyl]

5-Benzenesulfonyl-2-nitro-benzamide (3.13 g, 10.23 mmol) was suspended in absolute ethanol (200 mL), treated with 10% Pd/C (1.5 g) and then with ammonium formate (9.7 g, 153 mmol). The mixture was stirred at reflux. After a couple of hours the reaction was complete. After cooling to room temperature the reaction was filtered over celite and the panel was washed with EtOH. Evaporation of the filtrate left the crude product that was taken up with a small amount of methanol and added dropwise to 400 mL of iced water kept under stirring. The solid thus formed was filtered and washed with water affording 1.87 g of title compound (66% yield).

1H-NMR (400 MHz), δ (ppm, DMSO-$d_6$): 8.14, 7.31 (m, 2H), 7.92 (m, 2H), 7.59 (m, 4H), 7.45 (bs, 2H), 6.81 (m, 1H).

Step 4. 2-amino-5-benzenesulfonyl-benzonitrile [(VII), R1=R2=R3=H, R=phenyl]

2-Amino-5-benzenesulfonyl-benzamide (2.01 g, 7.29 mmol) was treated with $POCl_3$ (8 mL) and the reaction was heated to 90° C. The solid gradually dissolved. After three hours the reaction was cooled to room temperature and added dropwise to 600 mL of iced water kept under stirring.

A yellow precipitate was obtained that was filtered. Purification of the crude by chromatography over silica gel (DCM/MeOH/96:4 or DCM/EtOAc 93:7) gave 813 mg of title compound (43% yield).

1H-NMR (400 MHz), δ (ppm, DMSO-$d_6$): 8.02 (d, J=2.31 Hz), 1H), 7.94 (m, 2H), 7.75 (dd, J1=9.02 Hz, J2=2.31 Hz, 1H), 7.67 (m, 1H), 7.61 (m, 2H), 7.08 (bs, 2H), 6.87 (d, J=9.02 Hz, 1H).

Step 5. 5-benzenesulfonyl-1H-indazol-3-ylamine [(VIII), R1=R2=R3=H, R=phenyl]

2-Amino-5-benzenesulfonyl-benzonitrile (0.81 g, 3.15 mmol) in 37% HCl (5 mL) was treated dropwise at 4° C. with $NaNO_2$ (261 mg, 3.78 mmol) in 5 mL of water. After 1.75 hours the suspension was added dropwise to a solution of $SnCl_2$ (4.88 g, 25.21 mmol) in 5 mL of 37% HCl. After stirring at 4° C. for 3 hours the solid was filtered, taken up with water (30 mL) and boiled for 1.5 hours. The hot mixture was filtered and washed thoroughly with boiling water. The filtrate was cooled to 4° C. and treated under stirring with 17% NaOH (approximately 5 mL) dropwise. After overnight cooling in a fridge the solid was filtered and washed with water to neutral pH affording 0.348 g of title compound (40% yield).

1H-NMR (400 MHz), δ (ppm, DMSO-$d_6$): 11.98 (bs, 1H), 8.55 (m, 1H), 7.90 (m, 2H), 7.58-7.70 (m, 4H), 7.39 (m, 1H), 5.79 (bs, 2H).

Example 2

Preparation of 5-(3,5-difluoro-benzenesulfonyl)-1H-indazol-3-ylamine [(VIII), R1=R2=R3=H, R=3,5-difluorophenyl]

Step 1. 5-(3,5-difluoro-phenylsulfanyl)-2-nitro-benzonitrile [(XIII), R1=R2=R3=H, R=3,5-difluorophenyl]

A solution of 5-fluoro-2-nitrobenzonitrile (2.4 g, 14.45 mmol) in tetrahydrofuran (100 mL) was treated with cesium carbonate (4.7 g) and cooled to −15° C. (ice/salt bath). To this mixture, 3,5-difluorothiophenol (2.11 g, 1 mol eq.) in tetrahydrofuran (50 mL) was added dropwise within 30 minutes. After further stirring for 1 hour, the reaction was checked for the presence of any unreacted starting material. Most of the solvent was removed by rotoevaporation and the residue partitioned between dichloromethane and water. The organic layer was dried over sodium sulfate and evaporated to afford the product as a solid. Trituration in a small amount of methanol and filtration gave the title compound in pure form as whitish powder (3.25 g, 77%).

1H-NMR (400 MHz), δ (ppm, DMSO-$d_6$): 8.31 (d, J=8.80 Hz, 1H), 8.11 (d, J=2.11 Hz, 1H), 7.68 (dd, J1=8.80 Hz, J2=2.11 Hz, 1H), 7.46 (m, 1H), 7.39 (m, 2H).

Operating in an analogous way, the following compounds were obtained:

2-Nitro-5-phenylsulfanyl-benzonitrile [(XIII), R1=R2=R3=H, R=phenyl]

1H-NMR (400 MHz), δ (ppm, DMSO-$d_6$): 8.28 (d, J=8.8 Hz, 1H), 7.83 (d, J=2.1 Hz, 1H), 7.65-7.56 (m, 5H), 7.45 (dd, J1=8.8 Hz, J2=2.1 Hz, 1H).

5-(3-Fluoro-phenylsulfanyl)-2-nitro-benzonitrile [(XIII), R1=R2=R3=H, R=3-fluorophenyl]

1H-NMR (400 MHz), δ (ppm, DMSO-$d_6$): 8.31 (d, J=8.9 Hz, 1H), 7.98 (d, J=2.2 Hz, 1H), 7.65-7.41 (m, 5H).

Step 2. 5-(3,5-difluoro-benzenesulfonyl)-2-nitro-benzonitrile [(XIV), R1=R2=R3=H, R=3,5-difluorophenyl]

Periodic acid (10.14 g, 4 mol eq) was stirred in dry acetonitrile (220 mL) until completely dissolved. Chromium trioxide (22 mg, 0.02 mol eq.) was added and stirred until completely dissolved. After cooling by means of an ice-water bath, a solution of 5-(3,5-difluoro-phenylsulfanyl)-2-nitro-benzonitrile (3.25 g, 11.12 mmol) in dry acetonitrile was added with stirring. The cooling bath was removed and the reaction was stirred for 2 hours. The precipitate was filtered off, washed with fresh acetonitrile and the combined solutions were rotoevaporated. The residue was taken up with dichloromethane, washed successively with saturated aqueous sodium sulphite and brine, dried over sodium sulphate and evaporated to afford the title compound as a white solid (3.53 g, 98%).

1H-NMR (400 MHz), δ (ppm, DMSO-$d_6$): 8.91 (m, 1H), 8.58 (m, 2H), 7.97 (m, 2H), 7.78 (m, 1H).

Operating in an analogous way, the following compounds were obtained:

5-Benzenesulfonyl-2-nitro-benzonitrile [(XIV), R1=R2=R3=H, R=phenyl]

1H-NMR (400 MHz), δ (ppm, DMSO-$d_6$): 8.82 (m, 1H), 8.56-8.49 (m, 2H), 8.16-8.11 (m, 2H), 7.79 (m, 1H), 7.73-7.67 (m, 2H).

5-(3-Fluoro-benzenesulfonyl)-2-nitro-benzonitrile [(XIV), R1=R2=R3=H, R=3-fluorophenyl]

1H-NMR (400 MHz), δ (ppm, DMSO-$d_6$): 8.88 (m, 1H), 8.55 (m, 2H), 8.07 (m, 1H), 7.99 (m, 1H), 7.76 (m, 1H), 7.67 (m, 1H).

Step 3. 5-(3,5-difluoro-benzenesulfonyl)-1H-indazol-3-ylamine [(VIII), R1=R2=R3=H, R=3,5-difluorophenyl]

5-(3,5-Difluoro-benzenesulfonyl)-2-nitro-benzonitrile (3.5 g, 10.8 mmol) was heated in anhydrous ethanol (175 mL) until completely dissolved. The solution was then treated with hydrazine hydrate (0.58 mL, 1.1 mol eq.) and refluxed for three hours. The reaction mixture was evaporated to dryness; the residue was dissolved in acetone, adsorbed onto flash chromatography-grade silica gel by rotoevaporation of the solvent. The silica was loaded onto a flash chromatography column conditioned with 10:1 dichloromethane/acetone. The column was then eluted with dichloromethane/acetone (gradient: from 10:1 to 2:1) followed by a final washing with dichloromethane/acetone/methanol. The pure fractions were collected and evaporated to afford the title compound as a whitish crystalline powder (2.44 g, 73%).

1H-NMR (400 MHz), δ (ppm, DMSO-$d_6$): 12.05 (bs, 1H), 8.58 (d, J=1.46 Hz, 1H), 7.76 (dd, J1=8.78 Hz, J2=1.83 Hz, 1H), 7.60-7.68 (m, 3H), 7.40 (dd, J1=8.90 Hz, J2=0.61 Hz, 1H), 5.81 (bs, 1H).

Operating in an analogous way, the following compounds were obtained:

5-(3-Fluoro-benzenesulfonyl)-1H-indazol-3-ylamine [(VIII), R1=R2=R3=H, R=3-fluorophenyl]

ESI (+) MS: m/z 292 (MH+).

Example 3

Preparation of 2-nitro-4-piperidin-1-ylmethyl-benzoic acid methyl ester

To a solution of 4-hydroxymethyl-2-nitro-benzoic acid methyl ester (2.0 g, 9.47 mmol) in dry dichloromethane (80 mL) under argon, at room temperature, triethylamine (1.6 mL, 10.9 mmol, 1.15 eq.) and then p-toluenesulfonyl chloride (2.08 g, 10.9 mmol, 1.15 eq.) were added. The reaction mixture was stirred at room temperature for 1 h, then piperidine (1.6 mL, 18.94 mmol, 2 eq.) was added and the mixture stirred for additional 24 hours. The solvent was evaporated and the residue purified by flash chromatography on silica gel, using dichloromethane/ethanol 95:5 as eluant, affording 1.2 g of the title compound.

1H-NMR (400 MHz), δ (ppm, DMSO-$d_6$): 7.95 (m, 1H), 7.85 (m, 1H), 7.77 (m, 1H), 3.86 (s, 3H), 3.59 (bs, 2H), 2.36 (m, 4H), 1.53 (m, 4H), 1.41 (m, 2H).

Operating in an analogous way, the following compounds were obtained:

4-Dimethylaminomethyl-2-nitro-benzoic acid methyl ester

ESI (+) MS: m/z 239 (MH+).

Example 4

Preparation of 3-amino-isonicotinic acid methyl ester

A mixture of 3-amino-isonicotinic acid (613 mg, 4.44 mmol), methanol (15 mL) and thionyl chloride (0.7 mL, 8.88 mmol) was stirred at reflux for 3 days. The volatiles were removed under reduced pressure and the residue stirred with diethylether (20 mL) and saturated solution of sodium hydrogenocarbonate (40 mL). The phases were separated and the aqueous phase extracted with diethylether (2×20 mL). The combined organic phases were dried over sodium sulfate and evaporated to dryness affording 400 mg of the title compound.

1H-NMR (400 MHz), δ (ppm, DMSO-$d_6$): 8.26 (s, 1H), 7.76 (d, J=5.2 Hz, 1H), 7.48 (d, J=5.2 Hz, 1H), 6.69 (bs, 2H), 3.85 (s, 3H).

Example 5

Preparation of 4-fluoro-2-nitro-benzoic acid tert-butyl ester

A solution of 4-fluoro-2-nitro benzoic acid (10 g, 54 mmol), (Boc)$_2$O (2 eq., 23.6 g, 108 mmol) and 4-(N,N-dimethylamino)pyridine (0.3 eq., 1.98 g, 16.2 mmol) in tert-butanol (100 mL) and dichloromethane (100 mL) was stirred at room temperature for 20 hours. The reaction mixture was then diluted with ethyl acetate (500 mL), washed with 1N HCl (500 mL), water (500 mL), brine (500 mL), dried over sodium sulfate and evaporated to dryness. The title compound was obtained as pale yellow oil (quantitative) and it was used in the next step without any further purification.

1H-NMR (400 MHz), δ (ppm, DMSO-$d_6$): 8.04 (dd, J=8.47, 2.50 Hz, 1H) 7.95 (dd, J=8.66, 5.37 Hz, 1H) 7.71 (ddd, J=8.66, 8.17, 2.56 Hz, 1H) 1.51 (s, 9H).

Example 6

Preparation of 4-(4-methyl-piperazin-1-yl)-2-nitro-benzoic acid tert-butyl ester A solution of 4-fluoro-2-nitro-benzoic acid tert-butyl ester (13 g, 54 mmol) and N-methylpiperazine (17 mL) was stirred at room temperature for 6 hours. The reaction mixture was then diluted with water (800 mL) and maintained under magnetic stirring for 20 hours. The resulting solid was filtered, washed thoroughly with water and dried under vacuum at 40° C. The title compound was obtained as yellow solid (16.4 g, 94% yield) and it was used in the next step without any further purification.

1H-NMR (400 MHz), δ (ppm, DMSO-$d_6$): 7.69 (d, J=8.90 Hz, 1H) 7.29 (d, J=2.56 Hz, 1H), 7.15 (dd, J1=8.90 Hz, J2=2.56 Hz, 1H), 3.37 (m, 4H), 2.44 (m, 4H), 1.46 (s, 9H).

Operating in an analogous way, the following compounds were obtained:

4-[(2-Dimethylamino-ethyl)-methyl-amino]-2-nitro-benzoic acid tert-butyl ester

1H-NMR (400 MHz), δ (ppm, DMSO-$d_6$): 7.67 (d, J=8.9 Hz, 1H), 6.98 (d, J=2.6 Hz, 1H), 6.89 (dd, J1=8.9 Hz, J2=2.6 Hz, 1H), 3.54 (m, 2H), 3.02 (s, 3H), 2.40 (m, 2H), 2.19 (s, 6H), 1.46 (s, 9H).

4-[(2-Dimethylamino-ethyl)-ethyl-amino]-2-nitro-benzoic acid tert-butyl ester

1H-NMR (400 MHz), δ (ppm, DMSO-$d_6$): 7.66 (d, J=8.9 Hz, 1H), 6.95 (d, J=2.6 Hz, 1H), 6.85 (dd, J1=8.9 Hz, J2=2.6 Hz, 1H), 3.51-3.42 (m, 4H), 2.40 (m, 2H), 2.20 (s, 6H), 1.45 (s, 9H), 1.10 (t, J=6.9 Hz, 3H).

4-(4-Ethyl-[1,4]diazepan-1-yl)-2-nitro-benzoic acid tert-butyl ester

1H-NMR (400 MHz), δ (ppm, DMSO-$d_6$): 7.66 (d, J=9.0 Hz, 1H), 7.03 (d, J=2.7 Hz, 1H), 6.92 (dd, J1=9.0 Hz, J2=2.7 Hz, 1H), 3.59 (m, 2H), 3.54 (m, 2H), 2.68 (m, 2H), 2.52-2.44 (m, 4H), 1.84 (m, 2H), 1.45 (s, 9H), 0.97 (t, J=7.1 Hz, 3H).

4-(4-Dimethylamino-piperidin-1-yl)-2-nitro-benzoic acid tert-butyl ester

1H-NMR (400 MHz), δ (ppm, DMSO-$d_6$): 7.67 (d, J=9.0 Hz, 1H), 7.26 (d, J=2.6 Hz, 1H), 7.13 (dd, J1=9.0 Hz, J2=2.6 Hz, 1H), 3.96 (m, 2H), 2.93 (m, 2H), 2.36 (m, 1H), 2.20 (s, 6H), 1.82 (m, 2H), 1.46 (s, 9H), 1.40 (m, 2H).

4-[Methyl-(1-methyl-pyrrolidin-3-yl)-amino]-2-nitro-benzoic acid tert-butyl ester 1H-NMR (400 MHz), δ (ppm, DMSO-$d_6$): 7.65 (d, J=9.0 Hz, 1H), 7.08 (d, J=2.7 Hz, 1H), 6.96 (dd, J1=9.0 Hz, J2=2.7

Hz, 1H), 4.59 (m, 1H), 2.94 (s, 3H), 2.82 (m, 1H), 2.71 (m, 1H), 2.42 (m, 1H), 2.26 (s, 3H), 2.25-2.10 (m, 2H), 1.66 (m, 1H), 1.44 (s, 9H).

4-{[2-(Isopropyl-methyl-amino)-ethyl]-methyl-amino}-2-nitro-benzoic acid tert-butyl ester 1H-NMR (400 MHz), δ (ppm, DMSO-$d_6$): 7.65 (d, J=9.0 Hz, 1H), 6.96 (d, J=2.6 Hz, 1H), 6.86 (dd, J1=9.0 Hz, J2=2.6 Hz, 1H), 3.49 (m, 2H), 3.01 (s, 3H), 2.74 (m, 1H), 2.46 (m, 2H), 2.17 (s, 3H), 1.44 (s, 9H), 0.87 (d, J=6.6 Hz, 6H).

2-Nitro-4-(4-pyrrolidin-1-yl-piperidin-1-yl)-benzoic acid tert-butyl ester

1H-NMR (400 MHz), δ (ppm, DMSO-$d_6$): 7.66 (d, J=9.0 Hz, 1H), 7.25 (d, J=2.6 Hz, 1H), 7.12 (dd, J1=9.0 Hz, J2=2.6 Hz, 1H), 3.85 (m, 2H), 2.99 (m, 2H), 2.51 (m, 4H), 2.23 (m, 1H), 1.88 (m, 2H), 1.67 (m, 4H), 1.50-1.37 (m, 11H).

4-[(3-Dimethylamino-propyl)-methyl-amino]-2-nitro-benzoic acid tert-butyl ester

1H-NMR (400 MHz), δ (ppm, DMSO-$d_6$): 7.67 (d, J=9.0 Hz, 1H), 7.02 (d, J=2.6 Hz, 1H), 6.90 (dd, J1=9.0 Hz, J2=2.6 Hz, 1H), 3.46 (m, 2H), 3.00 (s, 3H), 2.22 (m, 2H), 2.14 (s, 6H), 1.65 (m, 2H), 1.45 (s, 9H).

4-[Methyl-(2-piperidin-1-yl-ethyl)-amino]-2-nitro-benzoic acid tert-butyl ester

1H-NMR (400 MHz), δ (ppm, DMSO-$d_6$): 7.66 (d, J=9.0 Hz, 1H), 7.00 (d, J=2.6 Hz, 1H), 6.88 (dd, J1=9.0 Hz, J2=2.6 Hz, 1H), 3.54 (m, 2H), 3.01 (s, 3H), 2.44-2.34 (m, 6H), 1.50-1.34 (m, 15H).

4-[Methyl-(2-morpholin-4-yl-ethyl)-amino]-2-nitro-benzoic acid tert-butyl ester

1H-NMR (400 MHz), δ (ppm, DMSO-$d_6$): 7.65 (d, J=9.0 Hz, 1H), 7.00 (d, J=2.6 Hz, 1H), 6.88 (dd, J1=9.0 Hz, J2=2.6 Hz, 1H), 3.58-3.50 (m, 6H), 3.01 (s, 3H), 2.47-2.38 (m, 6H), 1.44 (s, 9H).

4-(4-methyl-[1,4]diazepan-1-yl)-2-nitro-benzoic acid tert-butyl ester

1H-NMR (400 MHz), δ (ppm, DMSO-$d_6$): 7.64 (d, J=9.0 Hz, 1H), 7.03 (d, J=2.7 Hz, 1H), 6.91 (dd, J1=9.0 Hz, J2=2.7 Hz, 1H), 3.59 (m, 2H), 3.51 (m, 2H), 2.59 (m, 2H), 2.44 (m, 2H), 2.25 (s, 3H), 1.86 (m, 2H), 1.44 (s, 9H).

Example 7

Preparation of 4-(2-dimethylamino-ethoxy)-2-nitro-benzoic acid tert-butyl ester

To a solution of 2-dimethylaminoethanol (6.67 mL, 64.8 mmol) in anhydrous tetrahydrofuran (100 mL), at 0° C., potassium tert-butoxide (6.66 g, 59.4 mmol) was added. The mixture was stirred at 0° C. for 1 h, then 4-fluoro-2-nitro-benzoic acid tert-butyl ester (10 g, 41.5 mmol) in anhydrous tetrahydrofuran (50 mL) was added dropwise. After 2 hours at 0° C., the mixture was poured into water (1 L) and extracted with ethyl acetate (4×200 mL). The organic phase was washed with water, brine, dried over anhydrous sodium sulfate, filtered and evaporated to dryness. The crude was purified by flash chromatography, using dichloromethane-methanol-33% NH$_4$OH 9:1:0.01 as eluant, to give the title compound (4.53 g) as yellow oil.

1H-NMR (400 MHz), δ (ppm, DMSO-$d_6$): 7.81 (d, 1H), 7.52 (d, 1H), 7.31 (dd, 1H), 4.21 (t, 2H), 2.65 (t, 2H), 2.22 (s, 6H), 1.49 (s, 9H).

Operating in an analogous way, the following compounds were obtained:

2-Nitro-4-(2-pyrrolidin-1-yl-ethoxy)-benzoic acid tert-butyl ester

1H-NMR (400 MHz), δ (ppm, DMSO-$d_6$): 7.81 (d, J=8.8 Hz, 1H), 7.53 (d, J=2.6 Hz, 1H), 7.31 (dd, J1=8.8 Hz, J2=2.6 Hz, 1H), 4.24 (m, 2H), 2.85 (m, 2H), 2.56 (m, 4H), 1.71 (m, 4H), 1.49 (s, 9H).

4-(1-Methyl-piperidin-4-yloxy)-2-nitro-benzoic acid tert-butyl ester

1H-NMR (400 MHz), δ (ppm, DMSO-$d_6$): 7.79 (d, J=8.8 Hz, 1H), 7.53 (d, J=2.6 Hz, 1H), 7.31 (dd, J1=8.8 Hz, J2=2.6 Hz, 1H), 4.60 (m, 1H), 2.61 (m, 2H), 2.26-2.15 (m, 5H), 1.96 (m, 2H), 1.67 (m, 2H), 1.48 (s, 9H).

Example 8

Preparation of 4-(4-methyl-piperazin-1-yl)-2-nitro benzoic acid hydrochloride

A mixture of 4-(4-methyl-piperazin-1-yl)-2-nitro-benzoic acid tert-butyl ester (16.4 g, 51 mmol) and 37% HCl (100 mL) in 1,4-dioxane (200 mL) was stirred at room temperature for 4 hours. The resulting solid was filtered, washed thoroughly with 1,4-dioxane and dried under vacuum at 45° C. The title compound was obtained as a pale yellow solid (13.45 g, 87.5% yield), and it was used in the next step without any further purification.

1H-NMR (400 MHz), δ (ppm, DMSO-$d_6$): 10.27 (bs, 1H), 7.81 (d, J=8.90 Hz, 1H), 7.40 (d, J=2.69 Hz, 1H), 7.24 (dd, J1=8.90 Hz, J2=2.69 Hz, 1H), 4.13 (bs, 2H), 3.55-3.06 (bs, 6H), 2.83 (s, 3H).

Operating in an analogous way, the following compounds were obtained:

4-[(2-Dimethylamino-ethyl)-methyl-amino]-2-nitro-benzoic acid hydrochloride

1H-NMR (400 MHz), δ (ppm, DMSO-$d_6$): 10.14 (bs, 1H), 7.78 (d, J=8.9 Hz, 1H), 7.11 (d, J=2.6 Hz, 1H), 7.01 (dd, J1=8.9 Hz, J2=2.6 HZ, 1H), 3.83 (m, 2H), 3.24 (m, 2H), 3.05 (s, 3H), 2.83, 2.82 (2s, 6H).

4-[(2-Dimethylamino-ethyl)-ethyl-amino]-2-nitro-benzoic acid hydrochloride

1H-NMR (400 MHz), δ (ppm, DMSO-$d_6$): 13.03 (bs, 1H), 10.19 (bs, 1H), 7.76 (d, J=8.9 Hz, 1H), 7.10 (d, J=2.6 Hz, 1H), 7.01 (dd, J1=8.9 Hz, J2=2.6 Hz, 1H), 3.76 (m, 2H), 3.48 (m, 2H), 3.23 (m, 2H), 2.83 (d, J=5.0 Hz, 6H), 1.12 (t, J=6.9 Hz, 3H).

4-(4-Ethyl-[1,4]diazepan-1-yl)-2-nitro-benzoic acid hydrochloride

1H-NMR (400 MHz), δ (ppm, DMSO-$d_6$): 13.02 (bs, 1H), 9.86 (bs, 1H), 7.78 (d, J=8.9 Hz, 1H), 7.14 (d, J=2.6 Hz, 1H), 6.99 (dd, J1=8.9 HZ, J2=2.6 Hz, 1H), 4.01-3.72 (m, 2H), 3.64-3.43 (m, 4H), 3.24-3.03 (m, 4H), 2.19 (m, 2H), 1.24 (t, J=7.2 Hz, 3H).

4-(4-Dimethylamino-piperidin-1-yl)-2-nitro-benzoic acid hydrochloride

1H-NMR (400 MHz), δ (ppm, DMSO-$d_6$): 13.03 (bs, 1H), 10.19 (bs, 1H), 7.75 (d, J=8.9 Hz, 1H), 7.32 (d, J=2.6 Hz, 1H), 7.17 (dd, J1=8.9 Hz, J2=2.7 Hz, 1H), 4.14 (m, 2H), 3.39 (m, 1H), 2.92 (m, 2H), 2.72 (d, J=5.0 Hz, 6H), 2.08 (m, 2H), 1.62 (m, 2H).

4-[Methyl-(1-methyl-pyrrolidin-3-yl)-amino]-2-nitro-benzoic acid hydrochloride 1H-NMR (400 MHz), δ (ppm, DMSO-$d_6$): 12.97 (bs, 1H), 10.84, (bs, 1H), 7.77 (d, J1=8.9 Hz, 1H), 7.19 (d, J=2.3 Hz, 1H), 7.02 (d, J=8.9 Hz, 1H), 5.02 (m, 1H), 3.8-2.95 (m, 4H), 2.94 (s, 3H), 2.82 (d, J=4.7 Hz, 3H), 2.37-1.97 (m, 2H).

4-{[2-(Isopropyl-methyl-amino)-ethyl]-methyl-amino}-2-nitro-benzoic acid hydrochloride 1H-NMR (400 MHz), δ (ppm, DMSO-$d_6$): 13.05 (bs, 1H), 9.90 (bs, 1H), 7.78 (d, J=9.0 Hz, 1H), 7.12 (d, J=2.7 Hz, 1H), 7.03 (dd, J1=9.0 Hz, J2=2.7 Hz, 1H), 3.85 (m, 2H), 3.60 (m, 1H), 3.18 (m, 2H), 3.06 (s, 3H), 2.72 (s, 3H), 1.25 (bs, 6H).

2-Nitro-4-(4-pyrrolidin-1-yl-piperidin-1-yl)-benzoic acid hydrochloride

1H-NMR (400 MHz), δ (ppm, DMSO-$d_6$): 13.07 (bs, 1H), 10.31 (bs, 1H), 7.77 (d, J=9.0 Hz, 1H), 7.34 (d, J=2.2 Hz, 1H), 7.19 (dd, J1=9.0 Hz, J2=2.2 Hz, 1H), 4.12 (m, 2H), 3.56-3.26 (m, 3H), 3.08 (m, 2H), 2.93 (m, 2H), 2.12 (m, 2H), 2.00 (m, 2H), 1.86 (m, 2H), 1.67 (m, 2H).

4-[(3-Dimethylamino-propyl)-methyl-amino]-2-nitro-benzoic acid hydrochloride 1H-NMR (400 MHz), δ (ppm, DMSO-$d_6$): 13.07 (bs, 1H), 9.72 (bs, 1H), 7.76 (d, J=9.0 Hz, 1H), 7.03 (d, J=2.6 Hz, 1H), 6.93 (dd, J1=9.0 Hz, J2=2.6 Hz, 1H), 3.51 (m, 2H), 3.08 (m, 2H), 3.03 (s, 3H), 2.77 (s, 6H), 1.90 (m, 2H).

4-[Methyl-(2-piperidin-1-yl-ethyl)-amino]-2-nitro-benzoic acid hydrochloride 1H-NMR (400 MHz), δ (ppm, DMSO-$d_6$): 13.03 (bs, 1H), 9.85 (bs, 1H), 7.76 (d, J=9.0 Hz, 1H), 7.09 (d, J=2.6 Hz, 1H), 7.00 (dd, J1=9.0 Hz, J2=2.6 Hz, 1H), 3.84 (m, 2H), 3.47 (m, 2H), 3.19 (m, 2H), 3.03 (s, 3H), 2.92 (m, 2H), 1.87-1.63 (m, 5H), 1.38 (m, 1H).

2-Nitro-4-(2-pyrrolidin-1-yl-ethoxy)-benzoic acid hydrochloride

1H-NMR (400 MHz), δ (ppm, DMSO-$d_6$): 13.39 (bs, 1H), 10.14 (bs, 1H), 7.93 (d, J=8.7 Hz, 1H), 7.58 (d, J=2.6 Hz, 1H), 7.37 (dd, J1=8.7 Hz, J2=2.6 Hz, 1H), 4.49 (m, 2H), 3.7-3.55 (m, 4H), 3.13 (m, 2H), 2.03 (m, 2H), 1.90 (m, 2H).

4-[Methyl-(2-morpholin-4-yl-ethyl)-amino]-2-nitro-benzoic acid hydrochloride ESI (+) MS: m/z 310 (MH$^+$).

4-(2-Dimethylamino-ethoxy)-2-nitro-benzoic acid hydrochloride

1H-NMR (400 MHz), δ (ppm, DMSO-$d_6$): 9.92 (bs, 1H), 7.93 (d, J=8.7 Hz, 1H), 7.57 (d, J=2.5 Hz, 1H), 7.37 (dd, J1=8.7 Hz, J2=2.5 Hz, 1H), 4.50 (m, 2H), 3.55 (m, 2H), 2.87 (s, 6H).

4-(1-Methyl-piperidin-4-yloxy)-2-nitro-benzoic acid hydrochloride

1H-NMR (400 MHz), δ (ppm, DMSO-$d_6$): 13.52 (bs, 1H), 9.95 (bs, 1H), 7.89 (m, 1H), 7.58 (m, 1H), 7.36 (m, 1H), 4.95 (m, 1H), 3.56-3.02 (m, 4H), 2.80 (s, 3H), 2.37-1.78 (m, 4H).

4-(4-Methyl-[1,4]diazepan-1-yl)-2-nitro-benzoic acid hydrochloride

1H-NMR (400 MHz), δ (ppm, DMSO-$d_6$): 13.05 (bs, 1H), 10.06 (bs, 1H), 7.79 (d, J=8.9 Hz, 1H), 7.16 (d, J=2.6 Hz, 1H), 6.99 (dd, J1=8.9 HZ, J2=2.6 Hz, 1H), 4.0-3.7 (m, 2H), 3.6-3.4 (m, 4H), 3.25-3.0 (m, 2H), 2.83 (s, 3H), 2.19 (m, 2H).

Example 9

Preparation of 2-amino-4-(4-methyl-piperazin-1-yl)-benzoic acid tert-butyl ester A mixture of 4-(4-methyl-piperazin-1-yl)-2-nitro-benzoic acid tert-butyl ester (13.3 g, 41.5 mmol) cyclohexene (45 mL), ethanol (300 mL) and 10% Pd/C (0.4 g) was stirred at 80° C. for 7 hours. Additional 10% Pd/C was added (0.9 g) and the mixture stirred at 80° C. for additional 4 hours. The reaction mixture was filtered over a celite pad washing thoroughly with ethanol and the filtrate was evaporated to dryness affording the title compound as a pale yellow solid (11.5 g, 95% yield).

1H-NMR (400 MHz), δ (ppm, DMSO-$d_6$): 7.47 (d, J=9.0 Hz, 1H), 6.40 (bs, 2H), 6.18 (dd, J1=9.0 Hz, J2=2.4 Hz, 1H), 6.11 (d, J=2.4 Hz, 1H), 3.16 (m, 4H), 2.41 (m, 4H), 2.21 (s, 3H), 1.49 (s, 9H).

Operating in an analogous way, the following compounds were obtained:

2-Amino-4-[(2-dimethylamino-ethyl)-methyl-amino]-benzoic acid tert-butyl ester ESI (+) MS: m/z 294 (MH$^+$).

2-Amino-4-piperidin-1-ylmethyl-benzoic acid methyl ester

1H-NMR (400 MHz), δ (ppm, DMSO-$d_6$): 7.62 (bd, J=8.3 Hz, 1H), 6.72 (m, 1H), 6.60 (bs, 2H), 6.47 (bd, J=8.3 Hz, 1H), 3.76 (s, 3H), 3.30 (s, 2H), 2.30 (m, 4H), 1.49 (m, 4H), 1.38 (m, 2H).

2-Amino-4-(4-pyrrolidin-1-yl-piperidin-1-yl)-benzoic acid tert-butyl ester

1H-NMR (400 MHz), δ (ppm, DMSO-$d_6$): 7.46 (d, J=9.0 Hz, 1H), 6.39 (bs, 2H), 6.18 (dd, J1=9.1 Hz, J2=2.3 Hz, 1H), 6.12 (d, J=2.3 Hz, 1H), 3.69 (m, 2H), 2.79 (m, 2H), 2.65-2.5 (m, 5H), 1.88 (m, 2H), 1.71 (m, 4H), 1.49 (s, 9H), 1.44 (m, 2H).

2-Amino-4-[(3-dimethylamino-propyl)-methyl-amino]-benzoic acid tert-butyl ester 1H-NMR (400 MHz), δ (ppm, DMSO-$d_6$): 7.45 (d, J=9.0 Hz, 1H), 6.36 (bs, 2H), 5.99 (dd, J1=9.0 Hz, J2=2.6 Hz, 1H), 5.86 (d, J=2.6 Hz, 1H), 3.31 (m, 2H), 2.87 (s, 3H), 2.22 (m, 2H), 2.15 (s, 6H), 1.62 (m, 2H), 1.48 (s, 9H).

Example 10

Preparation of 4-(4-methyl-piperazin-1-yl)-2-(tetrahydro-pyran-4-ylamino)-benzoic acid tert-butyl ester To a solution of 2-amino-4-(4-methyl-piperazin-1-yl)-benzoic acid tert-butyl ester (11.5 g, 39.5 mmol) in dichloromethane (340 mL) were added tetrahydro-pyran-4-one (4.5 mL, 49.3 mmol), trifluoroacetic acid (8.2 mL) and tetramethylammonium triacetoxyborohydride (15.57 g, 59.2 mmol). The mixture was stirred at room temperature for 2 hours then washed with 0.5N hydrochloric acid, with 0.5N NaOH and with a saturated solution of $NaHCO_3$. The organic layer was dried over sodium sulfate and evaporated to dryness affording the title compound as a pale yellow solid (13.3 g, 90% yield).

1H-NMR (400 MHz), δ (ppm, DMSO-$d_6$): 7.72 (d, J=7.7 Hz, 1H), 7.58 (d, J=9.1 Hz, 1H), 6.20 (dd, J1=9.1 Hz, J2=2.2 Hz, 1H), 6.08 (d, J=2.2 Hz, 1H), 3.85 (m, 2H), 3.70 (m, 1H), 3.50 (m, 2H), 3.27 (m, 4H), 2.47 (m, 4H), 2.26 (bt, 3H), 1.96 (m, 2H), 1.51 (s, 9H), 1.39 (m, 2H).

Operating in an analogous way, the following compounds were obtained:

4-Nitro-2-(tetrahydro-pyran-4-ylamino)-benzoic acid ethyl ester

1H-NMR (400 MHz), δ (ppm, DMSO-$d_6$): 8.05 (d, J=8.8 Hz, 1H), 7.92 (bd, 1H), 7.56 (d, J=2.2 Hz, 1H), 7.34 (dd, J=7.33 Hz, 1H), 4.33 (q, J=7.0 Hz, 2H), 3.85 (m, 3H), 3.53 (m, 2H), 1.97 (m, 2H), 1.47 (m, 2H), 1.33 (t, J=7.0 Hz, 3H).

4-[(2-Dimethylamino-ethyl)-methyl-amino]-2-(tetrahydro-pyran-4-ylamino)-benzoic acid tert-butyl ester ESI (+) MS: m/z 378 (MH$^+$).

4-Piperidin-1-ylmethyl-2-(tetrahydro-pyran-4-ylamino)-benzoic acid methyl ester 1H-NMR (400 MHz), δ (ppm, DMSO-$d_6$): 7.92-7.60 (m, 2H), 7.03-6.48 (m, 2H), 3.85 (m, 2H), 3.80 (bs, 3H), 3.30 (m, 2H), 3.67 (m, 1H), 3.49 (m, 2H), 2.31 (4H), 1.97 (m, 2H), 1.85-1.30 (m, 8H).

4-(4-Pyrrolidin-1-yl-piperidin-1-yl)-2-(tetrahydro-pyran-4-ylamino)-benzoic acid tert-butyl ester trifluoroacetate 1H-NMR (400 MHz), δ (ppm, DMSO-$d_6$): 9.95 (bs, 1H), 7.72 (bd, J=7.7 Hz, 1H), 7.59 (d, J=9.0 Hz, 1H), 6.23 (dd, J1=9.0 Hz, J2=2.3 Hz, 1H), 6.10 (d, J=2.3 Hz, 1H), 3.97 (m, 2H), 3.85 (m, 2H), 3.70 (m, 1H), 3.50 (m, 4H), 3.30 (m, 1H), 3.07 (m, 2H), 2.80 (m, 2H), 2.12-1.79 (m, 8H), 1.64 (m, 2H), 1.51 (s, 9H), 1.40 (m, 2H).

4-[(3-Dimethylamino-propyl)-methyl-amino]-2-(tetrahydro-pyran-4-ylamino)-benzoic acid tert-butyl ester 1H-NMR (400 MHz), δ (ppm, DMSO-$d_6$): 7.70 (bd, J=7.4 Hz, 1H), 7.54 (d, J=9.0 Hz, 1H), 5.99 (dd, J1=9.0 Hz, J2=2.3 Hz, 1H), 5.79 (d, J=2.3 Hz, 1H), 3.86 (m, 2H), 3.62 (m, 1H), 3.47 (m, 2H), 3.36 (m, 2H), 2.93 (s, 3H), 2.28 (m, 2H), 2.18 (bs, 6H), 1.97 (m, 2H), 1.64 (m, 2H), 1.49 (s, 9H), 1.39 (m, 2H).

3-(Tetrahydro-pyran-4-ylamino)-isonicotinic acid methyl ester

1H-NMR (400 MHz), δ (ppm, DMSO-$d_6$): 8.41 (s, 1H), 7.84 (d, J=5.1 Hz, 1H), 7.57 (d, J=5.1 Hz, 1H), 7.29 (bd, J=7.9 Hz, 1H), 3.89-3.82 (m, 3H), 3.84 (s, 3H), 3.48 (m, 2H), 1.96 (m, 2H), 1.44 (m, 2H).

3-(2-Methoxy-1-methyl-ethylamino)-isonicotinic acid methyl ester

1H-NMR (400 MHz), δ (ppm, DMSO-$d_6$): 8.36 (s, 1H), 7.82 (d, J=5.1 Hz, 1H), 7.56 (d, J=5.1 Hz, 1H), 7.43 (bd, J=8.4 Hz, 1H), 4.02 (m, 1H), 3.84 (s, 3H), 3.43 (m, 2H), 3.31 (s, 3H), 1.19 (d, J=6.5 Hz, 3H).

Example 11

Preparation of 4-nitro-2-(tetrahydro-pyran-4-ylamino)-benzoic acid

4-Nitro-2-(tetrahydro-pyran-4-ylamino)-benzoic acid ethyl ester (11.2 g, 38 mmol) was dissolved in 200 mL of ethanol at 60° C. then 2N NaOH was added (40 mL, 80 mmol). The mixture was stirred at 60° C. for 4 hours, then the solvent removed under reduced pressure. The residue was taken-up with 200 mL of water and the mixture brought to acidic pH with 2N HCl (35 mL). The precipitated yellow solid was filtered, washed with plenty of water and dried in oven at 40° C. affording the title compound (9.3 g).

1H-NMR (400 MHz), δ (ppm, DMSO-$d_6$): 13.49 (bs, 1H), 8.17 (bd, 1H), 8.04 (d, J=8.7 Hz, 1H), 7.54 (d, J=2.2 Hz, 1H), 7.32 (dd, J1=8.7 HZ, J2=2.2 Hz, 1H), 3.90-3.78 (m, 3H), 3.54 (m, 2H), 1.98 (m, 2H), 1.46 (m, 2H).

Operating in an analogous way, the following compounds were obtained:

4-Piperidin-1-ylmethyl-2-(tetrahydro-pyran-4-ylamino)-benzoic acid hydrochloride 1H-NMR (400 MHz), δ (ppm, DMSO-$d_6$): 12.60 (bs, 1H), 10.71 (bs, 1H), 7.91 (bs, 1H), 7.80 (d, J=7.9 Hz, 1H), 7.15 (m, 1H), 6.66 (m, 1H), 4.04 (bs, 2H), 3.88 (m, 2H), 3.73 (m, 1H), 3.50 (m, 2H), 3.0-2.6 (m, 4H), 2.00 (m, 2H), 1.9-1.6 (m, 6H), 1.41 (m, 2H).

4-Dimethylaminomethyl-2-nitro-benzoic acid

1H-NMR (400 MHz), δ (ppm, DMSO-$d_6$): 7.84 (m, 1H), 7.79 (d, J=7.9 Hz, 1H), 7.69 (bd, J=7.9 Hz, 1H), 3.66 (bs, 2H), 2.27 (s, 6H).

3-(Tetrahydro-pyran-4-ylamino)-isonicotinic acid

1H-NMR (400 MHz), δ (ppm, DMSO-d$_6$): 13.30 (bs, 1H), 8.37 (s, 1H), 7.84 (d, J=5.1 Hz, 1H), 7.58 (d, J=5.1 Hz, 1H), 7.52 (bs, 1H), 3.91-3.79 (m, 3H), 3.50 (m, 2H), 1.98 (m, 2H), 1.43 (m, 2H).

3-(2-Methoxy-1-methyl-ethylamino)-isonicotinic acid

1H-NMR (400 MHz), δ (ppm, DMSO-d$_6$): 8.33 (s, 1H), 7.83 (d, J=5.1 Hz, 1H), 7.60 (d, J=5.1 Hz, 1H), 7.58 (bs, 1H), 3.99 (m, 1H), 3.41 (m, 2H), 3.30 (s, 3H), 1.18 (d, J=6.5 Hz, 3H).

Example 12

Preparation of 4-(4-methyl-piperazin-1-yl)-2-[(tetrahydro-pyran-4-yl)-(2,2,2-trifluoro-acetyl)-amino]-benzoic acid tert-butyl ester To a solution of 4-(4-methyl-piperazin-1-yl)-2-(tetrahydro-pyran-4-ylamino)-benzoic acid tert-butyl ester (13.3 g, 35.4 mmol) in dry dichloromethane (350 mL), under argon, at 0° C., were added triethylamine (7.5 mL, 53.1 mmol) and trifluoroacetic anhydride (6.5 mL, 46.1 mmol). The mixture was stirred at 0° C. for 20 minutes, then water (350 mL) was added dropwise. The phases were separated and the organic phase washed with brine, dried over sodium sulfate and evaporated to dryness. The crude residue was purified by chromatography on silica gel using dichloromethane/ethanol 95:5 as the eluant, affording 12.1 g of the title compound as a pale yellow solid (73% yield).

1H-NMR (400 MHz), δ (ppm, DMSO-d$_6$): 7.83 (d, J=9.0 Hz, 1H), 7.06 (dd, J1=9.0 Hz, J2=2.5 Hz, 1H), 6.82 (J=2.5 Hz, 1H), 4.48 (m, 1H), 3.85 (m, 2H), 3.5-3.3 (m, 6H), 2.49 (m, 4H), 2.26 (bs, 3H), 2.0 (m, 1H), 1.59 (m, 1H), 1.51 (m, 1H), 1.46 (s, 9H), 1.03 (m, 1H).

Operating in an analogous way, the following compounds were obtained:

4-[(2-Dimethylamino-ethyl)-methyl-amino]-2-[(tetrahydro-pyran-4-yl)-(2,2,2-trifluoro-acetyl)-amino]-benzoic acid tert-butyl ester 1H-NMR (400 MHz), δ (ppm, DMSO-d$_6$): 7.80 (d, J=9.1 Hz, 1H), 6.79 (dd, J1=9.1 Hz, J2=2.6 Hz, 1H), 6.51 (d, J=2.6 Hz, 1H), 4.48 (m, 1H), 3.86 (m, 1H), 3.79 (m, 1H), 3.52 (m, 2H), 3.41-3.25 (m, 2H), 3.00 (s, 3H), 2.5-2.35 (m, 2H), 2.21 (s, 6H), 1.98 (m, 1H), 1.64-1.45 (m, 3H), 1.44 (s, 9H).

4-(4-Pyrrolidin-1-yl-piperidin-1-yl)-2-[(tetrahydro-pyran-4-yl)-(2,2,2-trifluoro-acetyl)-amino]-benzoic acid tert-butyl ester ESI (+) MS: m/z 526 (MH$^+$).

4-[(3-Dimethylamino-propyl)-methyl-amino]-2-[(tetrahydro-pyran-4-yl)-(2,2,2-trifluoro-acetyl)-amino]-benzoic acid tert-butyl ester 1H-NMR (400 MHz), δ (ppm, DMSO-d$_6$): 7.79 (d, J=9.1 Hz, 1H), 6.79 (dd, J1=9.1 Hz, J2=2.6 Hz, 1H), 6.52 (d, J=2.6 Hz, 1H), 4.48 (m, 1H), 3.87 (m, 1H), 3.79 (m, 1H), 3.51-3.32 (m, 4H), 2.98 (s, 3H), 2.22 (m, 2H), 2.12 (s, 6H), 1.99 (m, 1H), 1.70-1.46 (m, 4H), 1.44 (s, 9H), 1.03 (m, 1H).

Example 13

Preparation of 4-nitro-2-[(tetrahydro-pyran-4-yl)-(2,2,2-trifluoro-acetyl)-amino]-benzoic acid To 30 mL of trifluoroacetic anhydride was added 4-nitro-2-(tetrahydro-pyran-4-ylamino)-benzoic acid (9.1 g, 34.2 mmol) in small portions, at room temperature. The mixture was stirred at room temperature for 1 hour then evaporated to dryness. The residue (brown oil) was treated with 200 mL of water and vigorously stirred for 3 hours at room temperature. The white solid thus formed was filtered, washed with plenty of water and dried in oven at 40° C. affording the title compound (11.8 g).

1H-NMR (400 MHz), δ (ppm, DMSO-d$_6$): 13.52 (bs, 1H), 8.45 (dd, J1=8.5 Hz, J2=2.3 Hz, 1H), 8.32 (d, J=2.3 Hz, 1H), 8.26 (d, J=8.5 Hz, 1H), 4.58 (m, 1H), 3.84 (m, 2H), 3.45-3.2 (m, 2H), 1.98 (m, 1H), 1.59 (m, 1H), 1.49 (m, 1H), 1.14 (m, 1H).

Operating in an analogous way, the following compounds were obtained:

4-Piperidin-1-ylmethyl-2-[(tetrahydro-pyran-4-yl)-(2,2,2-trifluoro-acetyl)-amino]-benzoic acid trifluoroacetate ESI (+) MS: m/z 415 (MH$^+$).

3-[(Tetrahydro-pyran-4-yl)-(2,2,2-trifluoro-acetyl)-amino]-isonicotinic acid

1H-NMR (400 MHz), δ (ppm, DMSO-d$_6$): 8.88 (d, J=5.0 Hz, 1H), 8.77 (s, 1H), 7.94 (d, J=5.0 Hz, 1H), 4.57 (m, 1H), 3.84 (m, 2H), 3.41 (m, 2H), 1.95 (m, 1H), 1.60 (m, 1H), 1.47 (m, 1H), 1.08 (m, 1H).

3-[(2-Methoxy-1-methyl-ethyl)-(2,2,2-trifluoro-acetyl)-amino]-isonicotinic acid

1H-NMR (400 MHz), δ (ppm, DMSO-d$_6$): 8.84, 8.80 (2d, J=5.0 Hz, 1H), 8.69, 8.62 (2s, 1H), 7.90, 7.84 (2d J=5.0 Hz, 1H), 4.82, 4.54 (2m, 1H), 3.47-3.11 (m, 5H), 1.17, 0.87 (2d, J=7.0 Hz, 3H), mixture of rotamers.

Example 14

Preparation of 4-(4-methyl-piperazin-1-yl)-2-[(tetrahydro-pyran-4-yl)-(2,2,2-trifluoro-acetyl)-amino]-benzoic acid trifluoroacetate A mixture of 4-(4-methyl-piperazin-1-yl)-2-[(tetrahydro-pyran-4-yl)-(2,2,2-trifluoro-acetyl)-amino]-benzoic acid tert-butyl ester (12.1 g, 25.7 mmol), trifluoroacetic acid (48.5 mL) and dichloromethane (195 mL) was stirred at room temperature for 2 hours. The volatiles were then evaporated, the residue taken up with diethylether and evaporated again. The procedure was repeated 5 times, then the solid was triturated with diethylether, filtered and dried in oven at 40° C. affording the title compound as a pale brown solid (13.4 g).

1H-NMR (400 MHz), δ (ppm, DMSO-d$_6$): 12.78 (bs, 1H), 9.74 (bs, 1H), 7.93 (d, J=8.8 Hz, 1H), 7.13 (dd, J1=8.8 Hz, J2=2.5 Hz, 1H), 6.98 (d, J=2.5 Hz, 1H), 4.49 (m, 1H), 4.11 (m, 2H), 3.84 (m, 2H), 3.6-3.0 (m, 8H), 2.89 (s, 3H), 1.98 (m, 1H), 1.59 (m, 1H), 1.53 (m, 1H), 1.08 (m, 1H).

Operating in an analogous way, the following compounds were obtained:

4-[(2-Dimethylamino-ethyl)-methyl-amino]-2-[(tetrahydro-pyran-4-yl)-(2,2,2-trifluoro-acetyl)-amino]-benzoic acid trifluoroacetate 1H-NMR (400 MHz), δ (ppm, DMSO-$d_6$): 12.56 (bs, 1H), 9.49 (bs, 1H), 7.88 (d, J=8.9 Hz, 1H), 8.92 (dd, J1=8.9 Hz, J2=2.6 Hz, 1H), 6.63 (d, J=2.6 Hz, 1H), 4.49 (m, 1H), 3.9-3.2 (m, 8H), 3.02 (s, 3H), 2.85 (s, 6H), 1.98 (m, 1H), 1.62-1.49 (m, 2H), 1.08 (m, 1H).

4-(4-Pyrrolidin-1-yl-piperidin-1-yl)-2-[(tetrahydro-pyran-4-yl)-(2,2,2-trifluoro-acetyl)-amino]-benzoic acid trifluoroacetate ESI (+) MS: m/z 470 (MH$^+$).

4-[(3-Dimethylamino-propyl)-methyl-amino]-2-[(tetrahydro-pyran-4-yl)-(2,2,2-trifluoro-acetyl)-amino]-benzoic acid trifluoroacetate ESI (+) MS: m/z 432 (MH$^+$).

Example 15

Preparation of 2,4-difluoro-benzoic acid tert-butyl ester

To a solution of 2,4-difluorobenzoic acid (5 g, 31.62 mmol) in a mixture of dichloromethane (100 mL) and t-BuOH (50 mL) were added (BOC)$_2$O (13.8 g, 63.24 mmol) and N,N-dimethylaminopyridine (1.16 g, 9.49 mmol). The solution was stirred at room temperature for 24 hours then diluted with dichloromethane and washed twice with 1N HCl, NaHCO$_3$ saturated solution, water (3 times) and brine. The organic phase was dried over sodium sulfate, filtered and evaporated to give the title compound (5.70 g, 84%) as yellowish oil.

1H-NMR (400 MHz), δ (ppm, DMSO-$d_6$): 7.91 (m, 1H), 7.36 (m, 1H), 7.20 (m, 1H), 1.53 (s, 9H).

Example 16

Preparation of 4-fluoro-2-((S)-2-methoxy-1-methyl-ethylamino)-benzoic acid tert-butyl ester A mixture of 2,4-difluoro-benzoic acid tert-butyl ester (30 g, 140.05 mmol) and (S)-2-methoxy-1-methyl-ethylamine (100 mL) was stirred at 65° C. for 2 days. A saturated solution of NaHCO$_3$ was added and the mixture was extracted with dichloromethane (3 times). The organic phase was washed twice with water then with brine, dried over sodium sulfate filtered and evaporated to dryness to obtain a crude, which was purified by column chromatography on silica gel eluting with exane/ethyl acetate 9:1. The title compound (33.38 g, 84%) was obtained as oil.

1H-NMR (400 MHz), δ (ppm, DMSO-$d_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

Operating in a way analogous to that described above, the following compounds were obtained:

4-Fluoro-2-((R)-2-methoxy-1-methyl-ethylamino)-benzoic acid tert-butyl ester

1H-NMR (400 MHz), δ (ppm, DMSO-$d_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

4-Fluoro-2-(2-methoxy-ethylamino)-benzoic acid tert-butyl ester

1H-NMR (400 MHz), δ (ppm, DMSO-$d_6$): 7.89 (t, J=5.00 Hz, 1H), 7.80 (t, J=7.07 Hz, 1H), 6.56 (dd, J1=12.80 Hz, J2=2.56 Hz, 1H), 6.37 (m, 1H), 3.55 (t, J=5.37 Hz, 2H), 3.33 (m, 2H), 3.29 (s, 3H), 1.53 (s, 9H).

Example 17

Preparation of 4-fluoro-2-[((S)-2-methoxy-1-methyl-ethyl)-(2,2,2-trifluoro-acetyl)-amino]-benzoic acid tert-butyl ester A solution of 4-fluoro-2-((S)-2-methoxy-1-methyl-ethylamino)-benzoic acid tert-butyl ester (1.54 g, 5.44 mmol) in dichloromethane (30 mL) was cooled to 0°-5° C. Triethylamine (1.11 mL, 8.16 mmol) and trifluoroacetic anhydride (1.15 mL, 8.16 mmol) were added. After 3 hours at 0°-5° C. the mixture was washed with NaHCO$_3$ saturated solution, water and brine. The organic layer was dried over sodium sulfate, filtered and evaporated to give the title compound as yellowish oil (2 g, 99%).

1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

Operating in a way analogous to that described above, the following compounds were obtained:

4-Fluoro-2-[((R)-2-methoxy-1-methyl-ethyl)-(2,2,2-trifluoro-acetyl)-amino]-benzoic acid tert-butyl ester 1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

4-Fluoro-2-[(2-methoxy-ethyl)-(2,2,2-trifluoro-acetyl)-amino]-benzoic acid tert-butyl ester 1H-NMR (400 MHz), δ (ppm, DMSO-$d_6$): 8.07 (m, 1H), 7.50 (m, 1H), 7.41 (dd, J1=9.39 Hz, J2=2.56 Hz, 1H), 4.28 (m, 1H), 3.55 (m, 1H), 3.46 (m, 1H), 3.38 (m, 1H), 3.18 (s, 3H), 1.49 (s, 9H).

Example 18

Preparation of 2-[((S)-2-methoxy-1-methyl-ethyl)-(2,2,2-trifluoro-acetyl)-amino]-4-(4-methyl-piperazin-1-yl)-benzoic acid tert-butyl ester A solution of 4-fluoro-2-[((S)-2-methoxy-1-methyl-ethyl)-(2,2,2-trifluoro-acetyl)-amino]-benzoic acid tert-butyl ester (2 g, 5.28 mmol) and N-methylpiperazine (5.86 mL, 52.8 mmol) in tetrahydrofuran (20 mL) was stirred at 60° C. for 7 days. The solution was then evaporated, NaHCO$_3$ saturated solution was added and the mixture extracted with dichloromethane (3 times). The organic layer was washed with water, brine, dried over sodium sulfate, filtered and evaporated to obtain a crude, which was purified by column chromatography on silica gel (dichloromethane-methanol 93:7). The title compound (2.04 g, 84%) was obtained as yellowish solid.

1H-NMR (400 MHz), δ (ppm, DMSO-d$_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

Operating in a way analogous to that described above, the following compounds were obtained:

2-[((R)-2-Methoxy-1-methyl-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-d$_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

2-[(2-Methoxy-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-d$_6$): (mixture of tautomers) 7.83 (d, J=9.02 Hz, 1H), 7.05 (dd, J1=9.02 Hz, J2=2.68 Hz, 1H), 6.86 (d, J=2.68 Hz, 1H), 4.31 (m, 1H), 3.55 (m, 1H), 3.40 (m, 1H), 3.32 (m, 4H), 3.25 (m, 1H), 3.21 (s, 1H), 2.44 (t, J=5.12 Hz, 4H), 2.22 (bs, 3H), 1.46 (s, 9H).

4-[(2-Dimethylamino-ethyl)-methyl-amino]-2-[(2-methoxy-ethyl)-(2,2,2-trifluoro-acetyl)-amino]-benzoic acid tert-butyl ester 1H-NMR (400 MHz), δ (ppm, DMSO-d$_6$): 7.81 (d, J=8.9 Hz, 1H), 6.78 (dd, J1=8.9 Hz, J2=2.8 Hz, 1H), 6.60 (d, J=2.8 Hz, 1H), 4.40-4.31 (m, 1H), 3.59-3.39 (m, 4H), 3.23 (s, 3H), 3.22-3.15 (m, 1H), 3.00 (s, 3H), 2.40 (m, 2H), 2.19 (bs, 6H), 1.46 (s, 9H).

Example 19

Preparation of 2-[((S)-2-methoxy-1-methyl-ethyl)-(2,2,2-trifluoro-acetyl)-amino]-4-(4-methyl-piperazin-1-yl)-benzoic acid trifluoroacetate To a solution of 2-[((S)-2-methoxy-1-methyl-ethyl)-(2,2,2-trifluoro-acetyl)-amino]-4-(4-methyl-piperazin-1-yl)-benzoic acid tert-butyl ester (2.03 g, 4.42 mmol) in dichloromethane (15 mL) trifluoroacetic acid (3.4 mL, 44.2 mmol) was added. The mixture was stirred at room temperature for 15 hours then the solution was evaporated to dryness affording the title compound as oil that was used for the next step without any further purification.

1H-NMR (400 MHz), δ (ppm, DMSO-d$_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

Operating in a way analogous to that described above, the following compounds were obtained:

2-[((R)-2-Methoxy-1-methyl-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-d$_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

2-[(2-Methoxy-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-d$_6$): (mixture of tautomers) 12.76 (bs, 1H), 9.73 (bs, 1H), 7.91 (d, J=8.78 Hz, 1H), 7.10 (dd, J1=8.78 Hz, J2=2.68 Hz, 1H), 7.01 (d, J=2.68 Hz, 1H), 4.15 (m, 1H), 4.04 (m, 2H), 3.54 (m, 2H), 3.42 (m, 2H), 3.38 (m, 2H), 3.33 (m, 2H), 3.19 (s, 3H), 3.14 (m, 2H), 2.86 (bs, 3H).

4-[(2-Dimethylamino-ethyl)-methyl-amino]-2-[(2-methoxy-ethyl)-(2,2,2-trifluoro-acetyl)-amino]-benzoic acid hydrochloride 1H-NMR (400 MHz), δ (ppm, DMSO-d$_6$): 12.59 (bs, 1H), 10.00 (bs, 1H), 7.88 (d, J=8.9 Hz, 1H), 6.92 (dd, J1=8.9 Hz, J2=2.8 Hz, 1H), 6.74 (8d, J=2.8 Hz, 1H), 4.18 (m, 1H), 3.79 (m, 2H), 3.56 (m, 1H), 3.47-3.36 (m, 2H), 3.24 (m, 2H), 3.21 (s, 3H), 3.01 (s, 3H), 2.84 (bd, 6H).

Example 20

Preparation of N-(5-benzenesulfonyl-1H-indazol-3-yl)-4-(4-methyl-piperazin-1-yl)-2-nitro-benzamide [(I), R1=R2=R3=H, R=phenyl, Ar=4-(4-methyl-piperazin-1-yl)-2-nitro-phenyl], cpd. 4

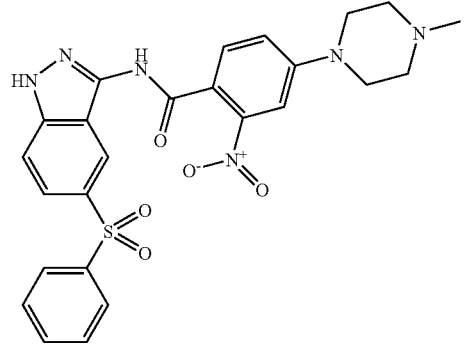

4-(4-Methyl-piperazin-1-yl)-2-nitro-benzoic acid (5.54 g, 18.37 mmol) in dry tetrahydrofuran (100 mL) was treated with 0.070 mL of N,N-dimethylformamide followed by neat thionyl chloride (5.5 mL, 76.43 mmol) and refluxed for three hours. The volatiles were then removed by evaporation under reduced pressure and the solid was repeatedly taken up with anhydrous toluene (100 mL×3) and evaporated. The crude yellow acid chloride thus obtained was thoroughly dried under vacuum at room temperature then suspended in dry tetrahydrofuran (100 mL) and treated with a suspension of 5-benzenesulfonyl-indazol-3-ylamine (2.11 g, 7.71 mmol) and N,N-diisopropylethylamine (6.3 mL, 36.74 mmol). The reaction mixture was stirred at 60° C. (oil bath temperature) for 22 hours. The resulting almost clear solution was cooled to room temperature and the volatiles were removed by evaporation. The residue was treated with tetrahydrofuran (100 mL), methanol (100 mL) and 2N NaOH (30 mL). After stirring at room temperature for two hours, the organic solvents were removed by evaporation. The aqueous phase was adjusted to pH 7.5 and extracted several times with dichloromethane. A whitish solid present between the aqueous and the organic layer that could not be dissolved with dichloromethane was filtered off affording 0.4 g of crude product. The combined organic extracts were dried over sodium sulfate and evaporated giving 4.2 g of crude product. Purification of both the filtered solid and the organic extract by flash chromatography over silica gel (eluent: dichloromethane/methanol/33% NH$_4$OH in 9:1:0.1 ratio) afforded 0.9 g of recovered 5-benzenesulfonyl-indazol-3-amine and 1.71 g of title compound as a yellow solid (43% yield).

1H-NMR (400 MHz), δ (ppm, DMSO-d$_6$): 13.27 (bs, 1H), 11.19 (bs, 1H), 8.61 (m, 1H), 7.91 (m, 2H), 7.79 (dd, J1=8.90 Hz, J2=1.83 Hz, 1H), 7.57-7.72 (m, 5H), 7.47 (d, J=2.5 Hz, 1H), 7.27 (dd, J1=9.15 Hz, J2=2.5 Hz, 1H), 2.36 (m, 4H), 2.45 (m, 4H), 2.23 (s, 3H).

Operating in an analogous way, the following compounds were obtained:

N-[5-(3,5-Difluoro-benzenesulfonyl)-1H-indazol-3-yl]-4-(4-methyl-piperazin-1-yl)-2-nitro-benzamide [(I), R1=R2=R3=H, R=3,5-difluorophenyl, Ar=4-(4-methyl-piperazin-1-yl)-2-nitro-phenyl], cpd. 6

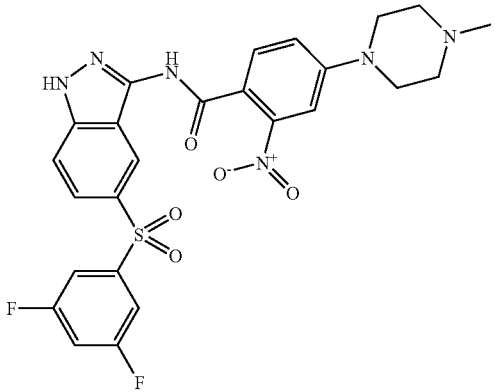

1H-NMR (400 MHz), δ (ppm, DMSO-d$_6$): 13.35 (bs, 1H), 11.24 (bs, 1H), 8.65 (m, 1H), 7.92 (m, 1H), 7.77-7.61 (m, 5H), 7.49 (m, 1H), 7.30 (m, 1H), 3.39 (m, 4H), 2.47 (m, 4H), 2.25 (s, 3H).

N-(5-Benzenesulfonyl-1H-indazol-3-yl)-4-(4-methyl-piperazin-1-yl)-benzamide [(I), R1=R2=R3=H, R=phenyl, Ar=4-(4-methyl-piperazin-1-yl)phenyl], cpd. 1

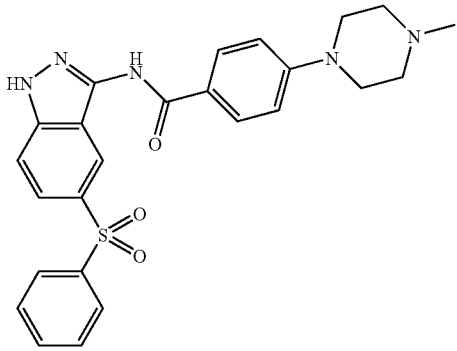

1H-NMR (400 MHz), δ (ppm, DMSO-d$_6$): 13.26 (bs, 1H), 10.78 (bs, 1H), 8.59 (m, 1H), 8.02 (m, 2H), 7.95 (m, 2H), 7.81 (d, J1=8.9 Hz, J2=1.7 Hz, 1H), 7.70-7.58 (m, 4H), 7.05 (m, 2H), 3.34 (m, 4H), 2.49 (m, 4H), 2.26 (s, 3H).

N-[5-(3,5-Difluoro-benzenesulfonyl)-1H-indazol-3-yl]-4-fluoro-2-nitro-benzamide [(I), R1=R2=R3=H, R=3,5-difluorophenyl, Ar=4-fluoro-2-nitrophenyl], cpd. 214

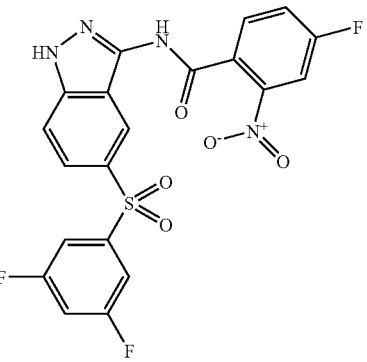

1H-NMR (400 MHz), δ (ppm, DMSO-d$_6$): 13.41 (bs, 1H), 11.51 (bs, 1H), 8.74 (m, 1H), 8.16 (m, 1H), 8.01 (m, 1H), 7.95 (m, 1H), 7.83 (m, 1H), 7.74-7.63 (m, 4H).

Example 21

Preparation of 2-amino-N-(5-benzenesulfonyl-1H-indazol-3-yl)-4-(4-methyl-piperazin-1-yl)-benzamide [(I), R1=R2=R3=H, R=phenyl, Ar=4-(4-methyl-piperazin-1-yl)-2-amino-phenyl], cpd. 7

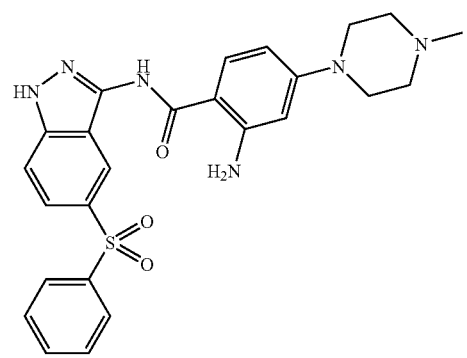

N-(5-benzenesulfonyl-1H-indazol-3-yl)-4-(4-methyl-piperazin-1-yl)-2-nitro-benzamide (1.71 g, 3.29 mmol) was suspended in a mixture of tetrahydrofuran (17 mL), ethanol (33 mL), water (25 mL) and cyclohexene (17 mL), treated with 10% palladium on carbon and stirred under reflux. After two hours the reaction was cooled to room temperature and filtered over celite washing thoroughly with tetrahydrofuran. Evaporation of the filtrate and purification of the crude product by flash chromatography over silica gel (eluent: dichloromethane/methanol/33% NH$_4$OH in 95:5:1 ratio) afforded 1.39 g of title compound as a yellow powder (86% yield).

1H-NMR (400 MHz), δ (ppm, DMSO-d$_6$): 13.17 (bs, 1H), 10.36 (bs, 2H), 8.45 (bs, 1H), 7.92 (m, 2H), 7.77 (dd, J1=8.78 Hz, J2=1.70 Hz, 1H), 7.73 (d, J=9.03 Hz, 1H), 7.55-7.67 (m, 4H), 6.57 (bs, 2H), 6.26 (dd, J1=9.03 Hz, J2=2.32 Hz, 1H), 6.19 (d, J=2.32 Hz, 1H), 3.21 (m, 4H), 2.42 (m, 4H), 2.21 (s, 3H).

Operating in an analogous way, the following compounds were obtained:

2-Amino-N-[5-(3,5-difluoro-benzenesulfonyl)-1H-indazol-3-yl]-4-(4-methyl-piperazin-1-yl)-benzamide [(I), R1=R2=R3=H, R=3,5-difluorophenyl, Ar=4-(4-methyl-piperazin-1-yl)-2-amino-phenyl], cpd. 9

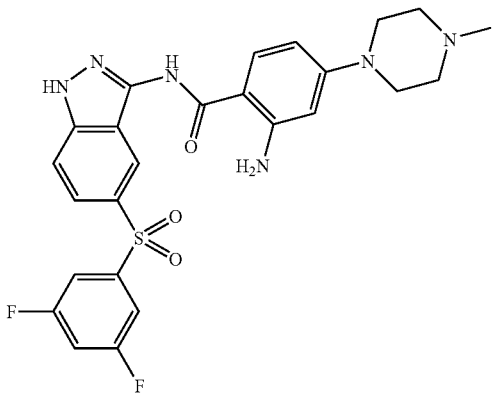

1H-NMR (400 MHz), δ (ppm, DMSO-d$_6$): 13.25 (bs, 1H), 10.41 (bs, 1H), 8.54 (m, 1H), 7.89 (m, 1H), 7.79-7.59 (m, 5H), 6.60 (bs, 2H), 6.28 (m, 1H), 6.22 (m, 4H), 2.47 (m, 4H), 2.26 (s, 3H).

2-Amino-N-[5-(3,5-difluoro-benzenesulfonyl)-1H-indazol-3-yl]-4-[methyl-(2-piperidin-1-yl-ethyl)-amino]-benzamide [(I), R1=R2=R3=H, R=3,5-difluorophenyl, Ar=4-[methyl-(2-piperidin-1-yl-ethyl)-amino]-2-amino-phenyl], cpd. 215

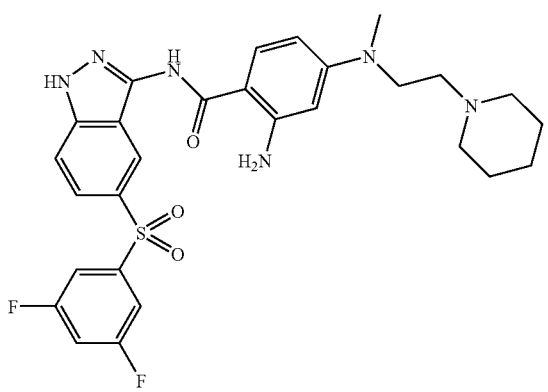

1H-NMR (400 MHz), δ (ppm, DMSO-d$_6$): 13.20 (bs, 1H), 10.28 (bs, 1H), 8.52 (m, 1H), 7.87 (dd, J1=8.9 Hz, J2=1.8 Hz, 1H), 7.74-7.70 (m, 3H), 7.65 (d, J=8.9 Hz, 1H), 7.62 (m, 1H), 6.59 (bs, 2H), 6.05 (dd, J1=9.0 Hz, J2=2.4 Hz, 1H), 6.96 (d, J=2.4 Hz, 1H), 3.44 (m, 2H), 2.94 (s, 3H), 2.45-2.35 (m, 6H), 1.50 (m, 4H), 1.39 (m, 2H).

Example 22

Preparation of 1H-pyrrole-2-carboxylic acid [2-(5-benzenesulfonyl-1H-indazol-3-ylcarbamoyl)-5-(4-methyl-piperazin-1-yl)-phenyl]amide [(I), R1=R2=R3=H, Ar=2-[(1H-pyrrole-2-carbonyl)amino]-4-(4-methyl-piperazin-1-yl)-phenyl, R=phenyl], cpd. 33

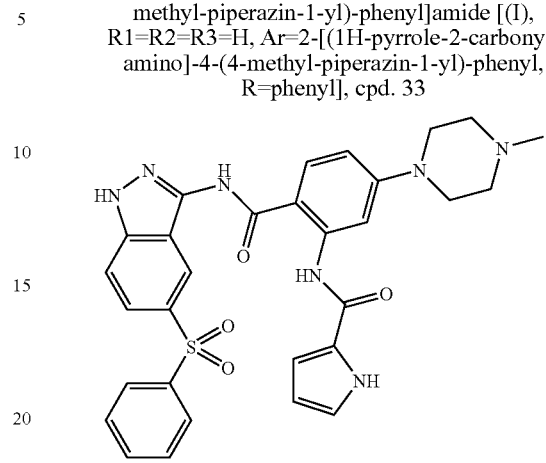

2-Amino-N-(5-benzenesulfonyl-1H-indazol-3-yl)-4-(4-methyl-piperazin-1-yl)-benzamide (245 mg, 0.5 mmol) was suspended in dichloromethane (10 mL), treated first with neat N,N-diisopropylethylamine (0.35 mL, 2 mmol) then with solid 1H-pyrrole-2-carbonyl chloride (258 mg, 2 mmol). The reaction was stirred at room temperature overnight then treated with additional acid chloride (258 mg) and N,N-diisopropylethylamine (0.35 mL). After two hours the solvent was removed under reduced pressure and the crude was taken up with tetrahydrofuran (30 mL) and treated with 2N NaOH (10 mL). After stirring overnight the solvent was removed and the solid was filtered and washed thoroughly with water. The crude was purified by flash chromatography over silica gel (eluent: ethyl acetate/methanol/aq.33% NH$_4$OH in 9:1:0.1 ratio) to give 60 mg of title compound.

1H-NMR (400 MHz), δ (ppm, DMSO-d$_6$): 13.35 (bs, 1H), 12.44 (s, 1H), 11.74 (bs, 1H), 10.98 (s, 1H), 8.61 (d, J=1.10 Hz, 1H), 8.39 (d, J=2.56 Hz, 1H), 8.07 (d, J=9.15 Hz, 1H), 7.93-7.97 (m, 2H), 7.85 (dd, J1=8.90 Hz, J2=1.70 Hz, 1H), 7.69 (d, J=8.90 Hz, 1H), 7.65 (m, 1H), 7.58 (m, 2H), 7.01 (m, 1H), 6.76 (m, 1H), 6.73 (m, 1H), 6.17 (m, 1H), 3.35 (m, 4H), 2.48 (m, 4H), 2.25 (s, 3H).

Operating in an analogous way, the following compounds were obtained:

(S)-Tetrahydro-furan-2-carboxylic acid [2-(5-benzenesulfonyl-1H-indazol-3-ylcarbamoyl)-5-(4-methyl-piperazin-1-yl)-phenyl]-amide [(I), R1=R2=R3=H, Ar=2-[((S)-tetrahydro-furan-2-carbonyl)amino]-4-(4-methyl-piperazin-1-yl)-phenyl, R=phenyl], cpd. 36

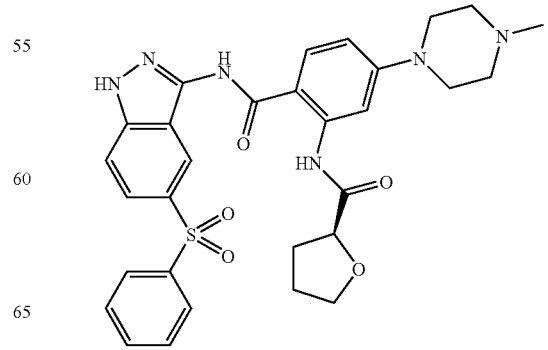

1H-NMR (400 MHz), δ (ppm, DMSO-d6): 13.34 (bs, 1H), 12.16 (bs, 1H), 10.90 (bs, 1H), 8.59 (bs, 1H), 8.34 (d, J=2.43 Hz, 1H), 8.02 (d, J=9.15 Hz, 1H), 7.95 (m, 2H), 7.84 (dd, J=8.90 Hz, J=1.82 Hz, 1H), 7.64-7.71 (m, 2H), 7.58-7.64 (m, 2H), 6.79 (dd, J1=9.15 Hz, J2=2.44 Hz, 1H), 4.41 (dd, J1=8.41 Hz, J2=4.88 Hz, 1H), 4.01 (m, 1H), 3.82 (m, 1H), 3.34 (m, 4H), 2.52 (m, 4H), 2.26 (s, 3H), 2.21 (m, 1H), 1.99-2.09 (m, 1H), 1.80-1.94 (m, 2H).

1H-Pyrrole-3-carboxylic acid [2-(5-benzenesulfonyl-1H-indazol-3-ylcarbamoyl)-5-(4-methyl-piperazin-1-yl)-phenyl]-amide [(I), R1=R2=R3=H, Ar=2-[(1H-pyrrole-3-carbonyl)amino]-4-(4-methyl-piperazin-1-yl)-phenyl, R=phenyl], cpd. 39

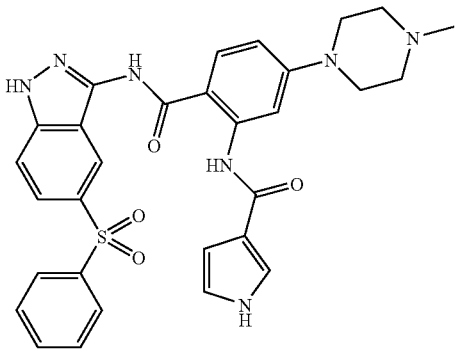

1-(Toluene-4-sulfonyl)-1H-pyrrole-3-carbonyl chloride was employed.
ESI (+) MS: m/z 584 (MH+).

Example 23

Preparation of N-(5-benzenesulfonyl-1H-indazol-3-yl)-4-(4-methyl-piperazin-1-yl)-2-(tetrahydro-pyran-4-ylamino)-benzamide [(I), R1=R2=R3=H, Ar=4-(4-methyl-piperazin-1-yl)-2-(tetrahydro-pyran-4-ylamino)-phenyl, R=phenyl], cpd. 10

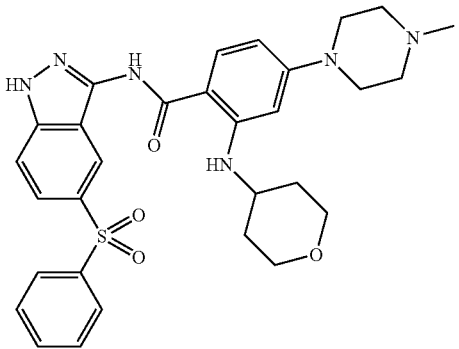

2-Amino-N-(5-benzenesulfonyl-1H-indazol-3-yl)-4-(4-methyl-piperazin-1-yl)-benzamide (245 mg, 0.5 mmol) was dissolved in dichloromethane (5 mL) and trifluoroacetic acid (0.77 mL, 10 mmol), treated first with tetrahydro-pyran-4-one (0.055 mL, 0.6 mmol) and then with tetramethylammonium triacetoxyborohydride (197 mg, 0.75 mmol). The reaction was stirred at room temperature overnight then additional ketone (0.055 mL, 0.6 mmol) and hydride (2 portions: 197 mg first and 50 mg after a couple of hours) were added. After additional stirring overnight the volatiles were removed under reduced pressure. Dichloromethane was added and the organic phase was washed with aqueous sodium hydrogen carbonate, dried over sodium sulfate and evaporated. The crude product was purified by flash chromatography over silica gel (eluent: dichloromethane/methanol/33% NH4OH in 95:5:1 ratio) affording 186 mg of product still containing some impurities. Further purification by preparative HPLC (basic method) gave 80 mg of title compound.

1H-NMR (400 MHz), δ (ppm, DMSO-d6): 13.22 (bs, 1H), 10.44 (bs, 1H), 8.41 (bs, 1H), 8.29 (d, J=7.81 Hz, 1H), 7.95 (m, 2H), 7.83 (m, 2H), 7.58-7.70 (m, 4H), 6.29 (dd, J1=9.03 Hz, J2=2.07 Hz, 1H), 6.18 (d, J=2.07 Hz, 1H), 3.82-3.88 (m, 2H), 3.74 (m, 1H), 3.54 (m, 2H), 3.28-3.32 (m, 4H), 2.46 (m, 4H), 2.68 (s, 3H), 1.99 (m, 2H), 1.40 (m, 2H).

Operating in an analogous way, the following compounds were obtained:

N-[5-(3,5-Difluoro-benzenesulfonyl)-1H-indazol-3-yl]-4-[methyl-(2-piperidin-1-yl-ethyl)-amino]-2-(tetrahydro-pyran-4-ylamino)-benzamide [(I), R1=R2=R3=H, Ar=4-[methyl-(2-piperidin-1-yl-ethyl)-amino]-2-(tetrahydro-pyran-4-ylamino)-phenyl, R=3,5-difluorophenyl], cpd. 137

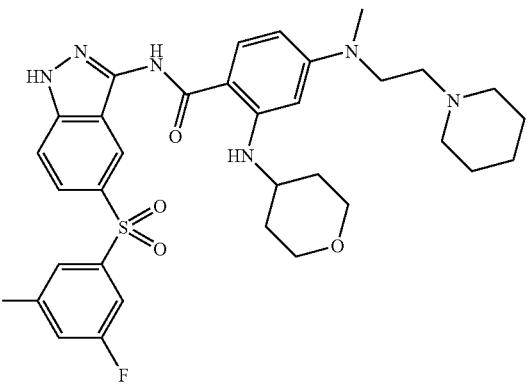

1H-NMR (400 MHz), δ (ppm, DMSO-d6): 13.24 (bs, 1H), 10.36 (bs, 1H), 8.47 (m, 1H), 8.33 (bd, J=7.3 Hz, 1H), 7.90 (dd, J1=8.9 Hz, J2=1.8 Hz, 1H), 7.81 (d, J=9.1 Hz, 1H), 7.72 (m, 2H), 7.67 (d, J=9.0 Hz, 1H), 7.64 (m, 1H), 6.05 (m, 1H), 5.89 (m, 1H), 3.85 (m, 2H), 3.66 (m, 1H), 3.54-3.45 (m, 4H), 3.00 (s, 3H), 2.48-2.37 (m, 6H), 2.00 (m, 2H), 1.56-1.36 (m, 8H).

Example 24

Preparation of 5-(3-fluoro-benzenesulfonyl)-1-trityl-1H-indazol-3-ylamine [(XVI), R1=R2=R3=H, R=3-fluorophenyl, R11=1-triphenylmethyl]

Step 1. 2,2,2-trifluoro-N-[5-(3-fluoro-benzenesulfonyl)-1H-indazol-3-yl]-acetamide [(XXI), R1=R2=R3=H, R=3-fluorophenyl]

A suspension of 5-(3-fluoro-benzenesulfonyl)-1H-indazol-3-ylamine (15.35 g, 52.69 mmol) in dry dichloromethane (200 mL) was treated with trifluoroacetic anhydride (23 mL, 163.4 mmol) and stirred overnight at room temperature. The solution was evaporated, treated with ethyl acetate and aqueous sodium hydrogen carbonate. The organic phase was separated, and the aqueous phase was further extracted with ethyl acetate. The combined organic extracts were dried and evaporated. The solid was triturated with a small amount of dichloromethane and filtered affording 18 g (88.3%) of title compound as a white powder.

1H-NMR (400 MHz), δ (ppm, DMSO-d$_6$): 13.62 (bs, 1H), 12.23 (bs, 1H), 8.62 (m, 1H), 7.90 (dd, J1=8.90 Hz, J2=1.83 Hz, 1H), 7.80-7.85 (m, 2H), 7.73 (dd, J1=8.90 Hz, J2=0.73 Hz, 1H), 7.70 (m, 1H), 7.55 (m, 1H).

Operating in an analogous way, the following compounds were obtained:

N-(5-Benzenesulfonyl-1H-indazol-3-yl)-2,2,2-trifluoro-acetamide [(XXI), R1=R2=R3=H, R=phenyl]

1H-NMR (400 MHz), δ (ppm, DMSO-d$_6$): 13.57 (bs, 1H), 12.21 (bs, 1H), 8.59 (m, 1H), 7.98-7.92 (m, 2H), 7.84 (m, 1H), 7.73-7.57 (m, 4H).

N-[5-(3,5-Difluoro-benzenesulfonyl)-1H-indazol-3-yl]-2,2,2-trifluoro-acetamide [(XXI), R1=R2=R3=H, R=3,5-difluorophenyl]

1H-NMR (400 MHz), δ (ppm, DMSO-d$_6$): 13.63 (bs, 1H), 12.22 (bs, 1H), 8.63 (m, 1H), 7.95 (d, J1=8.9 Hz, J2=1.8 Hz, 1H), 7.76-7.71 (m, 3H), 7.64 (m, 1H).

2,2,2-Trifluoro-N-[5-(3-fluoro-5-methoxy-benzenesulfonyl)-1H-indazol-3-yl]-acetamide [(XXI), R1=R2=R3=H, R=3-fluoro-5-methoxyphenyl]

ESI (+) MS: m/z 418 (MH$^+$).

Step 2. 2,2,2-trifluoro-N-[5-(3-fluoro-benzenesulfonyl)-1-trityl-1H-indazol-3-yl]-acetamide [(XXII), R1=R2=R3=H, R=3-fluorophenyl, R11=1-triphenylmethyl]

2,2,2-Trifluoro-N-[5-(3-fluoro-benzenesulfonyl)-1H-indazol-3-yl]-acetamide, (17.93 g, 46.33 mmol) in dry dichloromethane (300 mL) was treated with chlorotriphenylmethane (14.22 g, 50.96 mmol) and triethylamine (14.2 mL, 102 mmol). After stirring at room temperature for two days, the reaction was washed with a solution of NH$_4$Cl, dried and evaporated. The crude was used as such in the next step without any further purification.

ESI (+) MS: m/z 630 (MH$^+$).

Operating in an analogous way, the following compounds were obtained:

N-(5-Benzenesulfonyl-1-trityl-1H-indazol-3-yl)-2,2,2-trifluoro-acetamide [(XXII), R1=R2=R3=H, R=phenyl, R11=1-triphenylmethyl]

ESI (+) MS: m/z 612 (MH$^+$).

N-[5-(3,5-Difluoro-benzenesulfonyl)-1-trityl-1H-indazol-3-yl]-2,2,2-trifluoro-acetamide [(XXII), R1=R2=R3=H, R=3,5-difluorophenyl, R11=1-triphenylmethyl]

ESI (+) MS: m/z 648 (MH$^+$).

2,2,2-Trifluoro-N-[5-(3-fluoro-5-methoxy-benzenesulfonyl)-1-trityl-1H-indazol-3-yl]-acetamide [(XXII), R1=R2=R3=H, R=3-fluoro-5-methoxyphenyl, R11=1-triphenylmethyl]

ESI (+) MS: m/z 660 (MH$^+$).

Step 3. 5-(3-fluoro-benzenesulfonyl)-1-trityl-1H-indazol-3-ylamine [(XVI), R1=R2=R3=H, R=3-fluorophenyl, R11=1-triphenylmethyl]

The crude 2,2,2-Trifluoro-N-[5-(3-fluoro-benzenesulfonyl)-1-trityl-1H-indazol-3-yl]-acetamide (46.33 mmol) was treated with methanol (250 mL) and triethylamine (20 mL) and heated to reflux for 36 hours. The volatiles were partially evaporated, cooled and filtered. The solid was washed with a small volume of methanol then with water. After drying under vacuum at 70° C. and further purification by recrystallization from ethyl acetate the title compound was obtained as a white solid.

1H-NMR (400 MHz), δ (ppm, DMSO-d$_6$): 8.53 (m, 1H), 7.63-7.75 (m, 3H), 7.48-7.56 (m, 2H), 7.26 (m, 15H), 6.35 (m, 1H), 6.03 (bs, 2H).

Operating in an analogous way, the following compounds were obtained:

5-Benzenesulfonyl-1-trityl-1H-indazol-3-ylamine [(XVI), R1=R2=R3=H, R=phenyl, R11=1-triphenylmethyl]

ESI (+) MS: m/z 516 (MH$^+$).

5-(3,5-Difluoro-benzenesulfonyl)-1-trityl-1H-indazol-3-ylamine [(XVI), R1=R2=R3=H, R=3,5-difluorophenyl, R11=1-triphenylmethyl]

1H-NMR (400 MHz), δ (ppm, DMSO-d$_6$): 8.54 (m, 1H), 7.67-7.60 (m, 3H), 7.54 (d, J1=9.2 Hz, J2=1.9 Hz, 1H), 7.33-7.17 (m, 15H), 6.35 (d, J=9.4 Hz, 1H), 6.04 (bs, 2H).

5-(3-Fluoro-5-methoxy-benzenesulfonyl)-1-trityl-1H-indazol-3-ylamine [(XVI), R1=R2=R3=H, R=3-fluoro-5-methoxyphenyl, R11=1-triphenylmethyl]

1H-NMR (400 MHz), δ (ppm, DMSO-d$_6$): 8.54 (m, 1H), 7.52 (d, J1=9.2 Hz, J1=1.9 Hz, 1H), 7.34-7.14 (m, 18H), 6.36 (d, J=9.2 Hz, 1H), 6.04 (bs, 2H).

Example 25

Preparation of N-[5-(3-fluoro-benzenesulfonyl)-1-trityl-1H-indazol-3-yl]-4-(4-methyl-piperazin-1-yl)-2-nitro-benzamide [(XVII), R1=R2=R3=H, R=3-fluorophenyl, R11=1-triphenylmethyl, Ar=4-(4-methyl-piperazin-1-yl)-2-nitro-phenyl]

To a mixture of 5-(3-fluoro-benzenesulfonyl)-1-trityl-1H-indazol-3-ylamine (100 mg, 0.187 mmol), N,N-diisopropylethylamine (0.13 mL, 0.75 mmol) and dry-tetrahydrofuran (30 mL), at room temperature, was added 4-(4-methyl-piperazin-1-yl)-2-nitro-benzoyl chloride hydrochloride (66 mg, 0.206 mmol, prepared as described in Example 20). The mixture was stirred at room temperature for 1 hour then evaporated to dryness. The residue was dissolved in dichloromethane (50 mL), washed with saturated solution of sodium hydrogenocarbonate (50 mL), dried over sodium sulfate, evaporated to dryness and triturated with diethylether affording the title compound as a yellow powder (102 mg, 70% yield).

1H-NMR (400 MHz), δ (ppm, DMSO-d$_6$): 11.32 (bs, 1H), 8.57 (m, 1H), 7.78-7.73 (m, 2H), 7.67 (m, 1H), 7.61 (m, 1H), 7.55 (m, 1H), 7.48-7.04 (m, 18H), 6.51 (m, 1H), 3.31 (m, 4H), 2.45 (m. 4H), 2.23 (s, 3H).

Operating in an analogous way, the following compounds were obtained:

N-[5-(3,5-Difluoro-benzenesulfonyl)-1-trityl-1H-indazol-3-yl]-4-[(2-dimethylamino-ethyl)-methyl-amino]-2-nitro-benzamide [(XVII), R1=R2=R3=H, R=3,5-difluorophenyl, R11=1-triphenylmethyl, Ar=4-[(2-dimethylamino-ethyl)-methyl-amino]-2-nitro-phenyl]

1H-NMR (400 MHz), δ (ppm, DMSO-$d_6$): 11.23 (bs, 1H), 8.56 (m, 1H), 7.69-7.61 (m, 5H), 7.36-7.06 (m, 16H), 6.94 (m, 1H), 6.50 (d, J=8.9 Hz, 1H), 3.54 (m, 2H), 3.02 (s, 3H), 2.40 (m, 2H), 2.19 (s, 6H).

N-[5-(3,5-Difluoro-benzenesulfonyl)-1-trityl-1H-indazol-3-yl]-4-[(2-dimethylamino-ethyl)-ethyl-amino]-2-nitro-benzamide [(XVII), R1=R2=R3=H, R=3,5-difluorophenyl, R11=1-triphenylmethyl, Ar=4-[(2-dimethylamino-ethyl)-ethyl-amino]-2-nitro-phenyl]

1H-NMR (400 MHz), δ (ppm, DMSO-$d_6$): 11.22 (bs, 1H), 8.55 (m, 1H), 7.70-7.61 (m, 5H), 7.37-7.25 (m, 16H), 6.91 (m, 1H), 6.50 (d, J=8.9 Hz, 1H), 3.53-3.43 (m, 4H), 2.41 (m, 2H), 2.21 (s, 6H), 1.11 (bt, 3H).

N-[5-(3,5-Difluoro-benzenesulfonyl)-1-trityl-1H-indazol-3-yl]-4-(4-ethyl-[1,4]diazepan-1-yl)-2-nitro-benzamide [(XVII), R1=R2=R3=H, R=3,5-difluorophenyl, R11=1-triphenylmethyl, Ar=4-(4-ethyl-[1,4]diazepan-1-yl)-2-nitro-phenyl]

ESI (+) MS: m/z 827 (MH$^+$).

N-[5-(3,5-Difluoro-benzenesulfonyl)-1-trityl-1H-indazol-3-yl]-4-(4-dimethylamino-piperidin-1-yl)-2-nitro-benzamide [(XVII), R1=R2=R3=H, R=3,5-difluorophenyl, R11=1-triphenylmethyl, Ar=4-(4-dimethylamino-piperidin-1-yl)-2-nitro-phenyl]

1H-NMR (400 MHz), δ (ppm, DMSO-$d_6$): 11.30 (bs, 1H), 8.57 (m, 1H), 7.70-7.62 (m, 5H), 7.46-7.04 (m, 17H), 6.50 (m, 1H), 3.97 (m, 2H), 2.89 (m, 2H), 2.42 (m, 1H), 2.26 (s, 6H), 1.86 (m, 2H), 1.44 (m, 2H).

N-[5-(3,5-Difluoro-benzenesulfonyl)-1-trityl-1H-indazol-3-yl]-4-[methyl-(1-methyl-pyrrolidin-3-yl)-amino]-2-nitro-benzamide [(XVII), R1=R2=R3=H, R=3,5-difluorophenyl, R11=1-triphenylmethyl, Ar=4-[methyl-(1-methyl-pyrrolidin-3-yl)-amino]-2-nitro-phenyl]

ESI (+) MS: m/z 813 (MH$^+$).

N-[5-(3,5-Difluoro-benzenesulfonyl)-1-trityl-1H-indazol-3-yl]-4-[methyl-(2-piperidin-1-yl-ethyl)-amino]-2-nitro-benzamide [(XVII), R1=R2=R3=H, R=3,5-difluorophenyl, R11=1-triphenylmethyl, Ar=4-[methyl-(2-piperidin-1-yl-ethyl)-amino]-2-nitro-phenyl]

1H-NMR (400 MHz), δ (ppm, DMSO-$d_6$): 11.24 (bs, 1H), 8.57 (m, 1H), 7.70-7.62 (m, 5H), 7.38-7.10 (m, 16H), 6.95 (m, 1H), 6.52 (m, 1H), 3.56 (m, 2H), 3.03 (s, 3H), 2.48-2.35 (m, 6H), 1.53-1.33 (m, 6H).

N-[5-(3,5-Difluoro-benzenesulfonyl)-1-trityl-1H-indazol-3-yl]-2-nitro-4-(2-pyrrolidin-1-yl-ethoxy)-benzamide [(XVII), R1=R2=R3=H, R=3,5-difluorophenyl, R11=1-triphenylmethyl, Ar=2-nitro-4-(2-pyrrolidin-1-yl-ethoxy)-phenyl]

1H-NMR (400 MHz), δ (ppm, DMSO-$d_6$): 11.50 (bs, 1H), 8.66 (m, 1H), 7.82 (m, 1H), 7.71-7.63 (m, 4H), 7.43-7.12 (m, 16H), 6.84 (m, 1H), 6.54 (m, 1H), 4.26 (m, 2H), 2.84 (m, 2H), 2.55 (m, 4H), 1.70 (m, 4H).

N-[5-(3,5-Difluoro-benzenesulfonyl)-1-trityl-1H-indazol-3-yl]-4-{[2-(isopropyl-methyl-amino)-ethyl]-methyl-amino}-2-nitro-benzamide [(XVII), R1=R2=R3=H, R=3,5-difluorophenyl, R11=1-triphenylmethyl, Ar=4-{[2-(isopropyl-methyl-amino)-ethyl]methyl-amino}-2-nitro-phenyl]

ESI (+) MS: m/z 829 (MH$^+$).

N-[5-(3,5-Difluoro-benzenesulfonyl)-1-trityl-1H-indazol-3-yl]-4-[methyl-(2-morpholin-4-yl-ethyl)-amino]-2-nitro-benzamide [(XVII), R1=R2=R3=H, R=3,5-difluorophenyl, R11=1-triphenylmethyl, Ar=4-[methyl-(2-morpholin-4-yl-ethyl)-amino]-2-nitro-phenyl]

1H-NMR (400 MHz), δ (ppm, DMSO-$d_6$): 11.24 (bs, 1H), 8.56 (m, 1H), 7.70-7.62 (m, 5H), 7.38-7.10 (m, 16H), 6.96 (m, 1H), 6.51 (m, 1H), 3.63-3.51 (m, 6H), 3.04 (s, 3H), 2.50-2.40 (m, 6H).

N-[5-(3,5-Difluoro-benzenesulfonyl)-1-trityl-1H-indazol-3-yl]-4-[(3-dimethylamino-propyl)-methyl-amino]-2-nitro-benzamide [(XVII), R1=R2=R3=H, R=3,5-difluorophenyl, R11=1-triphenylmethyl, Ar=4-[(3-dimethylamino-propyl)-methyl-amino]-2-nitro-phenyl]

1H-NMR (400 MHz), δ (ppm, DMSO-$d_6$): 11.24 (bs, 1H), 8.56 (m, 1H), 7.70-7.62 (m, 5H), 7.38-7.10 (m, 16H), 6.96 (m, 1H), 6.51 (m, 1H), 3.46 (m, 2H), 3.01 (s, 3H), 2.29 (m, 2H), 2.20 (s, 6H), 1.68 (m, 2H).

N-[5-(3,5-Difluoro-benzenesulfonyl)-1-trityl-1H-indazol-3-yl]-4-(2-dimethylamino-ethoxy)-2-nitro-benzamide [(XVII), R1=R2=R3=H, R=3,5-difluorophenyl, R11=1-triphenylmethyl, Ar=4-(2-dimethylamino-ethoxy)-2-nitro-phenyl]

ESI (+) MS: m/z 788 (MH$^+$).

N-[5-(3,5-Difluoro-benzenesulfonyl)-1-trityl-1H-indazol-3-yl]-4-(4-methyl-piperazin-1-yl)-2-nitro-benzamide [(XVII), R1=R2=R3=H, R=3,5-difluorophenyl, R11=1-triphenylmethyl, Ar=4-(4-methyl-piperazin-1-yl)-2-nitro-phenyl]

ESI (+) MS: m/z 799 (MH$^+$).

N-[5-(3,5-Difluoro-benzenesulfonyl)-1-trityl-1H-indazol-3-yl]-4-dimethylaminomethyl-2-nitro-benzamide [(XVII), R1=R2=R3=H, R=3,5-difluorophenyl, R11=1-triphenylmethyl, Ar=4-dimethylaminomethyl-2-nitro-phenyl]

1H-NMR (400 MHz), δ (ppm, DMSO-$d_6$): 11.56 (bs, 1H), 8.70 (m, 1H), 8.06 (m, 1H), 7.84-7.62 (m, 6H), 7.38-7.10 (m, 15H), 6.55 (m, 1H), 3.57 (bs, 2H), 2.21 (bs, 6H).

N-[5-(3,5-Difluoro-benzenesulfonyl)-1-trityl-1H-indazol-3-yl]-4-(1-methyl-piperidin-4-yloxy)-2-nitro-benzamide [(XVII), R1=R2=R3=H, R=3,5-difluorophenyl, R11=1-triphenylmethyl, Ar=4-(1-methyl-piperidin-4-yloxy)-2-nitro-phenyl]

ESI (+) MS: m/z 814 (MH$^+$).

N-[5-(3,5-Difluoro-benzenesulfonyl)-1-trityl-1H-indazol-3-yl]-4-(4-methyl-piperazin-1-yl)-benzamide [(XVII), R1=R2=R3=H, R=3,5-difluorophenyl, R11=1-triphenylmethyl, Ar=4-(4-methyl-piperazin-1-yl)-phenyl]

1H-NMR (400 MHz), δ (ppm, DMSO-d$_6$): 10.79 (bs, 1H), 8.50 (d, J=8.7 Hz, 1H), 7.99 (m, 2H), 7.72 (m, 2H), 7.68-7.60 (m, 2H), 7.38-7.16 (m, 15H), 7.02 (m, 2H), 6.52 (d, J=9.4 Hz, 1H), 3.30 (m, 4H), 2.46 (m, 4H), 2.24 (s, 3H).

N-[5-(3,5-Difluoro-benzenesulfonyl)-1-trityl-1H-indazol-3-yl]-terephthalamic acid methyl ester [(XVII), R1=R2=R3=H, R=3,5-difluorophenyl, R11=1-triphenylmethyl, Ar=4-(methoxycarbonyl)-phenyl]

ESI (+) MS: m/z 714 (MH$^+$).

N-[5-(3,5-Difluoro-benzenesulfonyl)-1-trityl-1H-indazol-3-yl]-4-(4-methyl-[1,4]diazepan-1-yl)-2-nitro-benzamide [(XVII), R1=R2=R3=H, R=3,5-difluorophenyl, R11=1-triphenylmethyl, Ar=4-(4-methyl-[1,4]diazepan-1-yl)-2-nitro-phenyl]

ESI (+) MS: nah 813 (MH$^+$).

Example 26

Preparation of 2-amino-N-[5-(3,5-difluoro-benzenesulfonyl)-1-trityl-1H-indazol-3-yl]-4-[(2-dimethylamino-ethyl)-methyl-amino]-benzamide [(XVII), R1=R2=R3=H, R=3,5-difluorophenyl, R11=1-triphenylmethyl, Ar=4-[(2-dimethylamino-ethyl)-methyl-amino]-2-amino-phenyl]

A mixture of N-[5-(3,5-difluoro-benzenesulfonyl)-1-trityl-1H-indazol-3-yl]-4-[(2-dimethylamino-ethyl)-methyl-amino]-2-nitro-benzamide (1.0 g, 1.25 mmol), cyclohexene (2 mL), 1,4-dioxane (50 mL) and 10% Pd/C (0.1 g) was stirred at 85° C. for 5 hours. More cyclohexene (3 mL) and 10% Pd/C (0.2 g) were then added and the mixture stirred at 90° C. for additional 6 hours. The reaction mixture was then cooled to room temperature and filtered over celite washing thoroughly with ethanol. The filtrate was evaporated to dryness affording the title compound as a pale brown solid (910 mg, 94% yield).

1H-NMR (400 MHz), δ (ppm, DMSO-d$_6$): 10.31 (bs, 1H), 8.42 (m, 1H), 7.76-7.59 (m, 5H), 7.38-7.18 (m, 15H), 6.61 (bs, 2H), 6.51 (d, J=9.2 Hz, 1H), 6.03 (dd, J1=9.2 Hz, J2=2.4 Hz, 1H), 5.96 (d, J=2.4 Hz, 1H), 3.44 (m, 2H), 2.94 (s, 3H), 2.40 (m, 2H), 2.21 (s, 6H).

Operating in an analogous way, the following compounds were obtained:

2-Amino-N-[5-(3,5-difluoro-benzenesulfonyl)-1-trityl-1H-indazol-3-yl]-4-[(2-dimethylamino-ethyl)-ethyl-amino]-benzamide [(XVII), R1=R2=R3=H, R=3,5-difluorophenyl, R11=1-triphenylmethyl, Ar=4-[(2-dimethylamino-ethyl)-ethyl-amino]-2-amino-phenyl]

1H-NMR (400 MHz), δ (ppm, DMSO-d$_6$): 10.29 (bs, 1H), 8.41 (m, 1H), 7.76-7.60 (m, 5H), 7.39-7.16 (m, 15H), 6.60 (bs, 2H), 6.50 (d, J=9.0 Hz, 1H), 6.02-5.95 (m, 2H), 3.42-3.34 (m, 4H), 2.42 (m, 2H), 2.23 (s, 6H), 1.13 (bt, J=6.8 Hz, 3H).

2-Amino-N-[5-(3,5-difluoro-benzenesulfonyl)-1-trityl-1H-indazol-3-yl]-4-(4-ethyl-[1,4]diazepan-1-yl)-benzamide [(XVII), R1=R2=R3=H, R=3,5-difluorophenyl, R11=1-triphenylmethyl, Ar=4-(4-ethyl-[1,4]diazepan-1-yl)-2-amino-phenyl]

1H-NMR (400 MHz), δ (ppm, DMSO-d$_6$): 10.28 (bs, 1H), 8.39 (m, 1H), 7.73-7.68 (m, 3H), 7.65-7.58 (m, 2H), 7.36-7.14 (m, 15H), 6.55 (bs, 2H), 6.47 (d, J=9.1 Hz, 1H), 6.04 (dd, J1=9.1 Hz, J2=2.2 Hz, 1H), 5.98 (d, J=2.2 Hz, 1H), 3.49 (m, 2H), 3.45 (m, 2H), 3.34-3.25 (m, 4H), 2.69 (m, 2H), 1.85 (m, 2H), 0.98 (bt, J=6.9 Hz, 3H).

2-Amino-N-[5-(3,5-difluoro-benzenesulfonyl)-1-trityl-1H-indazol-3-yl]-4-(4-dimethylamino-piperidin-1-yl)-benzamide [(XVII), R1=R2=R3=H, R=3,5-difluorophenyl, R11=1-triphenylmethyl, Ar=4-(4-dimethylamino-piperidin-1-yl)-2-amino-phenyl]

ESI (+) MS: m/z 797 (MH$^+$).

2-Amino-N-[5-(3,5-difluoro-benzenesulfonyl)-1-trityl-1H-indazol-3-yl]-4-[methyl-(1-methyl-pyrrolidin-3-yl)-amino]-benzamide [(XVII), R1=R2=R3=H, R=3,5-difluorophenyl, R11=1-triphenylmethyl, Ar=4-[methyl-(1-methyl-pyrrolidin-3-yl)-amino]-2-amino-phenyl]

ESI (+) MS: m/z 783 (MH$^+$).

2-Amino-N-[5-(3,5-difluoro-benzenesulfonyl)-1-trityl-1H-indazol-3-yl]-4-(2-pyrrolidin-1-yl-ethoxy)-benzamide [(XVII), R1=R2=R3=H, R=3,5-difluorophenyl, R11=1-triphenylmethyl, Ar=4-(2-pyrrolidin-1-yl-ethoxy)-2-amino-phenyl]

1H-NMR (400 MHz), δ (ppm, DMSO-d$_6$): 10.54 (bs, 1H), 8.42 (m, 1H), 7.80 (d, J=9.0 Hz, 1H), 7.72 (m, 2H), 7.65-7.57 (m, 2H), 7.36-7.14 (m, 15H), 6.71 (bs, 2H), 6.49 (d, J=9.1 Hz, 1H), 6.30 (d, J=2.6 Hz, 1H), 6.16 (dd, J1=9.1 Hz, J2=2.6 Hz, 1H), 4.04 (m, 2H), 2.78 (m, 2H), 2.52 (m, 4H), 1.68 (m, 4H).

2-Amino-N-[5-(3,5-difluoro-benzenesulfonyl)-1-trityl-1H-indazol-3-yl]-4-{[2-(isopropyl-methyl-amino)-ethyl]-methyl-amino}-benzamide [(XVII), R1=R2=R3=H, R=3,5-difluorophenyl, R11=1-triphenylmethyl, Ar=4-{[2-(isopropyl-methyl-amino)-ethyl]methyl-amino}-2-amino-phenyl]

ESI (+) MS: m/z 799 (MH$^+$).

2-Amino-N-[5-(3,5-difluoro-benzenesulfonyl)-1-trityl-1H-indazol-3-yl]-4-[methyl-(2-morpholin-4-yl-ethyl)-amino]-benzamide [(XVII), R1=R2=R3=H, R=3,5-difluorophenyl, R11=1-triphenylmethyl, Ar=4-[methyl-(2-morpholin-4-yl-ethyl)-amino]-2-amino-phenyl]

1H-NMR (400 MHz), δ (ppm, DMSO-$d_6$): 10.30 (bs, 1H), 8.40 (m, 1H), 7.75-7.69 (m, 3H), 7.67-7.59 (m, 2H), 7.37-7.16 (m, 15H), 6.59 (bs, 2H), 6.49 (d, J=8.7 Hz, 1H), 6.03 (dd, J1=9.0 Hz, J2=2.7 Hz, 1H), 5.96 (d, J=2.6 Hz, 1H), 3.6-3.5 (m, 4H), 3.46 (m, 2H), 2.94 (s, 3H), 2.48-2.39 (m, 6H).

2-Amino-N-[5-(3,5-difluoro-benzenesulfonyl)-1-trityl-1H-indazol-3-yl]-4-[(3-dimethylamino-propyl)-methyl-amino]-benzamide [(XVII), R1=R2=R3=H, R=3,5-difluorophenyl, R11=1-triphenylmethyl, Ar=4-[(3-dimethylamino-propyl)-methyl-amino]-2-amino-phenyl]

1H-NMR (400 MHz), δ (ppm, DMSO-$d_6$): 10.30 (bs, 1H), 8.41 (m, 1H), 7.75-7.69 (m, 3H), 7.67-7.59 (m, 2H), 7.38-7.17 (m, 15H), 6.59 (bs, 2H), 6.50 (d, J=9.2 Hz, 1H), 6.05 (dd, J1=9.1 Hz, J2=2.4 Hz, 1H), 5.96 (d, J=2.4 Hz, 1H), 3.36 (m, 2H), 2.92 (s, 3H), 2.31 (m, 2H), 2.21 (bs, 6H), 1.67 (m, 2H).

2-Amino-N-[5-(3,5-difluoro-benzenesulfonyl)-1-trityl-1H-indazol-3-yl]-4-(2-dimethylamino-ethoxy)-benzamide [(XVII), R1=R2=R3=H, R=3,5-difluorophenyl, R11=1-triphenylmethyl, Ar=4-(2-dimethylamino-ethoxy)-2-amino-phenyl]

1H-NMR (400 MHz), δ (ppm, DMSO-$d_6$): 10.56 (bs, 1H), 8.45 (m, 1H), 7.82 (d, J=9.0 Hz, 1H), 7.74 (m, 2H), 7.68-7.61 (m, 2H), 7.38-7.17 (m, 15H), 6.74 (bs, 2H), 6.52 (d, J=9.1 Hz, 1H), 6.32 (d, J=2.6 Hz, 1H), 6.19 (dd, J1=9.1 Hz, J2=2.6 Hz, 1H), 4.05 (m, 2H), 2.64 (m, 2H), 2.25 (s, 6H).

2-Amino-N-[5-(3,5-difluoro-benzenesulfonyl)-1-trityl-1H-indazol-3-yl]-4-(4-methyl-piperazin-1-yl)-benzamide [(XVII), R1=R2=R3=H, R=3,5-difluorophenyl, R11=1-triphenylmethyl, Ar=4-(4-methyl-piperazin-1-yl)-2-amino-phenyl]

ESI (+) MS: m/z 769 (MH$^+$).

2-Amino-N-[5-(3,5-difluoro-benzenesulfonyl)-1-trityl-1H-indazol-3-yl]-4-dimethylaminomethyl-benzamide [(XVII), R1=R2=R3=H, R=3,5-difluorophenyl, R11=1-triphenylmethyl, Ar=4-dimethylaminomethyl-2-amino-phenyl]

1H-NMR (400 MHz), δ (ppm, DMSO-$d_6$): 10.79 (bs, 1H), 8.47 (m, 1H), 7.85 (d, J=8.5 Hz, 1H), 7.73 (m, 2H), 7.68-7.61 (m, 2H), 7.39-7.16 (m, 15H), 6.80 (m, 1H), 6.68 (bs, 2H), 6.61 (m, 1H), 6.52 (d, J=9.4 Hz, 1H), 3.74 (bs, 2H), 2.47 (bs, 6H).

2-Amino-N-[5-(3,5-difluoro-benzenesulfonyl)-1-trityl-1H-indazol-3-yl]-4-(1-methyl-piperidin-4-yloxy)-benzamide [(XVII), R1=R2=R3=H, R=3,5-difluorophenyl, R11=1-triphenylmethyl, Ar=4-(1-methyl-piperidin-4-yloxy)-2-amino-phenyl]

ESI (+) MS: m/z 784 (MH$^+$).

2-Amino-N-[5-(3,5-difluoro-benzenesulfonyl)-1-trityl-1H-indazol-3-yl]-4-(4-methyl-[1,4]diazepan-1-yl)-benzamide [(XVII), R1=R2=R3=H, R=3,5-difluorophenyl, R11=1-triphenylmethyl, Ar=4-(4-methyl-[1,4]diazepan-1-yl)-2-amino-phenyl]

ESI (+) MS: m/z 783 (MH$^+$).

Example 27

Preparation of N-[5-(3,5-difluoro-benzenesulfonyl)-1H-indazol-3-yl]-4-[(2-dimethylamino-ethyl)-methyl-amino]-2-(tetrahydro-pyran-4-ylamino)-benzamide [(I), R1=R2=R3=H, R=3,5-difluorophenyl, Ar=4-[(2-dimethylamino-ethyl)-methyl-amino]-2-(tetrahydro-pyran-4-ylamino)-phenyl], cpd. 133

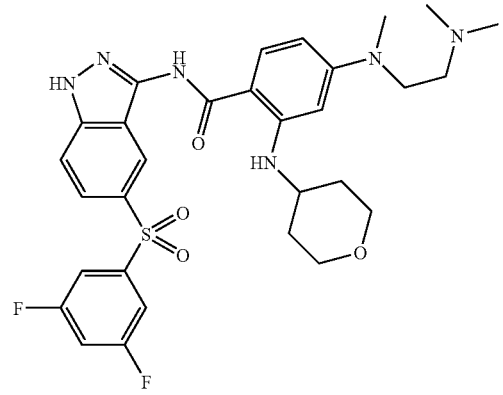

To a solution of 2-amino-N-[5-(3,5-difluoro-benzenesulfonyl)-1-trityl-1H-indazol-3-yl]-4-[(2-dimethylamino-ethyl)-methyl-amino]-benzamide (400 mg, 0.52 mmol) in dichloromethane (5 mL) were added tetrahydro-pyran-4-one (0.071 mL, 0.78 mmol), trifluoroacetic acid (0.108 mL, 1.4 mmol) and tetramethylammonium triacetoxyborohydride (205 mg, 0.78 mmol). The mixture was stirred at room temperature overnight, then additional trifluoroacetic acid (0.8 mL) and tetramethylammonium triacetoxyborohydride (410 mg) were added. After stirring for additional 3 hours at room temperature the mixture was diluted with dichloromethane, washed with saturated solution of sodium hydrogenocarbonate, brine, dried over sodium sulfate and evaporated to dryness. The crude was purified by flash chromatography on silica gel using dichloromethane/methanol/NH$_4$OH 96:4:0.5 as the eluant, affording 175 mg of the title compound as a pale yellow solid.

1H-NMR (400 MHz), δ (ppm, DMSO-$d_6$): 13.25 (bs, 1H), 10.37 (bs, 1H), 8.47 (m, 1H), 8.34 (bd, J=7.4 Hz, 1H), 7.91 (dd, J1=8.9 Hz, J2=1.8 Hz, 1H), 7.81 (d, J=9.1 Hz, 1H), 7.72 (m, 2H), 7.68 (d, J=8.9 Hz, 1H), 7.64 (m, 1H), 6.07 (dd, J1=9.1 Hz, J2=2.2 Hz, 1H), 5.90 (d, J=2.2 Hz, 1H), 3.89-3.82 (m, 2H), 3.67 (m, 1H), 3.54-3.46 (m, 4H), 3.00 (s, 3H), 2.47 (m, 2H), 2.26 (bs, 6H), 2.04-1.96 (m, 2H), 1.47-1.36 (m, 2H).

Operating in an analogous way, the following compounds were obtained:

N-[5-(3,5-Difluoro-benzenesulfonyl)-1H-indazol-3-yl]-4-[(2-dimethylamino-ethyl)-ethyl-amino]-2-(tetrahydro-pyran-4-ylamino)-benzamide [(I), R1=R2=R3=H, R=3,5-difluorophenyl, Ar=4-[(2-dimethylamino-ethyl)-ethyl-amino]-2-(tetrahydro-pyran-4-ylamino)-phenyl], cpd. 141

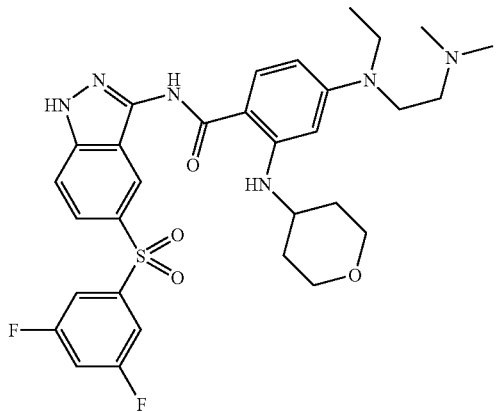

1H-NMR (400 MHz), δ (ppm, DMSO-d₆): 13.22 (bs, 1H), 10.33 (bs, 1H), 8.45 (m, 1H), 8.33 (bd, J=7.4 Hz, 1H), 7.90 (dd, J1=8.9 Hz, J2=1.8 Hz, 1H), 7.79 (d, J=9.2 Hz, 1H), 7.71 (m, 2H), 7.66 (d, J=8.9 Hz, 1H), 7.63 (m, 1H), 6.02 (dd, J1=9.1 Hz, J2=2.2 Hz, 1H), 5.86 (d, J=2.2 Hz, 1H), 3.88-3.81 (m, 2H), 3.62 (m, 1H), 3.51-3.38 (m, 6H), 2.42 (m, 2H), 2.22 (bs, 6H), 2.02-1.94 (m, 2H), 1.47-1.36 (m, 2H), 1.12 (bt, J=6.8 Hz, 3H).

N-[5-(3,5-Difluoro-benzenesulfonyl)-1H-indazol-3-yl]-4-(4-ethyl-[1,4]diazepan-1-yl)-2-(tetrahydro-pyran-4-ylamino)-benzamide [(I), R1=R2=R3=H, R=3,5-difluorophenyl, Ar=4-(4-ethyl-[1,4]diazepan-1-yl)-2-(tetrahydro-pyran-4-ylamino)-phenyl], cpd. 107

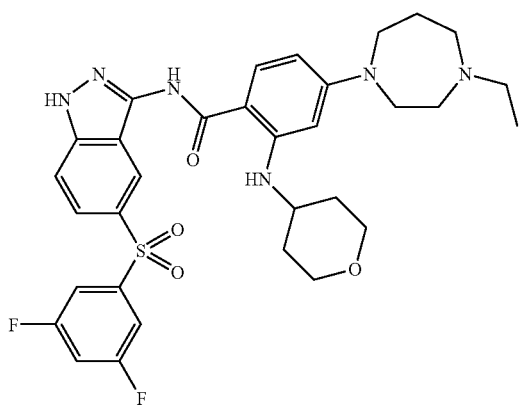

1H-NMR (400 MHz), δ (ppm, DMSO-d₆): 13.23 (bs, 1H), 10.35 (bs, 1H), 8.46 (m, 1H), 8.34 (bd, J=7.3 Hz, 1H), 7.90 (dd, J1=8.9 Hz, J2=1.7 Hz, 1H), 7.80 (d, J=9.2 Hz, 1H), 7.71 (m, 2H), 7.66 (d, J=8.9 Hz, 1H), 7.63 (m, 1H), 6.10 (m, 1H), 5.90 (m, 1H), 3.83 (m, 2H), 3.69 (m, 1H), 3.62-3.48 (m, 6H), 2.71 (m, 2H), 2.53-2.44 (m, 4H), 1.97 (m, 2H), 1.87 (m, 2H), 1.40 (m, 2H), 1.00 (bs, 3H).

N-[5-(3,5-Difluoro-benzenesulfonyl)-1H-indazol-3-yl]-4-(4-dimethylamino-piperidin-1-yl)-2-(tetrahydro-pyran-4-ylamino)-benzamide [(I), R1=R2=R3=H, R=3,5-difluorophenyl, Ar=4-(4-dimethylamino-piperidin-1-yl)-2-(tetrahydro-pyran-4-ylamino)-phenyl], cpd. 145

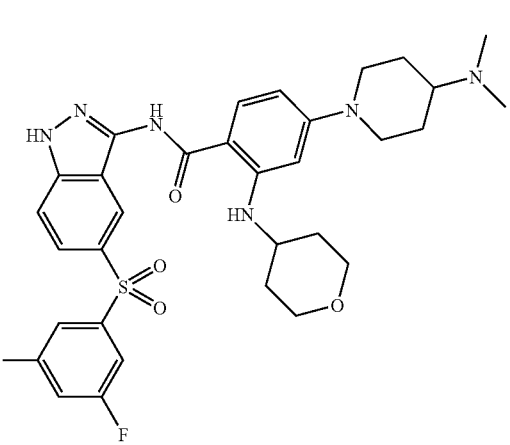

1H-NMR (400 MHz), δ (ppm, DMSO-d₆): 13.24 (bs, 1H), 10.42 (bs, 1H), 8.45 (m, 1H), 8.27 (d, J=7.6 Hz, 1H), 7.89 (dd, J1=8.9 Hz, J2=1.8 Hz, 1H), 7.80 8d, J=9.1 Hz, 1H), 7.71 (m, 2H), 7.66 (dd, J1=8.9 Hz, J2=0.6 Hz, 1H), 7.62 (m, 1H), 6.25 (m, 1H), 6.14 (m, 1H), 3.89 (m, 2H), 3.82 (m, 2H), 3.70 (m, 1H), 3.51 (m, 2H), 2.80 (m, 2H), 2.32 (m, 1H), 2.21 (s, 6H), 1.95 (m, 2H), 1.82 (m, 2H), 1.5-1.3 (m, 4H).

N-[5-(3,5-Difluoro-benzenesulfonyl)-1H-indazol-3-yl]-4-[methyl-(1-methyl-pyrrolidin-3-yl)-amino]-2-(tetrahydro-pyran-4-ylamino)-benzamide [(I), R1=R2=R3=H, R=3,5-difluorophenyl, Ar=4-[methyl-(1-methyl-pyrrolidin-3-yl)-amino]-2-(tetrahydro-pyran-4-ylamino)-phenyl], cpd. 149

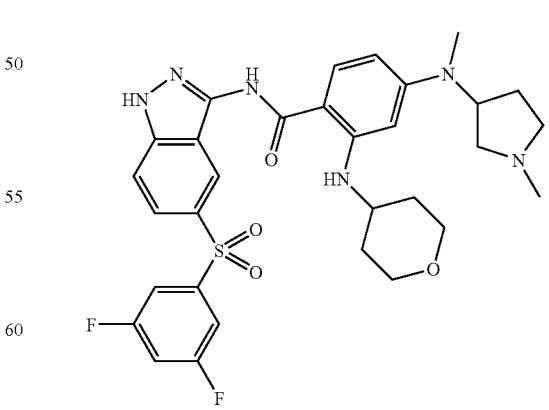

1H-NMR (400 MHz), δ (ppm, DMSO-d₆): 13.25 (bs, 1H), 10.38 (bs, 1H), 8.47 (m, 1H), 8.34 (d, J=7.4 Hz, 1H), 7.91 (dd, J1=8.9 Hz, J2=1.8 Hz, 1H), 7.81 (d, J=9.1 Hz, 1H), 7.73 (m, 2H), 7.68 (d, J=9.0 Hz, 1H), 7.64 (m, 1H), 6.17 (dd, J1=9.1 Hz, J2=2.3 Hz, 1H), 6.02 (d, J=2.3 Hz, 1H), 4.60 (m, 1H), 3.84 (m, 2H), 3.72 (m, 1H), 3.53 (m, 2H), 2.94 (s, 3H), 2.9-2.7 (m, 2H), 2.4-2.1 (m, 6H), 1.99 (m, 2H), 1.77 (m, 1H), 1.41 (m, 2H).

N-[5-(3,5-Difluoro-benzenesulfonyl)-1H-indazol-3-yl]-4-(2-pyrrolidin-1-yl-ethoxy)-2-(tetrahydro-pyran-4-ylamino)-benzamide [(I), R1=R2=R3=H, R=3,5-difluorophenyl, Ar=4-(2-pyrrolidin-1-yl-ethoxy)-2-(tetrahydro-pyran-4-ylamino)-phenyl], cpd. 111

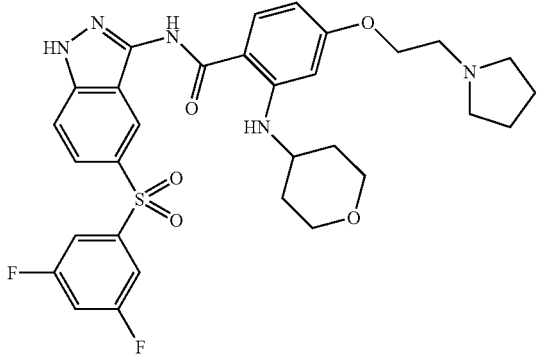

1H-NMR (400 MHz), δ (ppm, DMSO-d$_6$): 13.30 (bs, 1H), 10.61 (bs, 1H), 8.48 (m, 1H), 8.22 (d, J=7.7 Hz, 1H), 7.93-7.88 (m, 2H), 7.73 (m, 2H), 7.68 (d, J=8.9 Hz, 1H), 7.63 (m, 1H), 6.30 (d, J=2.3 Hz, 1H), 6.25 (dd, J1=8.8 Hz, J2=2.3 Hz, 1H), 4.14 (m, 2H), 3.83 (m, 2H), 3.70 (m, 1H), 3.51 (m, 2H), 2.81 (m, 2H), 2.54 (m, 4H), 1.96 (m, 2H), 1.70 (m, 4H), 1.38 (m, 2H).

N-[5-(3,5-Difluoro-benzenesulfonyl)-1H-indazol-3-yl]-4-(2-dimethylamino-ethoxy)-2-(tetrahydro-pyran-4-ylamino)-benzamide [(I), R1=R2=R3=H, R=3,5-difluorophenyl, Ar=4-(2-dimethylamino-ethoxy)-2-(tetrahydro-pyran-4-ylamino)-phenyl], cpd. 109

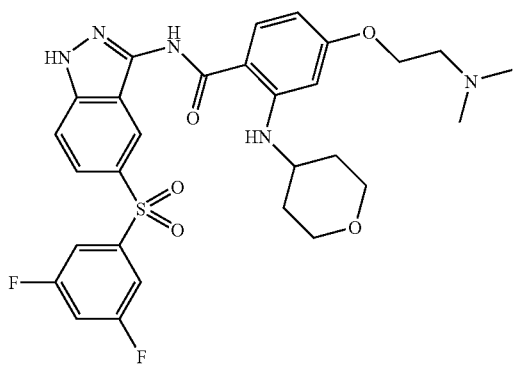

1H-NMR (400 MHz), δ (ppm, DMSO-d$_6$): 13.32 (bs, 1H), 10.62 (bs, 1H), 8.49 (m, 1H), 8.24 (d, J=7.6 Hz, 1H), 7.95-7.90 (m, 2H), 7.74 (m, 2H), 7.70 (d, J=8.9 Hz, 1H), 7.65 (m, 1H), 6.32 (d, J=2.3 Hz, 1H), 6.27 (dd, J1=8.9 Hz, J2=2.3 Hz, 1H), 4.14 (m, 2H), 3.84 (m, 2H), 3.71 (m, 1H), 3.52 (m, 2H), 2.65 (m, 2H), 2.25 (s, 6H), 1.98 (m, 2H), 1.41 (m, 2H).

N-[5-(3,5-Difluoro-benzenesulfonyl)-1H-indazol-3-yl]-4-{[2-(isopropyl-methyl-amino)-ethyl]-methyl-amino}-2-(tetrahydro-pyran-4-ylamino)-benzamide [(I), R1=R2=R3=H, R=3,5-difluorophenyl, Ar=4-{[2-(isopropyl-methyl-amino)-ethyl]-methyl-amino}-2-(tetrahydro-pyran-4-ylamino)-phenyl], cpd. 135

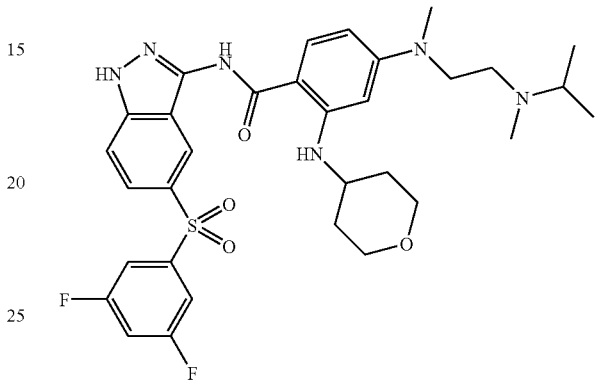

1H-NMR (400 MHz), δ (ppm, DMSO-d$_6$): 13.22 (bs, 1H), 10.34 (bs, 1H), 8.45 (m, 1H), 8.33 (d, J=7.3 Hz, 1H), 7.89 (dd, J1=8.9 Hz, J2=1.8 Hz, 1H), 7.79 (d, J=9.1 Hz, 1H), 7.71 (m, 2H), 7.65 (d, J=8.9 Hz, 1H), 7.62 (m, 1H), 6.03 (m, 1H), 5.88 (m, 1H), 3.83 (m, 2H), 3.64 (m, 1H), 3.51-3.38 (m, 4H), 2.99 (s, 3H), 2.77 (m, 1H), 2.50 (m, 2H), 2.22 (s, 3H), 1.98 (m, 2H), 1.40 (m, 2H), 0.93 (bd, 6H).

N-[5-(3,5-Difluoro-benzenesulfonyl)-1H-indazol-3-yl]-4-[methyl-(2-morpholin-4-yl-ethyl)-amino]-2-(tetrahydro-pyran-4-ylamino)-benzamide [(I), R1=R2=R3=H, R=3,5-difluorophenyl, Ar=4-[methyl-(2-morpholin-4-yl-ethyl)-amino]-2-(tetrahydro-pyran-4-ylamino)-phenyl], cpd. 139

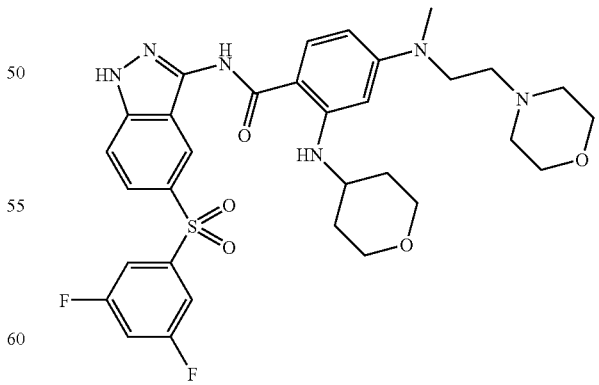

1H-NMR (400 MHz), δ (ppm, DMSO-d$_6$): 13.24 (bs, 1H), 10.37 (bs, 1H), 8.47 (m, 1H), 8.35 (d, J=7.4 Hz, 1H), 7.92 (dd, J1=8.9 Hz, J2=1.8 Hz, 1H), 7.82 (d, J=9.1 Hz, 1H), 7.73 (m, 2H), 7.66 (d, J=9.0 Hz, 1H), 7.64 (m, 1H), 6.07 (m, 1H), 5.90

(m, 1H), 3.85 (m, 2H), 3.68 (m, 1H), 3.60 (m, 4H), 3.57-3.46 (m, 4H), 3.01 (s, 3H), 2.50-2.42 (m, 6H), 2.00 (m, 2H), 1.42 (m, 2H).

N-[5-(3,5-Difluoro-benzenesulfonyl)-1H-indazol-3-yl]-4-[(3-dimethylamino-propyl)-methyl-amino]-2-(tetrahydro-pyran-4-ylamino)-benzamide [(I), R1=R2=R3=H, R=3,5-difluorophenyl, Ar=4-[(3-dimethylamino-propyl)-methyl-amino]-2-(tetrahydro-pyran-4-ylamino)-phenyl], cpd. 143

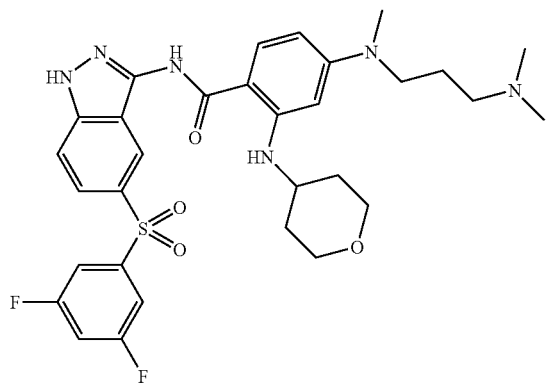

1H-NMR (400 MHz), δ (ppm, DMSO-d6): 13.23 (bs, 1H), 10.34 (bs, 1H), 8.46 (m, 1H), 8.33 (d, J=7.6 Hz, 1H), 7.90 (dd, J1=8.9 Hz, J2=1.8 Hz, 1H), 7.80 (d, J=9.1 Hz, 1H), 7.71 (m, 2H), 7.66 (d, J=9.0 Hz, 1H), 7.63 (m, 1H), 6.07 (dd, J1=9.1 Hz, J2=2.3 Hz, 1H), 5.89 (d, J=2.3 Hz, 1H), 3.84 (m, 2H), 3.67 (m, 1H), 3.50 (m, 2H), 3.41 (m, 2H), 2.97 (s, 3H), 2.24 (m, 2H), 2.15 (s, 6H), 1.99 (m, 2H), 1.66 (m, 2H), 1.40 (m, 2H).

N-[5-(3,5-Difluoro-benzenesulfonyl)-1H-indazol-3-yl]-4-dimethylaminomethyl-2-(tetrahydro-pyran-4-ylamino)-benzamide [(I), R1=R2=R3=H, R=3,5-difluorophenyl, Ar=4-dimethylaminomethyl-2-(tetrahydro-pyran-4-ylamino)-phenyl], cpd. 115

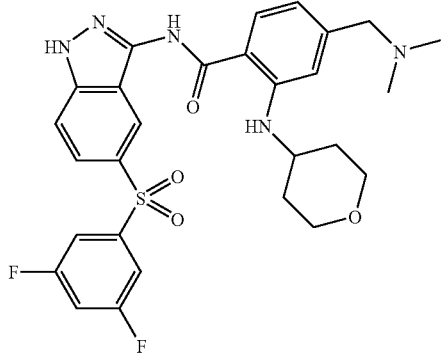

1H-NMR (400 MHz), δ (ppm, DMSO-d6): 13.33 (bs, 1H), 10.76 (bs, 1H), 8.50 (m, 1H), 7.95-7.90 (m, 2H), 7.88 (d, J=8.3 Hz, 1H), 7.72 (m, 2H), 7.69 (d, J=9.0 Hz, 1H), 7.63 (m, 1H), 6.78 (m, 1H), 6.59 (bd, J=8.3 Hz, 1H), 3.84 (m, 2H), 3.68 (m, 1H), 3.50 (m, 2H), 3.38 (bs, 2H), 2.18 (bs, 6H), 1.96 (m, 2H), 1.39 (m, 2H).

N-[5-(3,5-Difluoro-benzenesulfonyl)-1H-indazol-3-yl]-4-(1-methyl-piperidin-4-yloxy)-2-(tetrahydro-pyran-4-ylamino)-benzamide [(I), R1=R2=R3=H, R=3,5-difluorophenyl, Ar=4-(1-methyl-piperidin-4-yloxy)-2-(tetrahydro-pyran-4-ylamino)-phenyl], cpd. 113

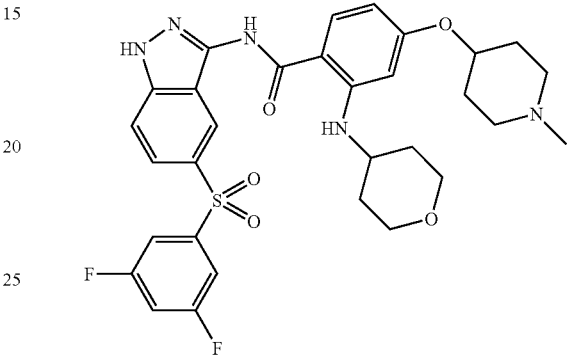

1H-NMR (400 MHz), δ (ppm, DMSO-d6): 13.31 (bs, 1H), 10.62 (bs, 1H), 8.48 (m, 1H), 8.19 (d, J=7.7 Hz, 1H), 7.94-7.88 (m, 2H), 7.73 (m, 2H), 7.69 (d, J=8.9 Hz, 1H), 7.64 (m, 1H), 6.28 (m, 2H), 4.50 (m, 1H), 3.83 (m, 2H), 3.68 (m, 1H), 3.51 (m, 2H), 2.63 (m, 2H), 2.26-2.18 (m, 5H), 1.95 (m, 4H), 1.67 (m, 2H), 1.39 (m, 2H).

N-[5-(3,5-Difluoro-benzenesulfonyl)-1H-indazol-3-yl]-2-(2-methoxy-1-methoxymethyl-ethylamino)-4-(4-methyl-piperazin-1-yl)-benzamide [(I), R1=R2=R3=H, R=3,5-difluorophenyl, Ar=4-(4-methyl-piperazin-1-yl)-2-(2-methoxy-1-methoxymethyl-ethylamino)-phenyl], cpd. 183

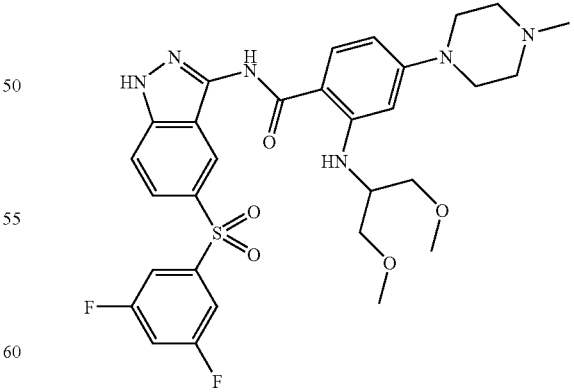

1H-NMR (400 MHz), δ (ppm, DMSO-d6): 13.25 (bs, 1H), 10.42 (bs, 1H), 8.47 (m, 1H), 8.31 (bd, J=8.3 Hz, 1H), 7.89 (dd, J1=8.9 Hz, J2=1.7 Hz, 1H), 7.79 (d, J=9.1 Hz, 1H), 7.70 (m, 2H), 7.66 (d, J=8.9 Hz, 1H), 7.62 (m, 1H), 6.27 (dd, J1=9.0 Hz, J2=2.2 Hz, 1H), 6.19 (d, J=2.2 Hz, 1H), 3.86 (m, 1H), 3.43 (d, J=5.0 Hz, 4H), 3.30 (m, 4H), 3.28 (s, 6H), 2.49 (m, 4H), 2.26 (bs, 3H).

N-[5-(3,5-Difluoro-benzenesulfonyl)-1H-indazol-3-yl]-4-[(2-dimethylamino-ethyl)-methyl-amino]-2-(2-methoxy-1-methoxymethyl-ethylamino)-benzamide [(I), R1=R2=R3=H, R=3,5-difluorophenyl, Ar=4-[(2-dimethylamino-ethyl)-methyl-amino]-2-(2-methoxy-1-methoxymethyl-ethylamino)-phenyl], cpd. 185

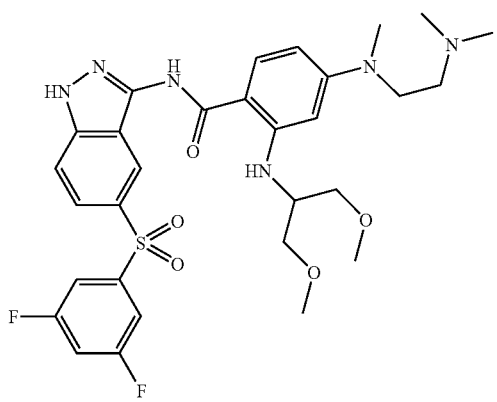

1H-NMR (400 MHz), δ (ppm, DMSO-d$_6$): 13.23 (bs, 1H), 10.33 (bs, 1H), 8.48 (m, 1H), 8.38 (bd, J=7.8 Hz, 1H), 7.89 (dd, J1=8.9 Hz, J2=1.8 Hz, 1H), 7.78 (d, J=9.1 Hz, 1H), 7.71 (m, 2H), 7.66 (d, J=9.5 Hz, 1H), 7.63 (m, 1H), 6.06 (dd, J1=9.1 Hz, J2=2.1 Hz, 1H), 5.93 (d, J=2.1 Hz, 1H), 3.80 (m, 1H), 3.53-3.44 (m, 6H), 3.29 (s, 6H), 2.50-2.40 (m, 2H), 2.99 (s, 3H), 2.26 (bs, 6H).

N-[5-(3,5-Difluoro-benzenesulfonyl)-1H-indazol-3-yl]-4-[(2-dimethylamino-ethyl)-methyl-amino]-2-(2-methoxy-1-methyl-ethylamino)-benzamide [(I), R1=R2=R3=H, R=3,5-difluorophenyl, Ar=4-[(2-dimethylamino-ethyl)-methyl-amino]-2-(2-methoxy-1-methyl-ethylamino)-phenyl], cpd. 160

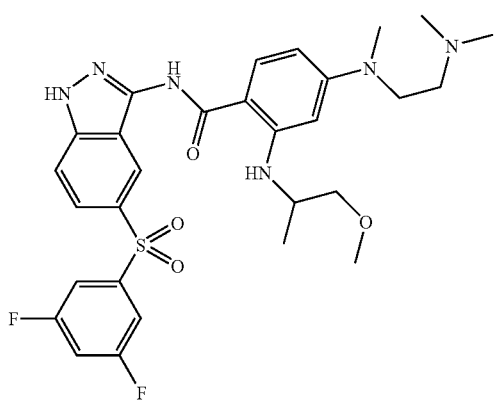

1H-NMR (400 MHz), δ (ppm, DMSO-d$_6$): 13.24 (bs, 1H), 10.33 (bs, 1H), 8.47 (m, 1H), 8.25 (d, J=7.7 Hz, 1H), 7.90 (dd, J1=8.9 Hz, J2=1.8 Hz, 1H), 7.79 (d, J=9.1 Hz, 1H), 7.73 (m, 2H), 7.67 (d, J=9.0 Hz, 1H), 7.64 (m, 1H), 6.05 (dd, J1=9.0 Hz, J2=2.3 Hz, 1H), 5.89 (d, J=2.3 Hz, 1H), 3.76 (m, 1H), 3.50 (m, 2H), 3.46-3.34 (m, 2H), 3.30 (s, 3H), 3.00 (s, 3H), 2.49 (m, 2H), 2.27 (bs, 6H), 1.19 (d, J=6.3 Hz, 3H).

N-[5-(3,5-Difluoro-benzenesulfonyl)-1H-indazol-3-yl]-4-[(3-dimethylamino-propyl)-methyl-amino]-2-(2-methoxy-1-methyl-ethylamino)-benzamide [(I), R1=R2=R3=H, R=3,5-difluorophenyl, Ar=4-[(3-dimethylamino-propyl)-methyl-amino]-2-(2-methoxy-1-methyl-ethylamino)-phenyl], cpd. 162

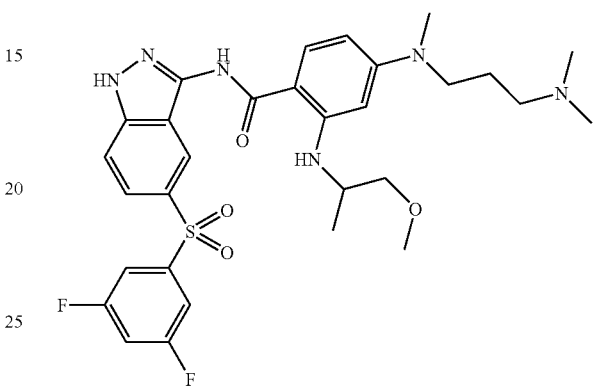

1H-NMR (400 MHz), δ (ppm, DMSO-d$_6$): 13.22 (bs, 1H), 10.31 (bs, 1H), 8.46 (m, 1H), 8.24 (d, J=7.6 Hz, 1H), 7.89 (dd, J1=8.9 Hz, J2=1.7 Hz, 1H), 7.77 (d, J=9.1 Hz, 1H), 7.71 (m, 2H), 7.66 (d, J=9.0 Hz, 1H), 7.63 (m, 1H), 6.06 (dd, J1=9.0 Hz, J2=2.2 Hz, 1H), 5.89 (d, J=2.2 Hz, 1H), 3.76 (m, 1H), 3.44-3.32 (m, 4H), 3.29 (s, 3H), 2.97 (s, 3H), 2.29 (m, 2H), 2.19 (bs, 6H), 1.69 (m, 2H), 1.18 (d, J=6.3 Hz, 3H).

N-[5-(3,5-Difluoro-benzenesulfonyl)-1H-indazol-3-yl]-4-dimethylaminomethyl-2-(2-methoxy-1-methyl-ethylamino)-benzamide [(I), R1=R2=R3=H, R=3,5-difluorophenyl, Ar=4-dimethylaminomethyl-2-(2-methoxy-1-methyl-ethylamino)-phenyl], cpd. 166

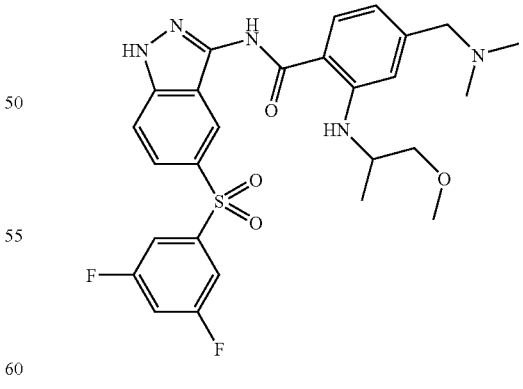

1H-NMR (400 MHz), δ (ppm, DMSO-d$_6$): 13.34 (bs, 1H), 10.74 (bs, 1H), 8.51 (m, 1H), 7.92 (dd, J1=8.9 Hz, J2=1.8 Hz, 1H), 7.89-784 (m, 2H), 7.73 (m, 2H), 7.70 (d, J=8.9 Hz, 1H), 7.64 (m, 1H), 6.77 (m, 1H), 6.58 (bd, J=8.0 Hz, 1H), 3.79 (m, 1H), 3.44-3.35 (m, 4H), 3.29 (s, 3H), 2.20 (bs, 6H), 1.18 (d, J=6.5 Hz, 3H).

N-[5-(3,5-Difluoro-benzenesulfonyl)-1H-indazol-3-yl]-4-[(3-dimethylamino-propyl)-methyl-amino]-2-isobutylamino-benzamide [(I), R1=R2=R3=H, R=3,5-difluorophenyl, Ar=4-[(3-dimethylamino-propyl)-methyl-amino]-2-isobutylamino-phenyl], cpd. 216

N-[5-(3,5-Difluoro-benzenesulfonyl)-1H-indazol-3-yl]-4-(4-methyl-[1,4]diazepan-1-yl)-2-(tetrahydro-pyran-4-ylamino)-benzamide trifluoroacetate [(I), R1=R2=R3=H, R=3,5-difluorophenyl, Ar=4-(4-methyl-[1,4]diazepan-1-yl)-2-(tetrahydro-pyran-4-ylamino)-phenyl], cpd. 105

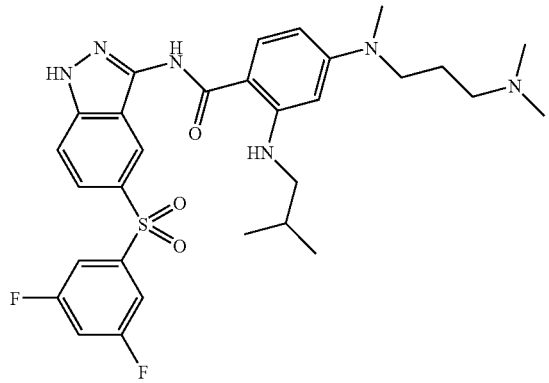

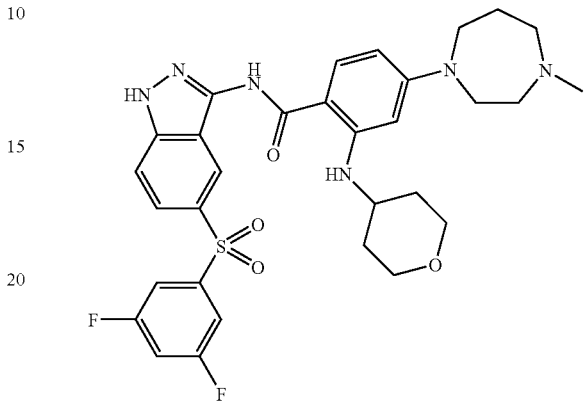

1H-NMR (400 MHz), δ (ppm, DMSO-$d_6$): 13.22 (bs, 1H), 10.35 (bs, 1H), 8.47 (m, 1H), 8.39 (bt, J=5.1 Hz, 1H), 7.90 (dd, J1=8.9 Hz, J2=1.8 Hz, 1H), 7.80 (d, J=9.1 Hz, 1H), 7.69 (m, 2H), 7.66 (d, J=8.9 Hz, 1H), 7.63 (m, 1H), 6.05 (dd, J1=9.0 Hz, J2=2.3 Hz, 1H), 5.80 (d, J=2.3 Hz, 1H), 3.41 (m, 2H), 3.01-2.95 (m, 5H), 2.26 (m, 2H), 2.17 (s, 6H), 1.91 (m, 1H), 1.67 (m, 2H), 0.98 (d, J=6.6 Hz, 6H).

1H-NMR (400 MHz), δ (ppm, DMSO-$d_6$): 13.28 (bs, 1H), 10.45 (bs, 1H), 9.57 (bs, 1H), 8.46 (m, 1H), 8.34 (bd, J=7.3 Hz, 1H), 7.92 (dd, J1=8.9 Hz, J2=1.7 Hz, 1H), 7.88 (d, J=9.2 Hz, 1H), 7.72 (m, 2H), 7.69 (d, J=8.9 Hz, 1H), 7.65 (m, 1H), 6.17 (m, 1H), 5.96 (m, 1H), 4.0-3.1 (m, 13H), 2.88 (s, 3H), 2.20 (m, 2H), 1.99 (m, 2H), 1.43 (m, 2H).

N-[5-(3,5-Difluoro-benzenesulfonyl)-1H-indazol-3-yl]-2-(2-methoxy-1-methyl-ethylamino)-4-(4-methyl-piperazin-1-yl)-benzamide [(I), R1=R2=R3=H, R=3,5-difluorophenyl, Ar=2-(2-methoxy-1-methyl-ethylamino)-4-(4-methyl-piperazin-1-yl)-phenyl], cpd. 158

Example 28

Preparation of N-[5-(3,5-difluoro-benzenesulfonyl)-1-trityl-1H-indazol-3-yl]-4-(4-methyl-piperazin-1-yl)-2-[(tetrahydro-pyran-4-yl)-(2,2,2-trifluoro-acetyl)-amino]-benzamide [(XVII), R1=R2=R3=H, R=3,5-difluorophenyl, R11=1-triphenylmethyl, Ar=4-(4-methyl-piperazin-1-yl)-2-[(tetrahydro-pyran-4-yl)-(2,2,2-trifluoro-acetyl)-amino]-phenyl]

To a suspension of 4-(4-methyl-piperazin-1-yl)-2-[(tetrahydro-pyran-4-yl)-(2,2,2-trifluoro-acetyl)-amino]-benzoic acid trifluoroacetate (2.16 g, 4.1 mmol) in dry dichloromethane (20 mL) were added oxalyl chloride (0.69 mL, 8.2 mmol) and N,N-dimethylformamide (1-2 drops). The mixture was stirred at room temperature for 1.5 hours then evaporated to dryness. The resulting crude acyl chloride was taken-up with toluene and evaporated again then dissolved in dry tetrahydrofuran (30 mL) and N,N-diisopropylethylamine (2.8 mL, 16.4 mmol) and treated with 5-(3,5-difluoro-benzenesulfonyl)-1-trityl-1H-indazol-3-ylamine (1.5 g, 2.72 mmol). The mixture was stirred at room temperature overnight then evaporated to dryness. The residue was dissolved in dichloromethane, washed with saturated solution of sodium hydrogenocarbonate and with brine, dried over sodium sulfate and evaporated to dryness. The crude was purified by flash chromatography on silica gel using dichloromethane/acetone 1:1 as the eluant, affording the title compound as a pale yellow solid (2.4 g, 93% yield).

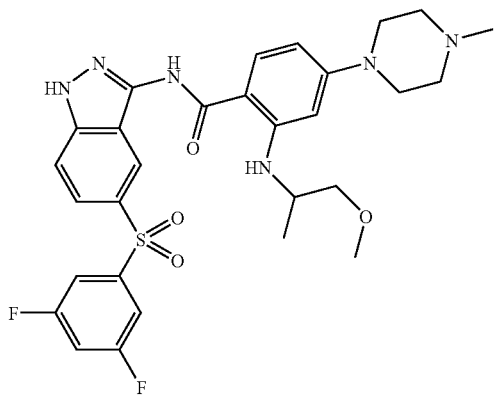

1H-NMR (400 MHz), δ (ppm, DMSO-$d_6$): 13.25 (bs, 1H), 10.42 (bs, 1H), 8.47 (m, 1H), 8.19 (d, J=7.8 Hz, 1H), 7.89 (dd, J1=8.9 Hz, J2=1.8 Hz, 1H), 7.80 (d, J=9.1 Hz, 1H), 7.72 (m, 2H), 7.66 (d, J=9.0 Hz, 1H), 7.62 (m, 1H), 6.26 (dd, J1=9.1 Hz, J2=2.3 Hz, 1H), 6.14 (d, J=2.3 Hz, 1H), 3.82 (m, 1H), 3.42-3.27 (m, 6H), 3.29 (s, 3H), 2.45 (m, 4H), 2.23 (s, 3H), 1.16 (d, J=6.4 Hz, 3H).

ESI (+) MS: m/z 949 (MH$^+$).

Operating in an analogous way, the following compounds were obtained:

N-[5-(3-Fluoro-benzenesulfonyl)-1-trityl-1H-indazol-3-yl]-4-nitro-2-[(tetrahydro-pyran-4-yl)-(2,2,2-trifluoro-acetyl)-amino]-benzamide [(XVII), R1=R2=R3=H, R=3-fluorophenyl, R11=1-triphenylmethyl, Ar=4-nitro-2-[(tetrahydro-pyran-4-yl)-(2,2,2-trifluoro-acetyl)-amino]-phenyl]

ESI (+) MS: m/z 878 (MH$^+$).

N-[5-(3,5-Difluoro-benzenesulfonyl)-1-trityl-1H-indazol-3-yl]-4-nitro-2-[(tetrahydro-pyran-4-yl)-(2,2,2-trifluoro-acetyl)-amino]-benzamide [(XVII), R1=R2=R3=H, R=3,5-difluorophenyl, R11=1-triphenylmethyl, Ar=4-nitro-2-[(tetrahydro-pyran-4-yl)-(2,2,2-trifluoro-acetyl)-amino]-phenyl]

1H-NMR (400 MHz), δ (ppm, DMSO-d$_6$): 11.76 (bs, 1H), 8.47 (m, 1H), 8.36 (m, 1H), 8.22 (m, 1H), 7.77-7.55 (m, 5H), 7.39-7.13 (m, 15H), 6.58 (m, 1H), 4.55 (m, 1H), 3.84 (m, 1H), 3.66 (m, 1H), 3.40-3.26 (m, 2H), 1.91 (m, 1H), 1.66 (m, 1H), 1.42 (m, 2H).

4-[(2-Dimethylamino-ethyl)-methyl-amino]-N-[5-(3-fluoro-benzenesulfonyl)-1-trityl-1H-indazol-3-yl]-2-[(tetrahydro-pyran-4-yl)-(2,2,2-trifluoro-acetyl)-amino]-benzamide [(XVII), R1=R2=R3=H, R=3-fluorophenyl, R11=1-triphenylmethyl, Ar=4-[(2-dimethylamino-ethyl)-methyl-amino]-2-[(tetrahydro-pyran-4-yl)-(2,2,2-trifluoro-acetyl)-amino]-phenyl]

1H-NMR (400 MHz), δ (ppm, DMSO-d$_6$): 10.91 (bs, 1H), 8.29 (m, 1H), 7.83 (m, 1H), 7.79-7.71 (m, 2H), 7.66 (m, 1H), 7.62 (m, 1H), 7.56 (m, 1H), 7.35-7.17 (m, 15H), 6.78 (dd, J1=8.9 Hz, J2=2.3 Hz, 1H), 6.61 (d, J=2.3 Hz, 1H), 6.52 (d, J=9.1 Hz, 1H), 4.50 (m, 1H), 3.86 (m, 1H), 3.77 (m, 1H), 3.54 (m, 2H), 3.38 (m, 2H), 3.02 (s, 3H), 2.43 (m, 2H), 2.21 (s, 6H), 1.93 (m, 1H), 1.66 (m, 1H), 1.53 (m, 1H), 1.31 (m, 1H).

N-[5-(3-Fluoro-benzenesulfonyl)-1-trityl-1H-indazol-3-yl]-4-(4-methyl-piperazin-1-yl)-2-[(tetrahydro-pyran-4-yl)-(2,2,2-trifluoro-acetyl)-amino]-benzamide [(XVII), R1=R2=R3=H, R=3-fluorophenyl, R11=1-triphenylmethyl, Ar=4-(4-methyl-piperazin-1-yl)-2-[(tetrahydro-pyran-4-yl)-(2,2,2-trifluoro-acetyl)-amino]-phenyl]

ESI (+) MS: m/z 931 (MH$^+$).

N-[5-(3,5-Difluoro-benzenesulfonyl)-1-trityl-1H-indazol-3-yl]-4-piperidin-1-ylmethyl-2-[(tetrahydro-pyran-4-yl)-(2,2,2-trifluoro-acetyl)-amino]-benzamide [(XVII), R1=R2=R3=H, R=3,5-difluorophenyl, R11=1-triphenylmethyl, Ar=4-piperidin-1-ylmethyl-2-[(tetrahydro-pyran-4-yl)-(2,2,2-trifluoro-acetyl)-amino]-phenyl]

1H-NMR (400 MHz), δ (ppm, DMSO-d$_6$): 11.34 (bs, 1H), 8.38 (m, 1H), 7.91 (m, 1H), 7.71-7.62 (m, 5H), 7.53 (m, 1H), 7.37-7.16 (m, 15H), 6.55 (d, J=9.6 Hz, 1H), 4.54 (m, 1H), 3.84 (m, 1H), 3.69 (m, 1H), 3.34-3.27 (m, 4H), 2.33 (m, 4H), 1.86 (m, 1H), 1.62 (m, 1H), 1.55-1.22 (m, 8H).

N-[5-(3,5-Difluoro-benzenesulfonyl)-1-trityl-1H-indazol-3-yl]-4-(4-pyrrolidin-1-yl-piperidin-1-yl)-2-[(tetrahydro-pyran-4-yl)-(2,2,2-trifluoro-acetyl)-amino]-benzamide [(XVII), R1=R2=R3=H, R=3,5-difluorophenyl, R11=1-triphenylmethyl, Ar=4-(4-pyrrolidin-1-yl-piperidin-1-yl)-2-[(tetrahydro-pyran-4-yl)-(2,2,2-trifluoro-acetyl)-amino]-phenyl]

ESI (+) MS: m/z 1003 (MH$^+$).

4-[(3-Dimethylamino-propyl)-methyl-amino]-N-[5-(3-fluoro-benzenesulfonyl)-1-trityl-1H-indazol-3-yl]-2-[(tetrahydro-pyran-4-yl)-(2,2,2-trifluoro-acetyl)-amino]-benzamide [(XVII), R1=R2=R3=H, R=3-fluorophenyl, R11=1-triphenylmethyl, Ar=4-[(3-dimethylamino-propyl)-methyl-amino]-2-[(tetrahydro-pyran-4-yl)-(2,2,2-trifluoro-acetyl)-amino] phenyl]

ESI (+) MS: m/z 947 (MH$^+$).

N-[5-(3-Fluoro-5-methoxy-benzenesulfonyl)-1-trityl-1H-indazol-3-yl]-4-(4-methyl-piperazin-1-yl)-2-[(tetrahydro-pyran-4-yl)-(2,2,2-trifluoro-acetyl)-amino]-benzamide [(XVII), R1=R2=R3=H, R=3-fluoro-5-methoxy-phenyl, R11=1-triphenylmethyl, Ar=4-(4-methyl-piperazin-1-yl)-2-[(tetrahydro-pyran-4-yl)-(2,2,2-trifluoro-acetyl)-amino]-phenyl]

ESI (+) MS: m/z 961 (MH$^+$).

N-[5-(3,5-Difluoro-benzenesulfonyl)-1-trityl-1H-indazol-3-yl]-2-[(2-methoxy-ethyl)-(2,2,2-trifluoro-acetyl)-amino]-4-(4-methyl-piperazin-1-yl)-benzamide [(XVII), R1=R2=R3=H, R=3,5-difluorophenyl, R11=1-triphenylmethyl, Ar=2-[(2-methoxy-ethyl)-(2,2,2-trifluoro-acetyl)-amino]-4-(4-methyl-piperazin-1-yl)-phenyl]

1H-NMR (400 MHz), δ (ppm, DMSO-d$_6$): 10.96 (bs, 1H), 8.32 (m, 1H), 7.85 (m, 1H), 7.74-7.62 (m, 4H), 7.39-7.12 (m, 15H), 7.03 (m, 1H), 6.98 (m, 1H), 6.51 (d, J=9.5 Hz, 1H), 3.69-3.41 (m, 4H), 3.30 (m, 4H), 3.14 (s, 3H), 2.47 (m, 4H), 2.24 (bs, 3H).

N-[5-(3,5-Difluoro-benzenesulfonyl)-1-trityl-1H-indazol-3-yl]-4-[(2-dimethylamino-ethyl)-methyl-amino]-2-[(2-methoxy-ethyl)-(2,2,2-trifluoro-acetyl)-amino]-benzamide [(XVII), R1=R2=R3=H, R=3,5-difluorophenyl, R11=1-triphenylmethyl, Ar=2-[(2-methoxy-ethyl)-(2,2,2-trifluoro-acetyl)-amino]-4-[(2-dimethylamino-ethyl)-methyl-amino]-phenyl]

ESI (+) MS: m/z 925 (MH$^+$).

N-[5-(3,5-Difluoro-benzenesulfonyl)-1-trityl-1H-indazol-3-yl]-2-[((S)-2-methoxy-1-methyl-ethyl)-(2,2,2-trifluoro-acetyl)-amino]-4-(4-methyl-piperazin-1-yl)-benzamide [(XVII), R1=R2=R3=H, R=3,5-difluorophenyl, R11=1-triphenylmethyl, Ar=4-(4-methyl-piperazin-1-yl)-2-[((S)-2-methoxy-1-methyl-ethyl)-(2,2,2-trifluoro-acetyl)-amino]-phenyl]

ESI (+) MS: m/z 937 (MH$^+$).

N-[5-(3,5-Difluoro-benzenesulfonyl)-1-trityl-1H-indazol-3-yl]-2-[((R)-2-methoxy-1-methyl-ethyl)-(2,2,2-trifluoro-acetyl)-amino]-4-(4-methyl-piperazin-1-yl)-benzamide [(XVII), R1=R2=R3=H, R=3,5-difluorophenyl, R11=1-triphenylmethyl, Ar=4-(4-methyl-piperazin-1-yl)-2-[((R)-2-methoxy-1-methyl-ethyl)-(2,2,2-trifluoro-acetyl)-amino]-phenyl]

ESI (+) MS: m/z 937 (MH+).

N-[5-(3,5-Difluoro-benzenesulfonyl)-1-trityl-1H-indazol-3-yl]-3-[(tetrahydro-pyran-4-yl)-(2,2,2-trifluoro-acetyl)-amino]-isonicotinamide [(XVII), R1=R2=R3=H, R=3,5-difluorophenyl, R11=1-triphenylmethyl, Ar=3-[(tetrahydro-pyran-4-yl)-(2,2,2-trifluoro-acetyl)-amino]-pyridin-4-yl]

1H-NMR (400 MHz), δ (ppm, DMSO-$d_6$): 11.72 (bs, 1H), 8.87 (d, J=4.9 Hz, 1H), 8.75 (s, 1H), 8.45 (m, 1H), 7.96 (d, J=4.9 Hz, 1H), 7.73-7.62 (m, 4H), 7.36-7.17 (m, 15H), 6.57 (d, J=9.4 Hz, 1H), 4.54 (m, 1H), 3.84 (m, 1H), 3.67 (m, 1H), 3.39 (m, 1H), 3.37-3.30 (m, 1H), 1.87 (m, 1H), 1.66 (m, 1H), 1.38 (m, 2H).

N-[5-(3,5-Difluoro-benzenesulfonyl)-1-trityl-1H-indazol-3-yl]-3-[(2-methoxy-1-methyl-ethyl)-(2,2,2-trifluoro-acetyl)-amino]isonicotinamide [(XVII), R1=R2=R3=H, R=3,5-difluorophenyl, R11=1-triphenylmethyl, Ar=3-[(2-methoxy-1-methyl-ethyl)-(2,2,2-trifluoro-acetyl)-amino]-pyridin-4-yl]

1H-NMR (400 MHz), δ (ppm, DMSO-$d_6$): 11.71, 11.61 (2bs, 1H), 8.87, 8.84 (2d, 1H), 8.73, 8.65 (2m, 1H), 8.48, 8.46 (2s, 1H), 7.94 (m, 1H), 7.74-7.62 (m, 4H), 7.38-7.13 (m, 15H), 6.60-6.53 (m, 1H), 4.78, 4.56 (2m, 1H), 3.45-3.23 (m, 2H), 3.21, 2.93 (2s, 3H), 1.19, 0.98 (2d, 3H), mixture of rotamers.

Example 29

Preparation of N-[5-(3,5-difluoro-benzenesulfonyl)-1H-indazol-3-yl]-4-(4-methyl-piperazin-1-yl)-2-[(tetrahydro-pyran-4-yl)-(2,2,2-trifluoro-acetyl)-amino]-benzamide [(I), R1=R2=R3=H, R=3,5-difluorophenyl, Ar=4-(4-methyl-piperazin-1-yl)-2-[(tetrahydro-pyran-4-yl)-(2,2,2-trifluoro-acetyl)-amino]-phenyl]

A mixture of N-[5-(3,5-difluoro-benzenesulfonyl)-1-trityl-1H-indazol-3-yl]-4-(4-methyl-piperazin-1-yl)-2-[(tetrahydro-pyran-4-yl)-(2,2,2-trifluoro-acetyl)-amino]-benzamide (2.4 g, 2.53 mmol), 4N hydrochloric acid in 1,4-dioxane (35 mL), methanol (50 mL) and 1,4-dioxane (15 mL) was stirred at room temperature for 3 hours. The solvents were removed under reduced pressure and the residue dissolved in dichloromethane, washed with water, brine, dried over sodium sulfate and evaporated to dryness. The crude was purified by flash chromatography on silica gel using dichloromethane/acetone 1:1 as the eluant affording the title compound as a pale yellow solid (1.43 g, 80% yield).

ESI (+) MS: m/z 707 (MH+).

Operating in an analogous way, the following compounds were obtained:

N-[5-(3-Fluoro-benzenesulfonyl)-1H-indazol-3-yl]-4-nitro-2-[(tetrahydro-pyran-4-yl)-(2,2,2-trifluoro-acetyl)-amino]-benzamide [(I), R1=R2=R3=H, R=3-fluorophenyl, Ar=4-nitro-2-[(tetrahydro-pyran-4-yl)-(2,2,2-trifluoro-acetyl)-amino]-phenyl]

1H-NMR (400 MHz), δ (ppm, DMSO-$d_6$): 13.45 (bs, 1H), 11.65 (bs, 1H), 8.57-8.51 (m, 2H), 8.40 (d, J=8.3 Hz, 1H), 8.28 (d, J=8.5 Hz, 1H), 7.91 (dd, J1=8.9 Hz, J2=1.7 Hz, 1H), 7.82-7.65 (m, 4H), 7.56 (m, 1H), 4.57 (m, 1H), 3.88 (m, 1H), 3.76 (m, 1H), 3.45-3.25 (m, 2H), 1.96 (m, 1H), 1.71 (m, 1H), 1.47 (m, 2H).

4-[(2-Dimethylamino-ethyl)-methyl-amino]-N-[5-(3-fluoro-benzenesulfonyl)-1H-indazol-3-yl]-2-[(tetrahydro-pyran-4-yl)-(2,2,2-trifluoro-acetyl)-amino]-benzamide hydrochloride [(I), R1=R2=R3=H, R=3-fluorophenyl, Ar=4-[(2-dimethylamino-ethyl)-methyl-amino]-2-[(tetrahydro-pyran-4-yl)-(2,2,2-trifluoro-acetyl)-amino]-phenyl]

1H-NMR (400 MHz), δ (ppm, DMSO-$d_6$): 13.31 (bs, 1H), 10.93 (bs, 1H), 10.39 (bs, 1H), 8.39 (m, 1H), 7.90 (d, J=8.9 Hz, 1H), 7.87 (dd, J1=8.9 Hz, J2=1.8 HZ, 1H), 7.77 (m, 1H), 7.73 (m, 1H), 7.70-7.63 (m, 2H), 7.55 (m, 1H), 7.00 (dd, J1=8.9 Hz, J2=2.6 Hz, 1H), 6.77 (d, J=2.6 Hz, 1H), 4.50 (m, 1H), 3.85 (m, 4H), 3.39 (m, 2H), 3.23 (m, 2H), 3.05 (s, 3H), 2.84 (s, 6H), 1.98 (m, 1H), 1.69 (m, 1H), 1.53 (m, 1H), 1.34 (m, 1H).

N-[5-(3-Fluoro-benzenesulfonyl)-1H-indazol-3-yl]-4-(4-methyl-piperazin-1-yl)-2-[(tetrahydro-pyran-4-yl)-(2,2,2-trifluoro-acetyl)-amino]-benzamide hydrochloride [(I), R1=R2=R3=H, R=3-fluorophenyl, Ar=4-(4-methyl-piperazin-1-yl)-2-[(tetrahydro-pyran-4-yl)-(2,2,2-trifluoro-acetyl)-amino]-phenyl]

ESI (+) MS: m/z 689 (MH+).

N-[5-(3,5-Difluoro-benzenesulfonyl)-1H-indazol-3-yl]-4-piperidin-1-ylmethyl-2-[(tetrahydro-pyran-4-yl)-(2,2,2-trifluoro-acetyl)-amino]-benzamide hydrochloride [(I), R1=R2=R3=H, R=3,5-difluorophenyl, Ar=4-piperidin-1-ylmethyl-2-[(tetrahydro-pyran-4-yl)-(2,2,2-trifluoro-acetyl)-amino]-phenyl]

1H-NMR (400 MHz), δ (ppm, DMSO-$d_6$): 13.44 (bs, 1H), 11.38 (bs, 1H), 10.52 (bs, 1H), 8.47 (m, 1H), 8.09 (bd, J=8.0 Hz, 1H), 7.94 (dd, J1=8.9, Hz, J2=1.8 Hz, 1H), 7.90 (bd, 1H), 7.78 (m, 1H), 7.71 (d, J=9.7 Hz, 1H), 7.69-7.62 (m, 3H), 4.54 (m, 1H), 4.45 (bd, 2H), 3.88 (m, 1H), 3.78 (m, 1H), 3.5-3.2 (m, 6H), 2.88 (m, 2H), 1.96-1.51 (m, 6H), 1.37 (m, 2H).

N-[5-(3,5-Difluoro-benzenesulfonyl)-1H-indazol-3-yl]-4-(4-pyrrolidin-1-yl-piperidin-1-yl)-2-[(tetrahydro-pyran-4-yl)-(2,2,2-trifluoro-acetyl)-amino]-benzamide hydrochloride [(I), R1=R2=R3=H, R=3,5-difluorophenyl, Ar=4-(4-pyrrolidin-1-yl-piperidin-1-yl)-2-[(tetrahydro-pyran-4-yl)-(2,2,2-trifluoro-acetyl)-amino]-phenyl]

1H-NMR (400 MHz), δ (ppm, DMSO-$d_6$): 13.34 (bs, 1H), 10.98 (bs, 1H), 10.21 (bs, 1H), 8.40 (m, 1H), 7.94-7.83 (m, 2H), 7.73-7.59 (m, 4H), 7.16 (dd, J1=8.8 Hz, J2=2.6 Hz, 1H), 6.98 (d, J=2.6 Hz, 1H), 4.49 (m, 1H), 4.08 (m, 2H), 3.82 (m, 2H), 3.54 (m, 4H), 3.30 (m, 1H), 3.09 (m, 2H), 2.89 (m, 2H), 2.2-1.2 (m, 12H).

4-[(3-Dimethylamino-propyl)-methyl-amino]-N-[5-(3-fluoro-benzenesulfonyl)-1H-indazol-3-yl]-2-[(tetrahydro-pyran-4-yl)-(2,2,2-trifluoro-acetyl)-amino]-benzamide hydrochloride [(I), R1=R2=R3=H, R=3-fluorophenyl, Ar=4-[(3-dimethylamino-propyl)-methyl-amino]-2-[(tetrahydro-pyran-4-yl)-(2,2,2-trifluoro-acetyl)-amino]-phenyl]

ESI (+) MS: m/z 705 (MH+).

N-[5-(3-Fluoro-5-methoxy-benzenesulfonyl)-1H-indazol-3-yl]-4-(4-methyl-piperazin-1-yl)-2-[(tetrahydro-pyran-4-yl)-(2,2,2-trifluoro-acetyl)-amino]-benzamide hydrochloride [(I), R1=R2=R3=H, R=3-fluoro-5-methoxy-phenyl, Ar=4-(4-methyl-piperazin-1-yl)-2-[(tetrahydro-pyran-4-yl)-(2,2,2-trifluoro-acetyl)-amino]-phenyl]

ESI (+) MS: m/z 719 (MH+).

N-[5-(3,5-Difluoro-benzenesulfonyl)-1H-indazol-3-yl]-2-[(2-methoxy-ethyl)-(2,2,2-trifluoro-acetyl)-amino]-4-(4-methyl-piperazin-1-yl)-benzamide hydrochloride [(I), R1=R2=R3=H, R=3,5-difluorophenyl, Ar=2-[(2-methoxy-ethyl)-(2,2,2-trifluoro-acetyl)-amino]-4-(4-methyl-piperazin-1-yl)-phenyl]

1H-NMR (400 MHz), δ (ppm, DMSO-d$_6$): 13.35 (bs, 1H), 10.98 (bs, 1H), 10.35 (bs, 1H), 8.46 (m, 1H), 7.96-7.91 (m, 2H), 7.71-7.62 (m, 4H), 7.19 (m, 1H), 7.12 (m, 1H), 4.13-4.00 (m, 2H), 3.59-3.48 (m, 2H), 3.34 (m, 4H), 3.22-3.14 (m, 7H), 2.87 (bd, 3H).

N-[5-(3,5-Difluoro-benzenesulfonyl)-1H-indazol-3-yl]-4-[(2-dimethylamino-ethyl)-methyl-amino]-2-[(2-methoxy-ethyl)-(2,2,2-trifluoro-acetyl)-amino]-benzamide hydrochloride [(I), R1=R2=R3=H, R=3,5-difluorophenyl, Ar=2-[(2-methoxy-ethyl)-(2,2,2-trifluoro-acetyl)-amino]-4-[(2-dimethylamino-ethyl)-methyl-amino]-phenyl]

ESI (+) MS: m/z 683 (MH+).

N-[5-(3,5-Difluoro-benzenesulfonyl)-1H-indazol-3-yl]-2-[((S)-2-methoxy-1-methyl-ethyl)-(2,2,2-trifluoro-acetyl)-amino]-4-(4-methyl-piperazin-1-yl)-benzamide hydrochloride [(I), R1=R2=R3=H, R=3,5-difluorophenyl, Ar=2-[((S)-2-methoxy-1-methyl-ethyl)-(2,2,2-trifluoro-acetyl)-amino]-4-(4-methyl-piperazin-1-yl)-phenyl]

ESI (+) MS: m/z 695 (MH+).

N-[5-(3,5-Difluoro-benzenesulfonyl)-1H-indazol-3-yl]-2-[((R)-2-methoxy-1-methyl-ethyl)-(2,2,2-trifluoro-acetyl)-amino]-4-(4-methyl-piperazin-1-yl)-benzamide hydrochloride [(I), R1=R2=R3=H, R=3,5-difluorophenyl, Ar=2-[((R)-2-methoxy-1-methyl-ethyl)-(2,2,2-trifluoro-acetyl)-amino]-4-(4-methyl-piperazin-1-yl)-phenyl]

ESI (+) MS: m/z 695 (MH+).

N-[5-(3,5-Difluoro-benzenesulfonyl)-1H-indazol-3-yl]-3-[(tetrahydro-pyran-4-yl)-(2,2,2-trifluoro-acetyl)-amino]-isonicotinamide hydrochloride [(I), R1=R2=R3=H, R=3,5-difluorophenyl, Ar=3-[(tetrahydro-pyran-4-yl)-(2,2,2-trifluoro-acetyl)-amino]-pyridin-4-yl]

1H-NMR (400 MHz), δ (ppm, DMSO-d$_6$): 13.50 (bs, 1H), 11.63 (bs, 1H), 8.94 (d, J=4.9 Hz, 1H), 8.80 (s, 1H), 8.55 (m, 1H), 8.01 (d, J=4.9 Hz, 1H), 7.96 (dd, J1=8.9 Hz, J2=1.8 Hz, 1H), 7.73 (d, J=8.9 Hz, 1H), 7.71-7.62 (m, 3H), 4.56 (m, 1H), 3.89 (m, 1H), 3.77 (m, 1H), 3.45-3.31 (m, 2H), 1.92 (m, 1H), 1.71 (m, 1H), 1.54-1.33 (m, 2H).

N-[5-(3,5-Difluoro-benzenesulfonyl)-1H-indazol-3-yl]-3-[(2-methoxy-1-methyl-ethyl)-(2,2,2-trifluoro-acetyl)-amino]-isonicotinamide hydrochloride [(I), R1=R2=R3=H, R=3,5-difluorophenyl, Ar=3-[(2-methoxy-1-methyl-ethyl)-(2,2,2-trifluoro-acetyl)-amino]-pyridin-4-yl]

ESI (+) MS: m/z 598 (MH+).

Example 30

Preparation of N-[5-(3,5-difluoro-benzenesulfonyl)-1H-indazol-3-yl]-4-[methyl-(2-piperidin-1-yl-ethyl)-amino]-2-nitro-benzamide hydrochloride [(I), R1=R2=R3=H, R=3,5-difluorophenyl, Ar=4-[methyl-(2-piperidin-1-yl-ethyl)-amino]-2-nitro-phenyl], cpd. 217

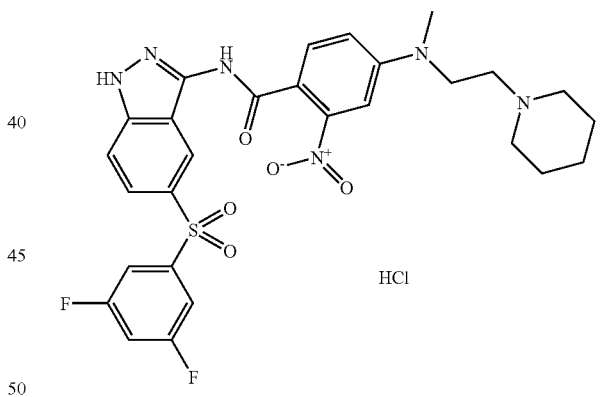

A solution of N-[5-(3,5-difluoro-benzenesulfonyl)-1-trityl-1H-indazol-3-yl]-4-[methyl-(2-piperidin-1-yl-ethyl)-amino]-2-nitro-benzamide (1.86 g, 2.21 mmol) in 1,4-dioxane (50 mL) was treated with 4N HCl in 1,4-dioxane (4.42 mL, 17.68 mmol). The mixture was stirred at room temperature for 30 hours then the volatiles were removed under reduced pressure. The residue was suspended in diethylether (100 mL), stirred for 1 hour, filtered, washed with diethylether and dried in oven at 40° C. affording the title compound as orange solid (1.29 g).

1H-NMR (400 MHz), δ (ppm, DMSO-d$_6$): 13.36 (bs, 1H), 11.23 (bs, 1H), 9.86 (bs, 1H), 8.61 (m, 1H), 7.91 (dd, J1=8.9, J2=1.8 Hz, 1H), 7.75 (m, 1H), 7.70-7.60 (m, 4H), 7.29 (d, J=2.5 Hz, 1H), 7.14 (dd, J1=9.0 Hz, J2=2.5 Hz, 1H), 3.88 (m, 2H), 3.50 (m, 2H), 3.22 (m, 2H), 3.07 (s, 3H), 2.95 (m, 2H), 1.89-1.63 (m, 5H), 1.40 (m, 1H).

Operating in an analogous way, the following compound was obtained:

N-[5-(3,5-Difluoro-benzenesulfonyl)-1H-indazol-3-yl]-4-(4-methyl-piperazin-1-yl)-benzamide hydrochloride [(I), R1=R2=R3=H, R=3,5-difluorophenyl, Ar=4-(4-methyl-piperazin-1-yl)-phenyl], cpd. 3

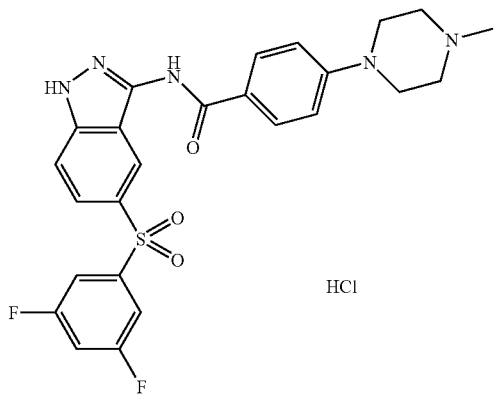

HCl

1H-NMR (400 MHz), δ (ppm, DMSO-d₆): 13.36 (bs, 1H), 10.88 (bs, 1H), 10.41 (bs, 1H), 8.63 (m, 1H), 8.07 (m, 2H), 7.91 (d, J1=8.9 Hz, J2=1.83 Hz, 1H), 7.72 (m, 2H), 7.69 (m, 1H), 7.64 (m, 1H), 7.14 (m, 2H), 4.09 (m, 2H), 3.53 (m, 2H), 3.25-3.13 (m, 4H), 2.85 (bd, J=4.6 Hz, 3H).

Example 31

Preparation of N-[5-(3,5-difluoro-benzenesulfonyl)-1H-indazol-3-yl]-4-(4-methyl-piperazin-1-yl)-2-(tetrahydro-pyran-4-ylamino)-benzamide [(I), R1=R2=R3=H, R=3,5-difluorophenyl, Ar=4-(4-methyl-piperazin-1-yl)-2-(tetrahydro-pyran-4-ylamino)-phenyl], cpd. 12

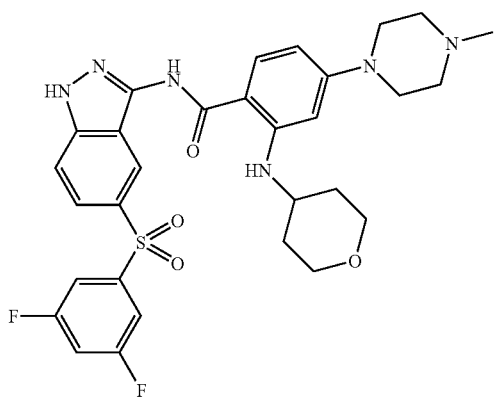

A mixture of N-[5-(3,5-difluoro-benzenesulfonyl)-1H-indazol-3-yl]-4-(4-methyl-piperazin-1-yl)-2-[(tetrahydro-pyran-4-yl)-(2,2,2-trifluoro-acetyl)-amino]-benzamide (1.41 g, 2.0 mmol), triethylamine (5.6 mL) and methanol (30 mL) was stirred at room temperature overnight. The solvents were removed under reduced pressure and the residue treated with methanol (10 mL), stirred at 45° C. for 30 minutes, filtered and dried in oven affording 1.0 g of the title compound as a white solid (81% yield).

1H-NMR (400 MHz), δ (ppm, DMSO-d₆): 13.27 (bs, 1H), 10.47 (bs, 1H), 8.48 (d, J=1.1 Hz, 1H), 8.29 (d, J=7.8 Hz, 1H), 7.92 (dd, J1=8.90, J2=1.82 Hz, 1H), 7.82 (d, J=9.14 Hz, 1H), 7.73 (m, 2H), 7.68 (dd, J1=8.91 Hz, J2=0.74 Hz, 1H), 7.64 (m, 1H), 6.28 (dd, J1=9.0 Hz, J2=2.07 Hz, 1H), 6.07 (d, J=2.07 Hz, 1H), 3.83 (m, 2H), 3.74 (m, 1H), 3.53 (m, 2H), 3.27.3.34 (m, 4H), 2.46 (m, 4H), 2.25 (s, 3H), 1.97 (m, 2H), 1.39 (m, 2H).

Operating in an analogous way, the following compounds were obtained:

N-[5-(3-Fluoro-benzenesulfonyl)-1H-indazol-3-yl]-4-nitro-2-(tetrahydro-pyran-4-ylamino)-benzamide [(I), R1=R2=R3=H, R=3-fluorophenyl, Ar=4-nitro-2-(tetrahydro-pyran-4-ylamino)-phenyl], cpd. 218

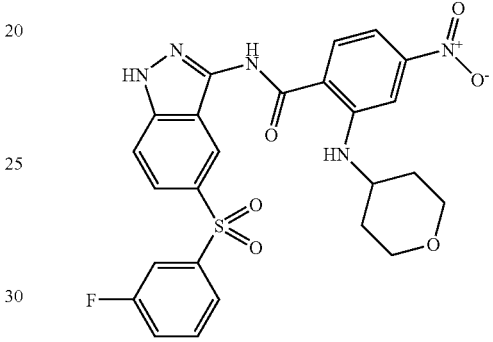

1H-NMR (400 MHz), δ (ppm, DMSO-d₆): 13.40 (bs, 1H), 12.00 (bs, 1H), 11.21 (bs, 1H), 8.55 (m, 1H), 8.10 (d, J=8.7 Hz, 1H), 7.89 (m, 1H), 7.83-7.78 (m, 2H), 7.75-7.62 (m, 2H), 7.56 (m, 2H), 7.42 (dd, J1=8.7 Hz, J2=2.3 Hz, 1H), 3.88-3.78 (m, 3H), 3.57-3.50 (m, 2H), 2.02-1.94 (m, 2H), 1.50-1.40 (m, 2H).

4-[(2-Dimethylamino-ethyl)-methyl-amino]-N-[5-(3-fluoro-benzenesulfonyl)-1H-indazol-3-yl]-2-(tetrahydro-pyran-4-ylamino)-benzamide [(I), R1=R2=R3=H, R=3-fluorophenyl, Ar=4-[(2-dimethylamino-ethyl)-methyl-amino]-2-(tetrahydro-pyran-4-ylamino)-phenyl], cpd. 132

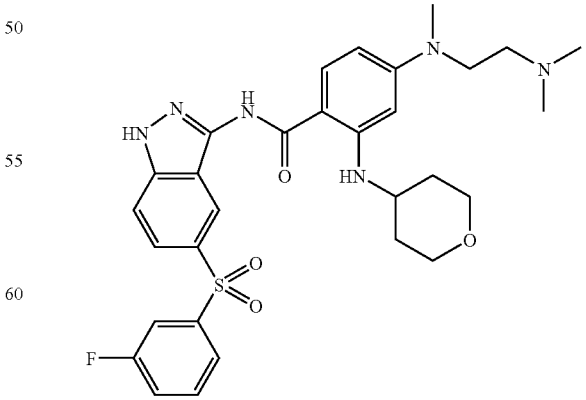

1H-NMR (400 MHz), δ (ppm, DMSO-d₆): 13.22 (bs, 1H), 10.35 (bs, 1H), 8.45 (m, 1H), 8.34 (d, J=7.3 Hz, 1H), 7.86 (dd, J1=8.9 Hz, J2=1.8 Hz, 1H), 7.84-7.78 (m, 3H), 7.70-7.63 (m, 2H), 7.55 (m, 1H), 6.06 (dd, J1=9.0 Hz, J2=2.1 Hz, 1H), 5.90 (d, J=2.1 Hz, 1H), 3.90-3.83 (m, 2H), 3.67 (m, 1H), 3.55-3.45 (m, 4H), 3.00 (s, 3H), 2.42 (m, 2H), 2.22 (s, 6H), 2.01 (m, 2H), 1.42 (m, 2H).

N-[5-(3-Fluoro-benzenesulfonyl)-1H-indazol-3-yl]-4-(4-methyl-piperazin-1-yl)-2-(tetrahydro-pyran-4-ylamino)-benzamide [(I), R1=R2=R3=H, R=3-fluorophenyl, Ar=4-(4-methyl-piperazin-1-yl)-2-(tetrahydro-pyran-4-ylamino)-phenyl], cpd. 11

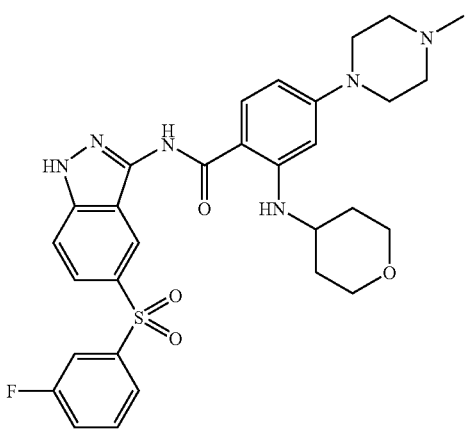

1H-NMR (400 MHz), δ (ppm, DMSO-d$_6$): 13.23 (bs, 1H), 10.45 (bs, 1H), 8.43 (m, 1H), 8.28 (d, J=7.8 Hz, 1H), 7.86 (dd, J1=8.9 Hz, J2=1.7 Hz, 1H), 7.83-7.76 (m, 3H), 7.69-7.62 (m, 2H), 7.53 (m, 1H), 6.27 (dd, J1=9.1 Hz, J2=2.1 Hz, 1H), 6.16 (d, J=2.1 Hz, 1H), 3.82 (m, 2H), 3.73 (m, 1H), 3.52 (m, 2H), 3.28 (m, 4H), 2.48 (m, 4H), 2.27 (s, 3H), 1.97 (m, 2H), 1.39 (m, 2H).

N-[5-(3,5-Difluoro-benzenesulfonyl)-1H-indazol-3-yl]-4-piperidin-1-ylmethyl-2-(tetrahydro-pyran-4-ylamino)-benzamide [(I), R1=R2=R3=H, R=3,5-difluorophenyl, Ar=4-piperidin-1-ylmethyl-2-(tetrahydro-pyran-4-ylamino)-phenyl], cpd. 119

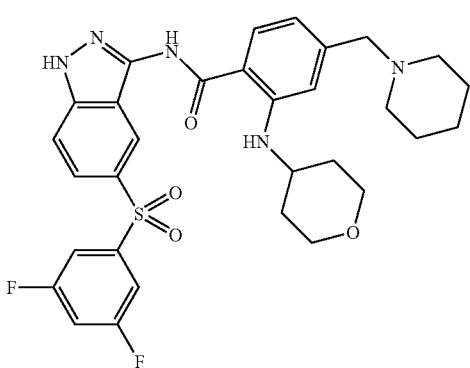

1H-NMR (400 MHz), δ (ppm, DMSO-d$_6$): 13.34 (bs, 1H), 10.75 (bs, 1H), 8.50 (m, 1H), 7.94-7.85 (m, 3H), 7.72 (m, 2H), 7.69 (d, J=9.0 Hz, 1H), 7.63 (m, 1H), 6.80 (m, 1H), 6.60 (m, 1H), 3.84 (m, 2H), 3.67 (m, 1H), 3.50 (m, 2H), 3.42 (bs, 2H), 2.35 (m, 4H), 1.97 (m, 2H), 1.62-1.34 (m, 8H).

N-[5-(3,5-Difluoro-benzenesulfonyl)-1H-indazol-3-yl]-4-(4-pyrrolidin-1-yl-piperidin-1-yl)-2-(tetrahydro-pyran-4-ylamino)-benzamide [(I), R1=R2=R3=H, R=3,5-difluorophenyl, Ar=4-(4-pyrrolidin-1-yl-piperidin-1-yl)-2-(tetrahydro-pyran-4-ylamino)-phenyl], cpd. 147

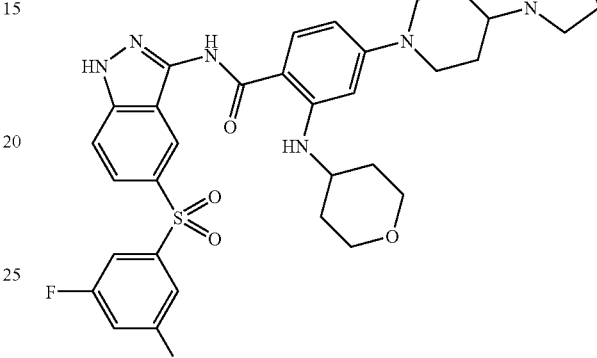

1H-NMR (400 MHz), δ (ppm, DMSO-d$_6$): 13.26 (bs, 1H), 10.44 (bs, 1H), 8.46 (m, 1H), 8.28 (bd, J=7.6 Hz, 1H), 7.90 (dd, J1=8.9 Hz, J2=1.8 Hz, 1H), 7.81 (d, J=9.1 Hz, 1H), 7.71 (m, 2H), 7.67 (d, J=8.9 Hz, 1H), 7.63 (m, 1H), 6.27 (m, 1H), 6.15 (m, 1H), 3.82 (m, 4H), 3.72 (m, 1H), 3.51 (m, 2H), 2.87 (m, 2H), 2.58 (m, 4H), 2.25 (m, 1H), 2.00-1.88 (m, 4H), 1.72 (m, 4H), 1.50 (m, 2H), 1.38 (m, 2H).

4-[(3-Dimethylamino-propyl)-methyl-amino]-N-[5-(3-fluoro-benzenesulfonyl)-1H-indazol-3-yl]-2-(tetrahydro-pyran-4-ylamino)-benzamide [(I), R1=R2=R3=H, R=3-fluorophenyl, Ar=4-[(3-dimethylamino-propyl)-methyl-amino]-2-(tetrahydro-pyran-4-ylamino)-phenyl], cpd. 142

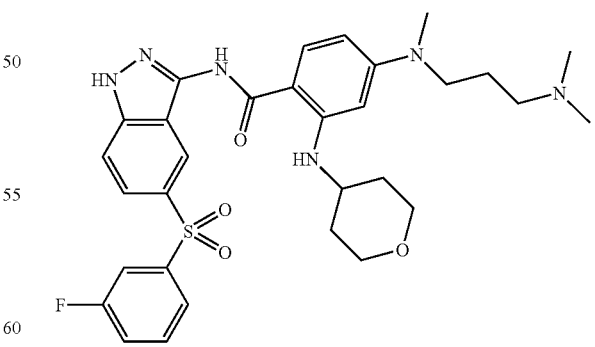

1H-NMR (400 MHz), δ (ppm, DMSO-d$_6$): 13.21 (bs, 1H), 10.34 (bs, 1H), 8.44 (m, 1H), 8.34 (bd, J=7.4 Hz, 1H), 7.86 (dd, J1=8.9 Hz, J2=1.8 Hz, 1H), 7.82-7.77 (m, 3H), 7.70-7.63 (m, 2H), 7.54 (m, 1H), 6.07 (dd, J1=8.9 Hz, J2=2.3 Hz, 1H), 5.90 (d, J=2.3 Hz, 1H), 3.85 (m, 2H), 3.68 (m, 1H), 3.51 (m, 2H), 3.42 (m, 2H), 2.98 (s, 3H), 2.25 (m, 2H), 2.17 (s, 6H), 2.00 (m, 2H), 1.67 (m, 2H), 1.42 (m, 2H).

N-[5-(3-Fluoro-5-methoxy-benzenesulfonyl)-1H-indazol-3-yl]-4-(4-methyl-piperazin-1-yl)-2-(tetrahydro-pyran-4-ylamino)-benzamide [(I), R1=R2=R3=H, R=3-fluoro-5-methoxy-phenyl, Ar=4-(4-methyl-piperazin-1-yl)-2-(tetrahydro-pyran-4-ylamino)-phenyl], cpd. 85

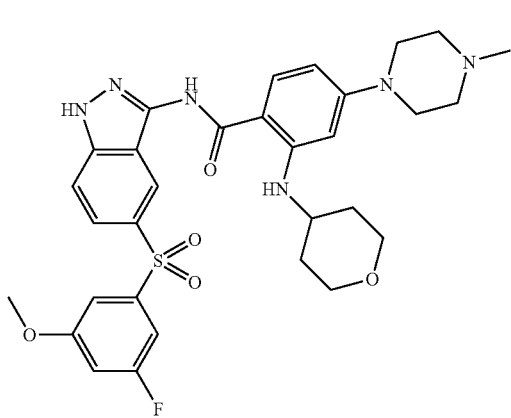

1H-NMR (400 MHz), δ (ppm, DMSO-d$_6$): 13.25 (bs, 1H), 10.47 (bs, 1H), 8.45 (m, 1H), 8.28 (bd, J=7.7 Hz, 1H), 7.89 (dd, J1=8.9 Hz, J2=1.8 Hz, 1H), 7.84 (d, J=9.1 Hz, 1H), 7.67 (d, J=8.9 Hz, 1H), 7.35 (m, 1H), 7.30 (m, 1H), 7.18 (m, 1H), 6.28 (dd, J1=9.1 Hz, J2=2.3 Hz, 1H), 6.17 (d, J=2.3 Hz, 1H), 3.88-3.81 (m, 5H), 3.74 (m, 1H), 3.53 (m, 2H), 3.32 (m, 4H), 2.53 (m, 4H), 2.29 (bs, 3H), 1.98 (m, 2H), 1.39 (m, 2H).

N-[5-(3,5-Difluoro-benzenesulfonyl)-1H-indazol-3-yl]-2-(2-methoxy-ethylamino)-4-(4-methyl-piperazin-1-yl)-benzamide [(I), R1=R2=R3=H, R=3,5-difluorophenyl, Ar=2-(2-methoxy-ethylamino)-4-(4-methyl-piperazin-1-yl)-phenyl], cpd. 150

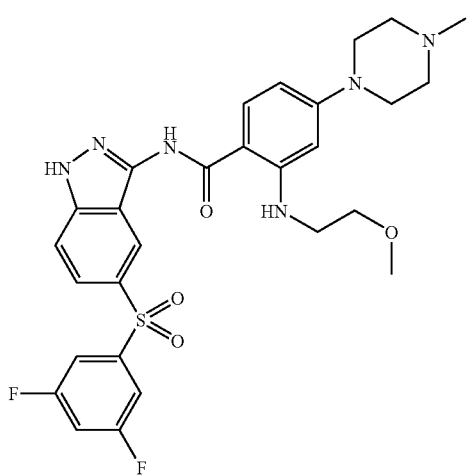

1H-NMR (400 MHz), δ (ppm, DMSO-d$_6$): 13.26 (bs, 1H), 10.45 (bs, 1H), 8.50 (d, J=1.2 Hz, 1H), 8.23 (bt, J=5.0 Hz, 1H), 7.90 (dd, J1=8.9, J2=1.8 Hz, 1H), 7.82 (d, J=9.1 Hz, 1H), 7.73 (m, 2H), 7.67 (dd, J1=8.9 Hz, J2=0.7 Hz, 1H), 7.64 (m, 1H), 6.29 (dd, J1=9.0 Hz, J2=2.3 Hz, 1H), 6.11 (d, J=2.3 Hz, 1H), 3.57 (bt, J=5.2 Hz, 2H), 3.36-3.30 (m, 6H), 3.30 (s, 3H), 2.48 (m, 4H), 2.29 (bs, 3H).

N-[5-(3,5-Difluoro-benzenesulfonyl)-1H-indazol-3-yl]-4-[(2-dimethylamino-ethyl)-methyl-amino]-2-(2-methoxy-ethylamino)-benzamide [(I), R1=R2=R3=H, R=3,5-difluorophenyl, Ar=2-(2-methoxy-ethylamino)-4-[(2-dimethylamino-ethyl)-methyl-amino]-phenyl], cpd. 152

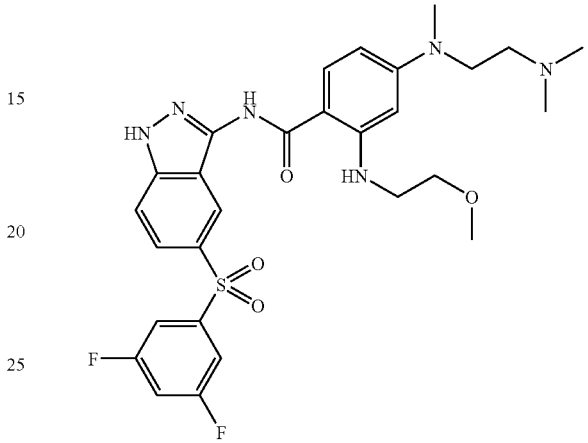

1H-NMR (400 MHz), δ (ppm, DMSO-d$_6$): 13.23 (bs, 1H), 10.34 (bs, 1H), 8.48 (d, J=1.2 Hz, 1H), 8.28 (bt, J=5.1 Hz, 1H), 7.89 (dd, J1=9.0 Hz, J2=1.8 Hz, 1H), 7.79 (d, J=9.1 Hz, 1H), 7.72 (m, 2H), 7.66 (dd, J1=8.9 Hz, J2=0.6 Hz, 1H), 7.62 (m, 1H), 6.06 (dd, J1=9.0 Hz, J2=2.2 Hz, 1H), 5.83 (d, J=2.2 Hz, 1H), 3.57 (bt, J=5.2 Hz, 2H), 3.51 (m, 2H), 3.32 (m, 2H), 3.29 (s, 3H), 2.99 (s, 3H), 2.52 (m, 2H), 2.28 (bs, 6H).

N-[5-(3,5-Difluoro-benzenesulfonyl)-1H-indazol-3-yl]-2-((S)-2-methoxy-1-methyl-ethylamino)-4-(4-methyl-piperazin-1-yl)-benzamide [(I), R1=R2=R3=H, R=3,5-difluorophenyl, Ar=2-((S)-2-methoxy-1-methyl-ethylamino)-4-(4-methyl-piperazin-1-yl)-phenyl], cpd. 167

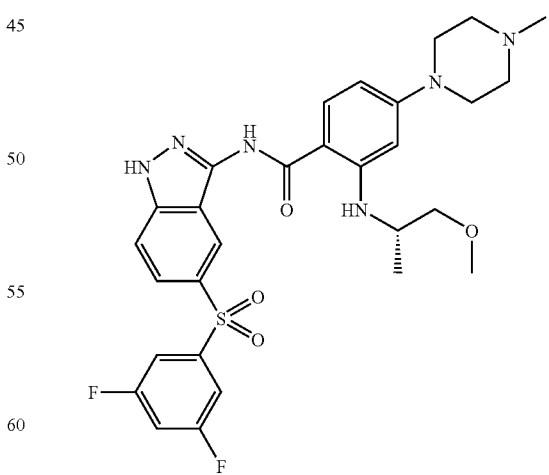

1H-NMR (400 MHz), δ (ppm, DMSO-d$_6$): 13.25 (bs, 1H), 10.42 (bs, 1H), 8.47 (m, 1H), 8.19 (d, J=7.8 Hz, 1H), 7.89 (dd, J1=8.9 Hz, J2=1.8 Hz, 1H), 7.80 (d, J=9.1 Hz, 1H), 7.72 (m, 2H), 7.66 (d, J=9.0 Hz, 1H), 7.62 (m, 1H), 6.26 (dd, J1=9.1

Hz, J2=2.3 Hz, 1H), 6.14 (d, J=2.3 Hz, 1H), 3.82 (m, 1H), 3.42-3.27 (m, 6H), 3.29 (s, 3H), 2.45 (m, 4H), 2.23 (s, 3H), 1.16 (d, J=6.4 Hz, 3H).

N-[5-(3,5-Difluoro-benzenesulfonyl)-1H-indazol-3-yl]-2-((R)-2-methoxy-1-methyl-ethylamino)-4-(4-methyl-piperazin-1-yl)-benzamide [(I), R1=R2=R3=H, R=3,5-difluorophenyl, Ar=2-((R)-2-methoxy-1-methyl-ethylamino)-4-(4-methyl-piperazin-1-yl)-phenyl], cpd. 175

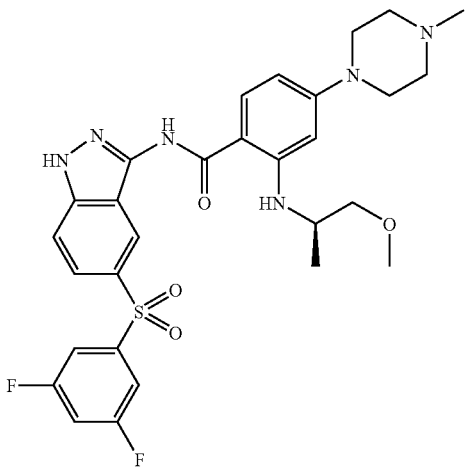

1H-NMR (400 MHz), δ (ppm, DMSO-d$_6$): 13.25 (bs, 1H), 10.42 (bs, 1H), 8.47 (m, 1H), 8.19 (d, J=7.8 Hz, 1H), 7.89 (dd, J1=8.9 Hz, J2=1.8 Hz, 1H), 7.80 (d, J=9.1 Hz, 1H), 7.72 (m, 2H), 7.66 (d, J=9.0 Hz, 1H), 7.62 (m, 1H), 6.26 (dd, J1=9.1 Hz, J2=2.3 Hz, 1H), 6.14 (d, J=2.3 Hz, 1H), 3.82 (m, 1H), 3.42-3.27 (m, 6H), 3.29 (s, 3H), 2.45 (m, 4H), 2.23 (s, 3H), 1.16 (d, J=6.4 Hz, 3H).

N-[5-(3,5-Difluoro-benzenesulfonyl)-1H-indazol-3-yl]-3-(tetrahydro-pyran-4-ylamino)-isonicotinamide [(I), R1=R2=R3=H, R=3,5-difluorophenyl, Ar=3-(tetrahydro-pyran-4-ylamino)-pyridin-4-yl], cpd. 202

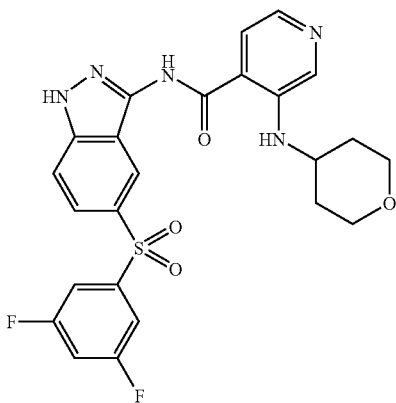

1H-NMR (400 MHz), δ (ppm, DMSO-d$_6$): 13.44 (bs, 1H), 11.17 (bs, 1H), 8.57 (m, 1H), 8.40 (s, 1H), 7.95 (d, J=5.0 Hz, 1H), 7.94 (m, 1H), 7.79 (d, J=5.0 Hz, 1H), 7.74 (m, 2H), 7.72 (m, 1H), 7.65 (m, 1H), 7.46 (bd, J=7.6 Hz, 1H), 3.90-3.81 (m, 3H), 3.51 (m, 2H), 2.00 (m, 2H), 1.43 (m, 2H).

N-[5-(3,5-Difluoro-benzenesulfonyl)-1H-indazol-3-yl]-3-(2-methoxy-1-methyl-ethylamino)-isonicotinamide [(I), R1=R2=R3=H, R=3,5-difluorophenyl, Ar=3-(2-methoxy-1-methyl-ethylamino)-pyridin-4-yl], cpd. 204

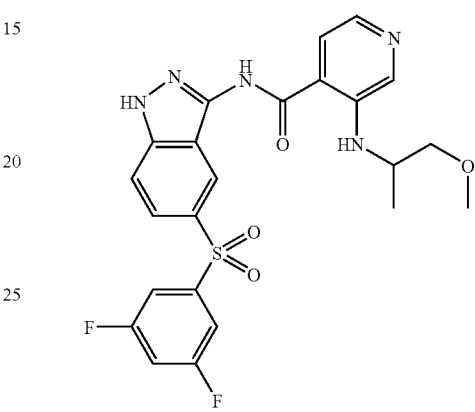

1H-NMR (400 MHz), δ (ppm, DMSO-d$_6$): 13.43 (bs, 1H), 11.13 (bs, 1H), 8.56 (m, 1H), 8.34 (s, 1H), 7.95-7.92 (m, 2H), 7.77-7.70 (m, 4H), 7.64 (m, 1H), 7.46 (bd, J=8.0 Hz, 1H), 3.99 (m, 1H), 3.45-3.39 (m, 2H), 3.29 (s, 3H), 1.20 (d, J=6.5 Hz, 3H).

Example 32

Preparation of 4-Amino-N-[5-(3,5-difluoro-benzenesulfonyl)-1-trityl-1H-indazol-3-yl]-2-[(tetrahydro-pyran-4-yl)-(2,2,2-trifluoro-acetyl)-amino]-benzamide [(XVII), R1=R2=R3=H, R=3,5-difluorophenyl, R11=1-triphenylmethyl, Ar=4-amino-2-[(tetrahydro-pyran-4-yl)-(2,2,2-trifluoro-acetyl)-amino]-phenyl]

To a solution of N-[5-(3,5-difluoro-benzenesulfonyl)-1-trityl-1H-indazol-3-yl]-4-nitro-2-[(tetrahydro-pyran-4-yl)-(2,2,2-trifluoro-acetyl)-amino]-benzamide (4.05 g, 4.5 mmol) in 1,4-dioxane (100 mL) was added cyclohexene (10 mL) and 10% Pd/C (405 mg). The mixture was stirred at 90° C. for 5 hours, filtered and evaporated to dryness. The residue was purified by flash chromatography on silica gel eluting with ethyl acetate/n-hexane 2:1 affording the title compound as white solid (2.9 g).

1H-NMR (400 MHz), δ (ppm, DMSO-d$_6$): 10.85 (bs, 1H), 8.29 (m, 1H), 7.72-7.63 (m, 5H), 7.36-7.17 (m, 15H), 6.66 (dd, J1=8.5 Hz, J2=2.3 Hz, 1H), 6.55-6.51 (m, 2H), 6.06 (bs, 2H), 4.50 (m, 1H), 3.89 (m, 1H), 3.77 (m, 1H), 3.44-3.37 (m, 2H), 1.87 (m, 1H), 1.62 (m, 1H), 1.55 (m, 1H), 1.30 (m, 1H).

Example 33

Preparation of N-[5-(3,5-difluoro-benzenesulfonyl)-1H-indazol-3-yl]-4-(2-dimethylamino-1-methyl-ethylamino)-2-(tetrahydro-pyran-4-ylamino)-benzamide [(I), R1=R2=R3=H, R=3,5-difluorophenyl, Ar=4-(2-dimethylamino-1-methyl-ethylamino)-2-(tetrahydro-pyran-4-ylamino)-phenyl], cpd. 127

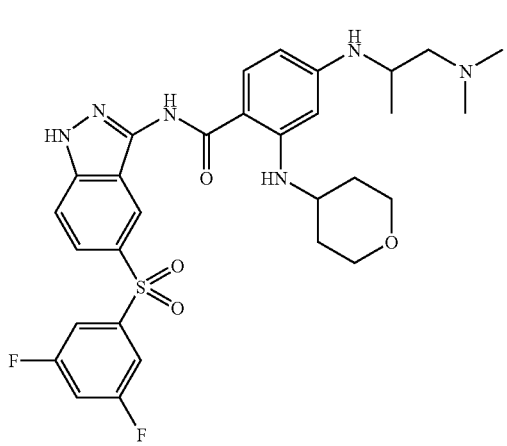

To a solution of 4-amino-N-[5-(3,5-difluoro-benzenesulfonyl)-1-trityl-1H-indazol-3-yl]-2-[(tetrahydro-pyran-4-yl)-(2,2,2-trifluoro-acetyl)-amino]-benzamide (1.56 g, 1.8 mmol) in dichloromethane (30 mL) was added trifluoroacetic acid (2.78 mL, 36 mmol), tetramethylammonium triacetoxyborohydride (710 mg, 2.7 mmol) and 1-dimethylamino-propan-2-one (316 microL, 2.7 mmol). The mixture was stirred at room temperature overnight then additional tetramethylammonium triacetoxyborohydride (710 mg, 2.7 mmol) and 1-dimethylamino-propan-2-one (316 microL, 2.7 mmol) were added. The mixture was heated at reflux and stirred for additional 6 hours. After evaporation of the volatiles, the residue was chromatographed on silica gel eluting with dichloromethane/methanol/triethylamine 90:10:0.1 affording 845 mg of N-[5-(3,5-difluoro-benzenesulfonyl)-1H-indazol-3-yl]-4-(2-dimethylamino-1-methyl-ethylamino)-2-[(tetrahydro-pyran-4-yl)-(2,2,2-trifluoro-acetyl)-amino]-benzamide that was dissolved in methanol (5 mL) and triethylamine (2 mL) and stirred at 50° C. for 6 hours. The mixture was then evaporated to dryness and the residue purified by flash chromatography on silica gel eluting with dichloromethane/methanol/30% NH$_4$OH 92:8:0.5 affording 416 mg of the title compound as pale yellow solid.

1H-NMR (400 MHz), δ (ppm, DMSO-d$_6$): 13.21 (bs, 1H), 10.26 (bs, 1H), 8.45 (d, J=1.1 Hz, 1H), 8.33 (d, J=7.4 Hz, 1H), 7.90 (dd, J1=8.9, J2=1.8 Hz, 1H), 7.74-7.69 (m, 3H), 7.66 (dd, J1=8.9 Hz, J2=0.6 Hz, 1H), 7.63 (m, 1H), 5.97-5.89 (m, 3H), 3.85 (m, 2H), 3.65-3.52 (m, 2H), 3.47 (m, 2H), 2.34 (m, 1H), 2.20 (s, 6H), 2.16 (m, 1H), 1.98 (m, 2H), 1.41 (m, 2H), 1.16 (d, J=6.2 Hz, 3H).

Operating in an analogous way, the following compounds were obtained:

4-(2-Diethylamino-1-methyl-ethylamino)-N-[5-(3,5-difluoro-benzenesulfonyl)-1H-indazol-3-yl]-2-(tetrahydro-pyran-4-ylamino)-benzamide [(I), R1=R2=R3=H, R=3,5-difluorophenyl, Ar=4-(2-diethylamino-1-methyl-ethylamino)-2-(tetrahydro-pyran-4-ylamino)-phenyl], cpd. 129

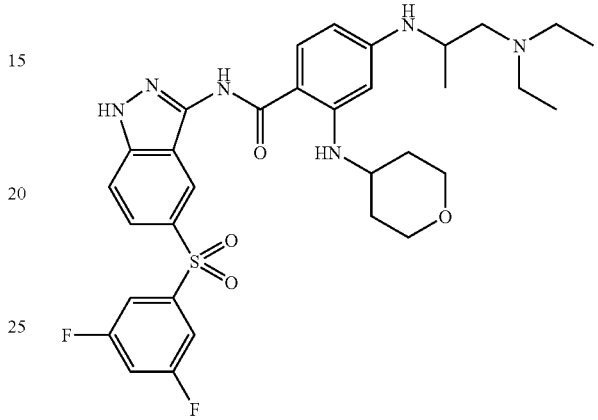

1H-NMR (400 MHz), δ (ppm, DMSO-d$_6$): 13.23 (bs, 1H), 10.26 (bs, 1H), 8.46 (d, J=1.1 Hz, 1H), 8.35 (d, J=7.3 Hz, 1H), 7.90 (dd, J1=8.9, J2=1.8 Hz, 1H), 7.74-7.69 (m, 3H), 7.67 (dd, J1=8.9 Hz, J2=0.6 Hz, 1H), 7.64 (m, 1H), 5.97-5.86 (m, 3H), 3.86 (m, 2H), 3.56 (m, 2H), 3.47 (m, 2H), 2.64-2.54 (m, 2H), 2.50-2.41 (m, 3H), 2.24 (dd, J1=12.8 Hz, J2=8.3 Hz, 1H), 1.99 (m, 2H), 1.40 (m, 2H), 1.17 (d, J=6.3 Hz, 3H), 0.99 (t, J=7.1 Hz, 6H).

N-[5-(3,5-Difluoro-benzenesulfonyl)-1H-indazol-3-yl]-4-(1-methyl-piperidin-4-ylamino)-2-(tetrahydro-pyran-4-ylamino)-benzamide [(I), R1=R2=R3=H, R=3,5-difluorophenyl, Ar=4-(1-methyl-piperidin-4-ylamino)-2-(tetrahydro-pyran-4-ylamino)-phenyl], cpd. 123

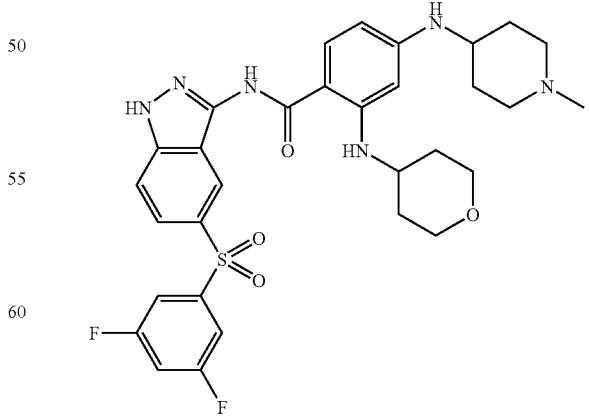

1H-NMR (400 MHz), δ (ppm, DMSO-d$_6$): 13.22 (bs, 1H), 10.28 (bs, 1H), 8.46 (d, J=1.1 Hz, 1H), 8.30 (d, J=7.1 Hz, 1H), 7.90 (dd, J1=8.9, J2=1.8 Hz, 1H), 7.75-7.70 (m, 3H), 7.67 (dd, J1=8.9 Hz, J2=0.6 Hz, 1H), 7.64 (m, 1H), 6.04 (bd, J=7.8 Hz, 1H), 5.95 (dd, J1=9.0 Hz, J2=2.0 Hz, 1H), 5.91 (d, J=2.0 Hz, 1H), 3.86 (m, 2H), 3.56 (m, 1H), 3.49 (m, 2H), 2.76 (m, 2H), 2.59 (m, 1H), 2.21 (s, 3H), 2.08 (m, 2H), 1.97 (m, 2H), 1.89 (m, 2H), 1.42 (m, 4H).

Example 34

Preparation of N-[5-(3,5-difluoro-benzenesulfonyl)-1H-indazol-3-yl]-4-(4-pyrrolidin-1-yl-piperidine-1-carbonyl)-benzamide [(I), R1=R2=R3=H, R=3,5-difluorophenyl, Ar=4-[(4-pyrrolidin-1-yl-piperidin-1-yl)carbonyl]-phenyl], cpd. 219

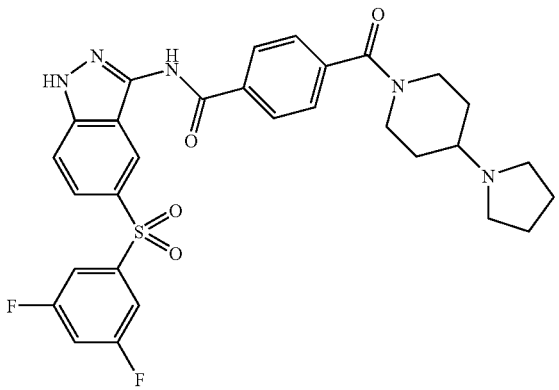

Step 1. N-[5-(3,5-Difluoro-benzenesulfonyl)-1-trityl-1H-indazol-3-yl]-terephthalamic acid [(XVII), R1=R2=R3=H, R=3,5-difluorophenyl, R11=1-triphenylmethyl, Ar=4-carboxy-phenyl]

A mixture of N-[5-(3,5-difluoro-benzenesulfonyl)-1-trityl-1H-indazol-3-yl]-terephthalamic acid methyl ester (400 mg, 0.56 mmol), tetrahydrofuran (8 mL), water (4 mL) and lithium hydroxide hydrate (35 mg, 1.5 eq) was stirred at room temperature overnight. The solvents were evaporated to dryness. The residue was taken up with ethyl acetate, washed with 5% aqueous solution of potassium bisulfate, brine, dried over sodium sulfate and evaporated to dryness affording the crude title compound that was used as such for the next step without further purification.

Step 2. N-[5-(3,5-Difluoro-benzenesulfonyl)-1-trityl-1H-indazol-3-yl]-4-(4-pyrrolidin-1-yl-piperidine-1-carbonyl)-benzamide [(XVII), R1=R2=R3=H, R=3,5-difluorophenyl, R11=1-triphenylmethyl, Ar=4-[(4-pyrrolidin-1-yl-piperidin-1-yl)carbonyl]-phenyl]

The crude N-[5-(3,5-difluoro-benzenesulfonyl)-1-trityl-1H-indazol-3-yl]-terephthalamic acid (0.56 mmol) was treated with dichloromethane (8 mL), 1-ethyl-3-(3-dimethylaminopropyl)carbodiimide hydrochloride (140 mg, 1.3 eq), 1-hydroxybenzotriazole (98 mg, 1.3 eq) and 4-pyrrolidin-1-yl-piperidine (113 mg, 1.3 eq). The reaction mixture was stirred at room temperature overnight, diluted with dichloromethane, washed with brine and with a saturated solution of sodium hydrogenocarbonate, dried over sodium sulfate and evaporated to dryness affording the crude title compound that was used as such for the next step without further purification.

Step 3. N-[5-(3,5-difluoro-benzenesulfonyl)-1H-indazol-3-yl]-4-(4-pyrrolidin-1-yl-piperidine-1-carbonyl)-benzamide [(I), R1=R2=R3=H, R=3,5-difluorophenyl, Ar=4-[(4-pyrrolidin-1-yl-piperidin-1-yl)carbonyl]-phenyl], cpd. 219

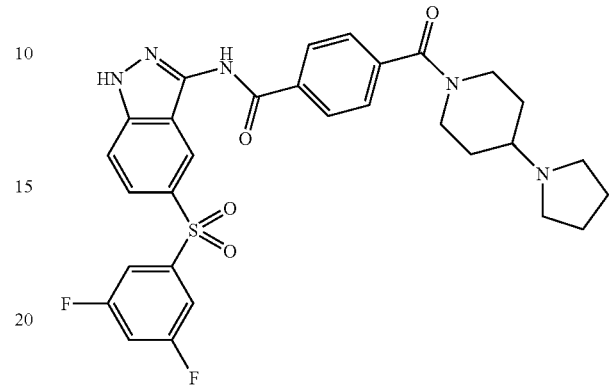

The crude N-[5-(3,5-difluoro-benzenesulfonyl)-1-trityl-1H-indazol-3-yl]-4-(4-pyrrolidin-1-yl-piperidine-1-carbonyl)-benzamide was treated with 15 mL of 1,4-dioxane and with 4M hydrochloric acid in 1,4-dioxane (4 mL). The mixture was stirred at room temperature for 2 days then treated with methanol (15 mL) and stirred for additional 3 hours. The solvents were removed under reduced pressure and the residue taken up with ethyl acetate, washed with 10% aqueous ammonium hydroxide, dried over sodium sulfate and evaporated to dryness. The crude was purified by flash chromatography over silica gel eluting with dichloromethane/methanol/7N $NH_3$ in methanol 100:7:1 affording 185 mg of the title compound.

1H-NMR (400 MHz), δ (ppm, DMSO-$d_6$): 13.39 (bs, 1H), 11.19 (bs, 1H), 8.65 (m, 1H), 8.14 (m, 2H), 7.92 (dd, J1=8.9 Hz, J2=1.7 Hz, 1H), 7.73 (m, 2H), 7.70 (d, J=8.9 Hz, 1H), 7.63 (m, 1H), 7.55 (m, 2H), 4.28 (m, 1H), 3.51 (m, 1H), 3.07 (m, 2H), 2.50 (m, 4H), 2.28 (m, 1H), 1.92 (m, 1H), 1.79 (m, 1H), 1.68 (m, 4H), 1.41 (m, 2H).

Operating in an analogous way, the following compounds were obtained:

N-[5-(3,5-Difluoro-benzenesulfonyl)-1H-indazol-3-yl]-4-((R)-2-pyrrolidin-1-ylmethyl-pyrrolidine-1-carbonyl)-benzamide [(I), R1=R2=R3=H, R=3,5-difluorophenyl, Ar=4-((R)-2-pyrrolidin-1-ylmethyl-pyrrolidine-1-carbonyl)-phenyl], cpd. 220

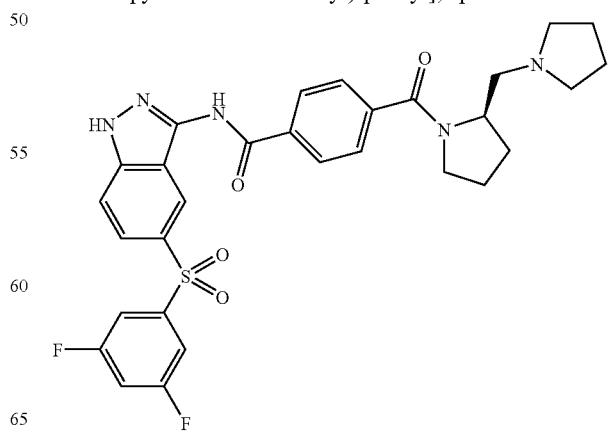

1H-NMR (400 MHz), δ (ppm, DMSO-d$_6$): 13.41 (bs, 1H), 11.21 (bs, 1H), 8.67 (m, 1H), 8.15 (m, 2H), 7.93 (dd, J1=8.9 Hz, J2=1.7 Hz, 1H), 7.74 (m, 2H), 7.70 (d, J=8.9 Hz, 1H), 7.68-7.61 (m, 3H), 4.29 (m, 1H), 3.49 (m, 2H), 2.7-2.5 (m, 6H), 2.1-1.4 (m, 8H).

N-[5-(3,5-Difluoro-benzenesulfonyl)-1H-indazol-3-yl]-4-((S)-2-pyrrolidin-1-ylmethyl-pyrrolidine-1-carbonyl)-benzamide [(I), R1=R2=R3=H, R=3,5-difluorophenyl, Ar=4-((S)-2-pyrrolidin-1-ylmethyl-pyrrolidine-1-carbonyl)-phenyl], cpd. 221

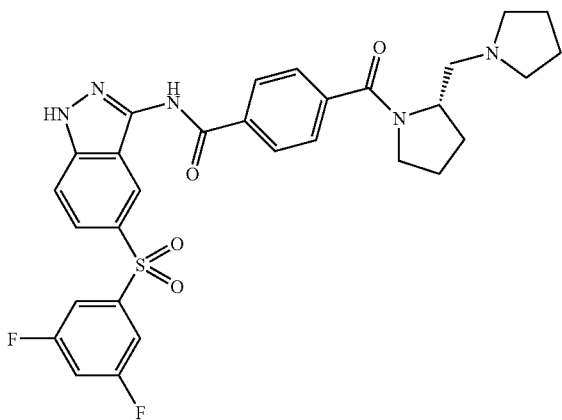

1H-NMR (400 MHz), δ (ppm, DMSO-d$_6$): 13.41 (bs, 1H), 11.21 (bs, 1H), 8.67 (m, 1H), 8.15 (m, 2H), 7.93 (dd, J1=8.9 Hz, J2=1.7 Hz, 1H), 7.74 (m, 2H), 7.70 (d, J=8.9 Hz, 1H), 7.68-7.61 (m, 3H), 4.29 (m, 1H), 3.49 (m, 2H), 2.7-2.5 (m, 6H), 2.1-1.4 (m, 8H).

Example 35

Preparation of 1-piperidin-4-yl-1H-pyrazole-4-carboxylic acid [5-(3,5-difluoro-benzenesulfonyl)-1H-indazol-3-yl]-amide [(I), R1=R2=R3=H, R=3,5-difluorophenyl, Ar=1-piperidin-4-yl-1H-pyrazol-4-yl], cpd. 222

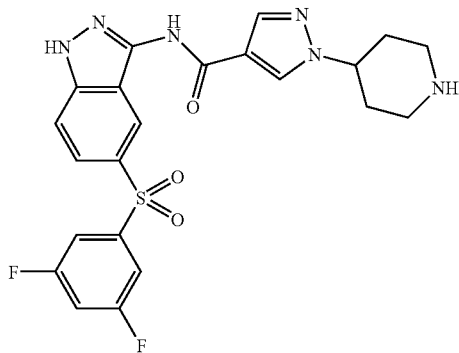

Step 1. 4-(4-Carboxy-pyrazol-1-yl)-piperidine-1-carboxylic acid tert-butyl ester To a solution of 1H-pyrazole-4-carboxylic acid ethyl ester (701 mg, 5 mmol) in dry N,N-dimethylformamide (15 mL) at 0-5° C., under argon, was added 60% sodium hydride (480 mg, 1.2 eq). After stirring for 1 hour was added a solution of 4-methanesulfonyloxy-piperidine-1-carboxylic acid tert-butyl ester (1.53 g, 1.1 eq) in dry N,N-dimethylformamide (4 mL). The mixture was heated to 100° C., stirred for 6 hours then treated with water and extracted with ethyl acetate. The organic layer was separated (organic layer A). The aqueous layer was acidified with a 5% aqueous solution of potassium bisulfate and extracted with ethyl acetate giving, after separation, the organic layer B. The organic layer A was evaporated to dryness. The residue was treated with 20 mL of methanol, 5 mL of water and 1.12 g of sodium hydroxide (20 mmol) and stirred at room temperature for 2 days. The solvents were removed under reduced pressure, the residue treated with ethyl acetate and washed with 5% aqueous solution of potassium bisulfate giving the organic layer C. The combined organic layers B and C were dried over sodium sulfate and evaporated to dryness. The residue was triturated with diethyl ether and dried under vacuum affording 590 mg of title compound.

Step 2. 4-{4-[5-(3,5-Difluoro-benzenesulfonyl)-1-trityl-1H-indazol-3-ylcarbamoyl]-pyrazol-1-yl}-piperidine-1-carboxylic acid tert-butyl ester [(XVII), R1=R2=R3=H, R=3,5-difluorophenyl, R11=1-triphenylmethyl, Ar=1-(1-tert-butoxycarbonyl-piperidin-4-yl)-1H-pyrazol-4-yl]

To a stirred solution of 4-(4-carboxy-pyrazol-1-yl)-piperidine-1-carboxylic acid tert-butyl ester (200 mg, 0.677 mmol) in dry dichloromethane (6 mL), at 0° C., under argon, were added two drops of N,N-dimethylformamide and 62 microL of oxalyl chloride (1.05 eq). After 15 minutes the volatiles were removed under reduced pressure at room temperature. The crude acyl chloride thus obtained was dissolved under argon into dry tetrahydrofuran (5 mL), cooled to 0° C. and treated with a solution of 5-(3,5-difluoro-benzenesulfonyl)-1-trityl-1H-indazol-3-ylamine (300 mg, 0.85 eq) and triethylamine (0.28 mL, 3 eq) in dry tetrahydrofuran (7 mL). The mixture was allowed to warm to room temperature overnight then evaporated to dryness. The residue was dissolved into dichloromethane, washed with water and with a saturated solution of sodium hydrogenocarbonate, dried over sodium sulphate and evaporated to dryness to give the crude title compound that was used as such for the next step without further purification.

Step 3. 1-Piperidin-4-yl-1H-pyrazole-4-carboxylic acid [5-(3,5-difluoro-benzenesulfonyl)-1H-indazol-3-yl]-amide [(I), R1=R2=R3=H, R=3,5-difluorophenyl, Ar=1-piperidin-4-yl-1H-pyrazol-4-yl], cpd. 222

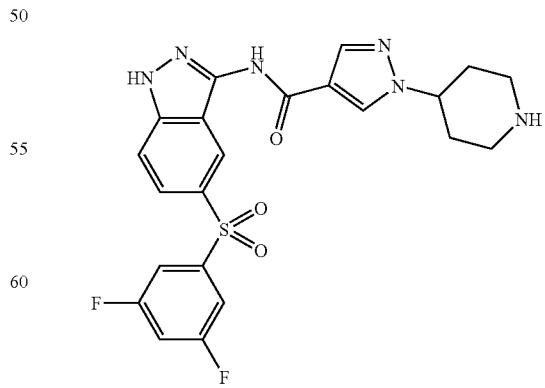

The crude 4-{4-[5-(3,5-difluoro-benzenesulfonyl)-1-trityl-1H-indazol-3-ylcarbamoyl]-pyrazol-1-yl}-piperidine-1- carboxylic acid tert-butyl ester was dissolved into 15 mL of 1,4-dioxane and added with 3 mL of 4M hydrochloric acid in 1,4-dioxane and stirred at room temperature overnight. Methanol was then added and the mixture stirred for additional 2 hours. The volatiles were removed under reduced pressure, the residue re-dissolved into ethyl acetate, washed with 10% ammonium hydroxide in water, dried over sodium sulfate and evaporated to dryness. The residue was stirred overnight with diethyl ether/methanol 95:5, filtered, washed with diethyl ether/methanol 9:1 then with diethyl ether and dried in oven at 60° C. affording 170 mg of the title compound.

1H-NMR (400 MHz), δ (ppm, DMSO-$d_6$): 13.33 (bs, 1H), 10.80 (bs, 1H), 8.70 (d, J=1.22 Hz, 1H), 8.53 (s, 1H), 8.17 (s, 1H), 7.90 (dd, J1=8.96 Hz, J2=1.9 Hz, 1H), 7.76-7.69 (m, 2H), 7.67 (d, J=9.5 Hz, 1H), 7.64-7.59 (m, 1H), 4.33-4.23 (m, 1H), 3.11-3.02 (m, 2H), 2.66-2.58 (m, 2H), 2.05-1.97 (m, 2H), 1.87-1.74 (m, 2H).

The invention claimed is:

1. A compound of formula (I):

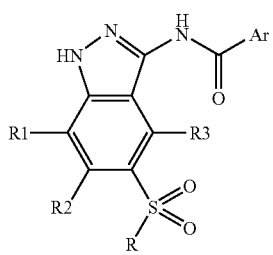

(I)

wherein:

Ar is aryl optionally substituted with one or more substituents independently selected from halogen, alkenyl, alkynyl, cyano, nitro, NHCOR4, COR4, NR5R6, NR5COR4, OR7, SR7, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl and aryl, wherein:

R4 is hydrogen, alkenyl, alkynyl, NR5R6, OR7, SR7, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl or aryl;

R5 and R6 are independently hydrogen, alkenyl, alkynyl, R8R9N—C$_2$-C$_6$ alkyl, R8O-C$_2$-C$_6$ alkyl, an optionally further substituted straight or branched C$_1$-C$_6$ alkyl, C$_3$-C$_6$ cycloalkyl, heterocycly or or aryl, or R5 and R6, taken together with the nitrogen atom to which they are bonded, may form an optionally substituted heterocyclyl group;

R7 is hydrogen, alkenyl, alkynyl, COR4, SOR10, SO$_2$R10, R8R9N—C$_2$-C$_6$ alkyl, R8O-C$_2$-C$_6$ alkyl, an optionally further substituted straight or branched C$_1$-C$_6$ alkyl, C$_3$-C$_6$ cycloalkyl, heterocyclyl or aryl, wherein R4 is as defined above;

R8 and R9 are independently hydrogen, alkenyl, alkynyl, COR4, an optionally further substituted straight or branched C$_1$-C$_6$ alkyl, C$_3$-C$_6$ cycloalkyl, heterocyclyl or aryl, or R8 and R9, taken together with the nitrogen atom to which they are bonded, may form an optionally substituted heterocyclyl group, wherein R4 is as defined above;

R10 is hydrogen, alkenyl, alkynyl, NR5R6, OR7, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl or aryl, wherein R5, R6, R7, R8 and R9 are as defined above;

R is an optionally further substituted straight or branched C$_1$-C$_6$ alkyl, C$_3$-C$_6$ cycloalkyl, heterocyclyl or aryl;

R1, R2 and R3 are independently hydrogen, halogen, nitro, an optionally further substituted straight or branched C$_1$-C$_6$ alkyl, NR5R6 or OR7, wherein R5, R6 and R7 are as defined above;

and pharmaceutically acceptable salt thereof.

2. A compound of formula (I) as defined in claim 1 wherein Ar is a group of formula:

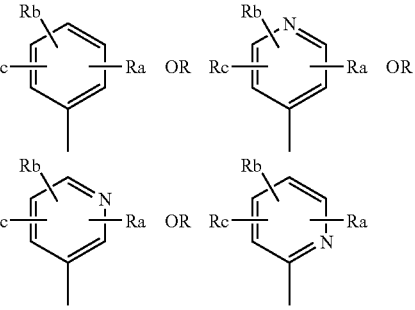

wherein Ra, Rb and Re are independently hydrogen, halogen, alkenyl, alkynyl, cyano, nitro, NHCOR4, COR4, NR5R6, NR5COR4, OR7, SR7, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl or aryl, wherein R is an optionally further substituted aryl.

3. A compound of formula (I) as defined in claim 1 or 2 wherein Ar is a group of formula:

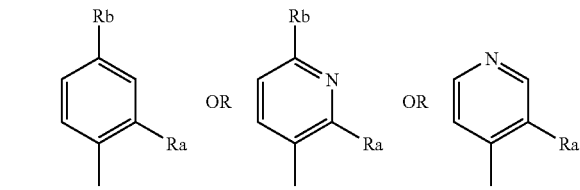

wherein Ra is hydrogen, halogen, nitro, NHCOR4 or NR5R6 and Rb is hydrogen, nitro, NR5R6, OR7 or R8R9N—C$_1$-C$_6$ alkyl wherein R4, R5, R6, R7, R8 and R9 are as defined above and R is an optionally further substituted phenyl.

4. A compound or a pharmaceutically acceptable salt thereof which is selected from the group consisting of:
- N-(5-Benzenesulfonyl-1H-indazol-3-yl)-4-(4-methyl-piperazin-1-yl)-benzamide;
- N-[5-(3,5-Difluoro-benzenesulfonyl)-1H-indazol-3-yl]-4-(4-methyl-piperazin-1-yl)-benzamide;
- 2-Amino-N-[5-(3,5-difluoro-benzenesulfonyl)-1H-indazol-3-yl]-4-(4-methyl-piperazin-1-yl)-benzamide;
- N-(5-Benzenesulfonyl-1H-indazol-3-yl)-4-(4-methyl-piperazin-1-yl)-2-(tetrahydro-pyran-4-ylamino)-benzamide;
- N-[5-(3-Fluoro-benzenesulfonyl)-1H-indazol-3-yl]-4-(4-methyl-piperazin-1-yl)-2-(tetrahydro-pyran-4-ylamino)-benzamide;
- N-[5-(3,5-Difluoro-benzenesulfonyl)-1H-indazol-3-yl]-4-(4-methyl-piperazin-1-yl)-2-(tetrahydro-pyran-4-ylamino)-benzamide;
- 1H-Pyrrole-2-carboxylic acid [2-(5-benzenesulfonyl-1H-indazol-3-ylcarbamoyl)-5-(4-methyl-piperazin-1-yl)-phenyl]-amide;
- 1H-Pyrrole-2-carboxylic acid [2-[5-(3-fluoro-benzenesulfonyl)-1H-indazol-3-ylcarbamoyl]-5-(4-methyl-piperazin-1-yl)-phenyl]-amide;
- 1H-Pyrrole-2-carboxylic acid [2-[5-(3,5-difluoro-benzenesulfonyl)-1H-indazol-3-ylcarbamoyl]-5-(4-methyl-piperazin-1-yl)-phenyl]-amide;
- (S)-Tetrahydro-furan-2-carboxylic acid [2-(5-benzenesulfonyl-1H-indazol-3-ylcarbamoyl)-5-(4-methyl-piperazin-1-yl)-phenyl]-amide;
- 1H-Pyrrole-3-carboxylic acid [2-(5-benzenesulfonyl-1H-indazol-3-ylcarbamoyl)-5-(4-methyl-piperazin-1-yl)-phenyl]-amide;
- 1H-Pyrrole-3-carboxylic acid [2-[5-(3-fluoro-benzenesulfonyl)-1H-indazol-3-ylcarbamoyl]-5-(4-methyl-piperazin-1-yl)-phenyl]-amide;
- 1H-Pyrrole-3-carboxylic acid [2-[5-(3,5-difluoro-benzenesulfonyl)-1H-indazol-3-ylcarbamoyl]-5-(4-methyl-piperazin-1-yl)-phenyl]-amide;
- 1-Methyl-1H-pyrrole-2-carboxylic acid [2-(5-benzenesulfonyl-1H-indazol-3-ylcarbamoyl)-5-(4-methyl-piperazin-1-yl)-phenyl]-amide;
- 1-Methyl-1H-pyrrole-2-carboxylic acid [2-[5-(3-fluoro-benzenesulfonyl)-1H-indazol-3-ylcarbamoyl]-5-(4-methyl-piperazin-1-yl)-phenyl]-amide;
- 1-Methyl-1H-pyrrole-2-carboxylic acid [2-[5-(3,5-difluoro-benzenesulfonyl)-1H-indazol-3-ylcarbamoyl]-5-(4-methyl-piperazin-1-yl)-phenyl]-amide;
- N-[5-(3-Fluoro-5-methoxy-benzenesulfonyl)-1H-indazol-3-yl]-4-(4-methyl-piperazin-1-yl)-2-(tetrahydro-pyran-4-ylamino)-benzamide;
- N-[5-(3,5-Difluoro-benzenesulfonyl)-1H-indazol-3-yl]-4-(4-ethyl-[1,4]diazepan-1-yl)-2-(tetrahydro-pyran-4-ylamino)-benzamide;
- N-[5-(3,5-Difluoro-benzenesulfonyl)-1H-indazol-3-yl]-4-(2-dimethylamino-ethoxy)-2-(tetrahydro-pyran-4-ylamino)-benzamide;
- N-[5-(3,5-Difluoro-benzenesulfonyl)-1H-indazol-3-yl]-4-(2-pyrrolidin-1-yl-ethoxy)-2-(tetrahydro-pyran-4-ylamino)-benzamide;
- N-[5-(3,5-Difluoro-benzenesulfonyl)-1H-indazol-3-yl]-4-(4-methyl-piperidin-4-yloxy)-2-(tetrahydro-pyran-4-ylamino)-benzamide;
- N-[5-(3,5-Difluoro-benzenesulfonyl)-1H-indazol-3-yl]-4-dimethylaminomethyl-2-(tetrahydro-pyran-4-ylamino)-benzamide;
- N-[5-(3,5-Difluoro-benzenesulfonyl)-1H-indazol-3-yl]-4-pyrrolidin-1-ylmethyl-2-(tetrahydro-pyran-4-ylamino)-benzamide;
- N-[5-(3,5-Difluoro-benzenesulfonyl)-1H-indazol-3-yl]-4-piperidin-1-ylmethyl-2-(tetrahydro-pyran-4-ylamino)-benzamide;
- N-[5-(3,5-Difluoro-benzenesulfonyl)-1H-indazol-3-yl]-4-(1-methyl-piperidin-4-ylamino)-2-(tetrahydro-pyran-4-ylamino)-benzamide;
- N-[5-(3,5-Difluoro-benzenesulfonyl)-1H-indazol-3-yl]-4-(2-dimethylamino-1-methyl-ethylamino)-2-(tetrahydro-pyran-4-ylamino)-benzamide;
- 4-(2-Diethylamino-1-methyl-ethylamino)-N-[5-(3,5-difluoro-benzenesulfonyl)-1H-indazol-3-yl]-2-(tetrahydro-pyran-4-ylamino)-benzamide;
- 4-[2-Dimethylamino-ethyl)-methyl-amino]-N-[5-(3-fluoro-benzenesulfonyl)-1H-indazol-3-yl]-2-(tetrahydro-pyran-4-ylamino)-benzamide;
- N-[5-(3,5-Difluoro-benzenesulfonyl)-1H-indazol-3-yl]-4-[(2-dimethylamino-ethyl)-methyl-amino]-2-(tetrahydro-pyran-4-ylamino)-benzamide;
- N-[5-(3,5-Difluoro-benzenesulfonyl)-1H-indazol-3-yl]-4-{[2-(isopropyl-methyl-amino)-ethyl]-methyl-amino}-2-(tetrahydro-pyran-4-ylamino)-benzamide;
- N-[5-(3,5-Difluoro-benzenesulfonyl)-1H-indazol-3-yl]-4-[methyl-(2-piperidin-1-yl-ethyl)-amino]-2-(tetrahydro-pyran-4-ylamino)-benzamide;
- N-[5-(3,5-Difluoro-benzenesulfonyl)-1H-indazol-3-yl]-4-[methyl-(2-morpholin-4-yl-ethyl)-amino]-2-(tetrahydro-pyran-4-ylamino)-benzamide;
- N-[5-(3,5-Difluoro-benzenesulfonyl)-1H-indazol-3-yl]-4-[(2-dimethylamino-ethyl)-ethyl-amino]-2-(tetrahydro-pyran-4-ylamino)-benzamide;
- 4-[(3-Dimethylamino-propyl)-methyl-amino]-N-[5-(3-fluoro-benzenesulfonyl)-1H-indazol-3-yl]-2-(tetrahydro-pyran-4-ylamino)-benzamide;
- N-[5-(3,5-Difluoro-benzenesulfonyl)-1H-indazol-3-yl]-4-[(3-methylamino-propyl)-methyl-amino]-2-(tetrahydro-pyran-4-ylamino)-benzamide;
- N-[5-(3,5-Difluoro-benzenesulfonyl)-1H-indazol-3-yl]-4-(4-dimethylamino-piperidin-1-yl)-2-(tetrahydro-pyran-4-ylamino)-benzamide;
- N-[5-(3,5-Difluoro-benzenesulfonyl)-1H-indazol-3-yl]-4-(4-pyrrolidin-1-yl-piperidin-1-yl)-2-(tetrahydro-pyran-4-ylamino)-benzamide;
- N-[5-(3,5-Difluoro-benzenesulfonyl)-1H-indazol-3-yl]-4-[methyl-(1-methyl-pyrrolidin-3-yl)-amino]-2-(tetrahydro-pyran-4-ylamino)-benzamide;
- N-[5-(3,5-Difluoro-benzenesulfonyl)-1H-indazol-3-yl]-2-(2-methoxy-ethylamino)-4-(4-methyl-piperazin-1-yl)-benzamide;
- N-[5-(3-Fluoro-benzenesulfonyl)-1H-indazol-3-yl]-2-(2-methoxy-ethylamino)-4-(4-methyl-piperazin-1-yl)-benzamide;

N-[5-(3,5-Difluoro-benzenesulfonyl)-1H-indazol-3-yl]-4-[(2-dimethylamino-ethyl)-methyl-amino]-2-(2-methoxy-ethylamino)-benzamide;

N-[5-(3,5-Difluoro-benzenesulfonyl)-1H-indazol-3-yl]-4-[(3-dimethylamino-propyl)-methyl-amino]-2-(2-methoxy-ethylamino)-benzamide;

N-[5-(3,5-Difluoro-benzenesulfonyl)-1H-indazol-3-yl]-2-(2-methoxy-1-methyl-ethylamino)-4-(4-methyl-piperazin-1-yl)-benzamide;

N-[5-(3-Fluoro-benzenesulfonyl)-1H-indazol-3-yl]-2-(2-methoxy-1-methyl-ethylamino)-4-(4-methyl-piperazin-1-yl)-benzamide;

N-[5-(3,5-Difluoro-benzenesulfonyl)-1H-indazol-3-yl]-4-[(2-dimethylamino-ethyl)-methyl-amino]-2-(2-methoxy-1-methyl-ethylamino)-benzamide;

N-[5-(3,5-Difluoro-benzenesulfonyl)-1H-indazol-3-yl]-4-[(3-dimethylamino-propyl)-methyl-amino]-2-(2-methoxy-1-methyl-ethylamino)-benzamide;

N-[5-(3,5-Difluoro-benzenesulfonyl)-1H-indazol-3-yl]-4-dimethylaminomethyl-2-(2-methoxy-1-methyl-ethylamino)-benzamide;

N-[5-(3,5-Difluoro-benzenesulfonyl)-1H-indazol-3-yl]-2-((S)-2-methoxy-1-methyl-ethylamino)-4-(4-methyl-piperazin-1-yl)-benzamide;

N-[5-(3-Fluoro-benzenesulfonyl)-1H-indazol-3-yl]-2-((S)-2-methoxy-1-methyl-ethylamino)-4-(4-methyl-piperazin-1-yl)-benzamide;

N-[5-(3,5-Difluoro-benzenesulfonyl)-1H-indazol-3-yl]-2-((R)-2-methoxy-1-methyl-ethylamino)-4-(4-methyl-piperazin-1-yl)-benzamide;

N-[5-(3-Fluoro-benzenesulfonyl)-1H-indazol-3-yl]-2-((R)-2-methoxy-1-methyl-ethylamino)-4-(4-methyl-piperazin-1-yl)-benzamide;

N-[5-(3,5-Difluoro-benzenesulfonyl)-1H-indazol-3-yl]-2-(2-methoxy-1-methoxymethyl-ethylamino)-4-(4-methyl-piperazin-1-yl)-benzamide;

N-[5-(3-Fluoro-benzenesulfonyl)-1H-indazol-3-yl]-2-(2-methoxy-1-methoxymethyl-ethylamino)-4-(4-methyl-piperazin-1-yl)-benzamide;

N-[5-(3,5-Difluoro-benzenesulfonyl)-1H-indazol-3-yl]-4-[(2-dimethylamino-ethyl)-methyl-amino]-2-(2-methoxy-1-methoxymethyl-ethylamino)-benzamide;

N-[5-(3,5-Difluoro-benzenesulfonyl)-1H-indazol-3-yl]-4-[(3-dimethylamino-propyl)-methyl-amino]-2-(2-methoxy-1-methoxymethyl-ethylamino)-benzamide;

N-[5-(3,5-Difluoro-benzenesulfonyl)-1H-indazol-3-yl]-2-(2-methoxy-1,1-dimethyl-ethylamino)-4-(4-methyl-piperazin-1-yl)-benzamide;

N-[5-(3,5-Difluoro-benzenesulfonyl)-1H-indazol-3-yl]-2-((R)-1-methoxymethyl-propylamino)-4-(4-methyl-piperazin-1-yl)-benzamide;

N-[5-(3,5-Difluoro-benzenesulfonyl)-1H-indazol-3-yl]-3-(tetrahydro-pyran-4-ylamino)-isonicotinamide;

N-[5-(3,5-Difluoro-benzenesulfonyl)-1H-indazol-3-yl]-3-(2-methoxy-1-methyl-ethylamino)-isonicotinamide;

N-[5-(3,5-Difluoro-benzenesulfonyl)-1H-indazol-3-yl]-6-(4-methyl-piperazin-1-yl)-2-(tetrahydro-pyran-4-ylamino)-nicotinamide;

N-[5-(3,5-Difluoro-benzenesulfonyl)-1H-indazol-3-yl]-4-[(3-dimethylamino-propyl)-methyl-amino]-2-isobutylamino-benzamide.

5. A process for preparing a compound of formula (I) as defined in claim 1, characterized in that the process comprises:

g) hydrolysing a compound of formula (X):

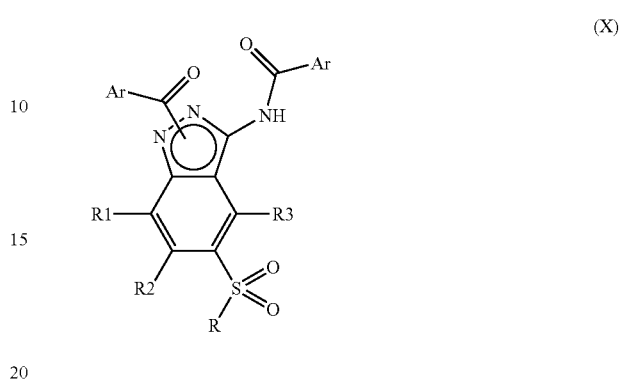

6. A process for preparing a compound of formula (I) as defined in claim 1, characterized in that the process comprises: m) deprotecting the compound of formula (XVII):

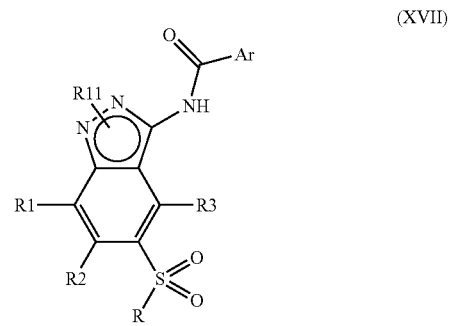

wherein R1, R2, R3, R, and Ar are as defined in claim 1, and R11 is benzyl, 4-methoxybenzyl, 2,4-dimethoxybenzyl, or triphenylmethyl.

7. A process for preparing a compound of formula (I) according to claim 5 characterized in that the optional conversion of a compound of formula (I) into another compound of formula (I), is carried out by one or more of the following reactions:

6) reducing a compound of formula (I) wherein Ar is a substituted aryl and one of the substituents is $NO_2$, for obtaining a compound of formula (I) wherein such substituent is $NH_2$;

7) acylating a compound of formula (I), wherein Ar is a substituted aryl and one of the substituents is $NH_2$, by reaction with an excess of a compound of formula (XXIII)

wherein R4 hydrogen, alkenyl, alkynyl, NR5R6, OR7, SR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl and W is hydroxy, halogen or a suitable leaving group, followed by selective deprotection of the acyl group on the pyrazole ring, for obtaining a compound of formula (I) wherein such substituent is a NHCOR4 residue, wherein R4 is hydrogen, alkenyl, alkynyl, NR5R6, OR7, SR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl;
  8) reacting a compound of formula (I), wherein Ar is a substituted aryl and one of the substituents is $NH_2$, with a suitable aldehyde or ketone in the presence of a reducing agent, for obtaining a compound of formula (I), wherein such substituent is a NR5R6 group, wherein one of the R5 or R6 are independently hydrogen, alkenyl, alkynyl, COR4, an optionally further substituted straight or branched $C_1$-$C_6$ alkyl, $C_3$-$C_6$ cycloalkyl, heterocyclyl or aryl, or R8 and R9, taken together with the nitrogen atom to which they are bonded, may form an optionally substituted heterocyclyl group.

8. A method for treating ovary, breast, cervix, colorectal, renal, pancreatic, bladder, epidermoid, prostate, thyroid and lung cancer, cholangiocarcinoma, Ewing's sarcoma, glioblastoma, gliosarcoma, leukemia, lymphoma, melanoma, multiple myeloma, neuroblastoma, osteosarcoma and combinations thereof which comprises administering to a mammal in need thereof an effective amount of a compound of formula (I) as defined in claim 1.

9. The method according to claim 8 which provides tumor angiogenesis and metastasis inhibition.

10. The method according to claim 8 further comprising subjecting the mammal in need thereof to a radiation therapy or chemotherapy regimen in combination with at least one cytostatic or cytotoxic agent.

11. The method according to claim 8 wherein the mammal in need thereof is a human.

12. A method for inhibiting IGF1-R activity which comprises administering to a mammal in need thereof an effective amount of a compound as defined in claim 1.

13. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

14. A product or kit comprising a compound of formula (I) or a pharmaceutically acceptable salt thereof, as defined in claim 1, and one or more chemotherapeutic agents, as a combined preparation for simultaneous, separate or sequential use in the treatment of ovary, breast, cervix, colorectal, renal, pancreatic, bladder, epidermoid, prostate, thyroid and lung cancer, cholangiocarcinoma, Ewing's sarcoma, glioblastoma, gliosarcoma, leukemia, lymphoma, melanoma, multiple myeloma, neuroblastoma, osteosarcoma and combinations thereof.

15. A process for preparing a compound of formula (I) as defined in claim 5, characterized in that the process comprises separating the resulting compound into the single isomers; converting the resulting compound of formula (I) into a different compound of formula (I) and/or into a pharmaceutically acceptable salt.

16. A process for preparing a compound of formula (I) according to claim 6, characterized in that the conversion of a compound of formula (XVII) into another compound of formula (XVII), is carried out by one or more of the following reactions:
  1) reducing a compound of formula (XVII) wherein Ar is a substituted aryl and one of the substituents is $NO_2$, for obtaining a compound of formula (XVII) wherein such substituent is $NH_2$;
  2) acylating a compound of formula (XVII), wherein Ar is a substituted aryl and one of the substituents is $NH_2$, by reaction with an acylating agent of formula (XXIII)

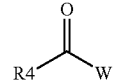

(XXIII)

wherein R4 is hydrogen, alkenyl, alkynyl, NR5R6, OR7, SR7, R8R9N—$C_1$-$C_6$ alkyl, alkyl, an optionally further substituted straight or branched $C_1$-$C_6$ alkyl, $C_3$-$C_6$ cycloalkyl, heterocyclyl or aryl and W is hydroxy, halogen or a suitable leaving group, for obtaining a compound of formula (XVII) wherein such substituent is a NHCOR4 residue, wherein R4 is hydrogen, alkenyl, alkynyl, NR5R6, OR7, SR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl or aryl;
  3) reacting a compound of formula (XVII), wherein Ar is a substituted aryl and one of the substituents is $NH_2$, with a suitable aldehyde or ketone in the presence of a reducing agent, for obtaining a compound of formula (XVII), wherein such substituent is a NR5R6 group, wherein one of the R5 or R6 is hydrogen and the other is an optionally further substituted straight or branched $C_1$-$C_6$ alkyl, $C_3$-$C_6$ cycloalkyl, heterocyclyl, R8R9N—$C_2$-$C_6$ alkyl, R8O-$C_2$-$C_6$ alkyl;
  4) hydrolyzing a compound of formula (XVII), wherein Ar is a substituted aryl and one of the substituents is COR4, wherein R4 is OR7 and R7 is methyl or ethyl, for obtaining a compound of formula (XVII), wherein such substituent COR4 represents COOH;
  5) amidating a compound of formula (XVII), wherein Ar is a substituted aryl and one of the substituents is COR4, wherein R4 is OR7 and R7 is hydrogen, with an amine of formula NHR5R6, wherein R5 and R6 are independently hydrogen, alkenyl, alkynyl, COR4, an optionally further substituted straight or branched $C_1$-$C_6$ alkyl, $C_3$-$C_6$ cycloalkyl, heterocyclyl or aryl, or R8 and R9, taken together with the nitrogen atom to which they are bonded, may form an optionally substituted heterocyclyl group, and R8 and R9 are independently hydrogen, alkenyl, alkynyl, COR4, an optionally further substituted straight or branched $C_1$-$C_6$ alkyl, $C_3$-$C_6$ cycloalkyl, heterocyclyl or aryl, or R8 and R9, taken together with the nitrogen atom to which they are bonded, ma form an optionally substituted heterocyclyl group, for obtaining a compound of formula (XVII), wherein such substituent is CONR5R6, wherein R5 and R6 are independently hydrogen, alkenyl, alkynyl, COR4, an optionally further substituted straight or branched $C_1$-$C_6$ alkyl, $C_1$-$C_6$ cycloalkyl, heterocyclyl or aryl, or R8 and R9, taken together with the nitrogen atom to which they are bonded, may form an optionally substituted heterocyclyl group.

17. A product or kit comprising a compound of formula (I) or pharmaceutical compositions thereof as defined in claim 13 and one or more chemotherapeutic agents, as a combined preparation for simultaneous, separate or sequential use in the treatment of lymphoma.

* * * * *

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Synthetic forward primer

<400> SEQUENCE: 1
ctcggatcca gaaagagaaa taacagcagg ctg                                 33

<210> SEQ ID NO 2
<211> LENGTH: 36
<212> TYPE: DNA
<213> ORGANISM: Artificial Sequence
<220> FEATURE:
<223> OTHER INFORMATION: Synthetic reverse primer

<400> SEQUENCE: 2
ctcggatcct cagcaggtcg aagactgggg cagcgg                              36

<210> SEQ ID NO 3
<211> LENGTH: 76
<212> TYPE: DNA
<213> ORGANISM: Artificial Sequence
<220> FEATURE:
<223> OTHER INFORMATION: Synthetic forward primer

<400> SEQUENCE: 3
ggggacaagt ttgtacaaaa aagcaggctt actggaagtt ctgttccagg ggccccgccg    60
gaagcaccag gagctg                                                    76

<210> SEQ ID NO 4
<211> LENGTH: 57
<212> TYPE: DNA
<213> ORGANISM: Artificial Sequence
<220> FEATURE:
<223> OTHER INFORMATION: Synthetic reverse primer

<400> SEQUENCE: 4
ggggaccact ttgtacaaga aagctgggtt tcagggccca ggctggttca tgctatt       57

<210> SEQ ID NO 5
<211> LENGTH: 19
<212> TYPE: PRT
<213> ORGANISM: Artificial Sequence
<220> FEATURE:
<223> OTHER INFORMATION: Synthetic carboxy-terminally biotinylated
      peptide

<400> SEQUENCE: 5

Lys Lys Lys Ser Pro Gly Glu Tyr Val Asn Ile Glu Phe Gly Gly Gly
1               5                   10                  15
```

```
Gly Gly Lys

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Leu Arg Arg Trp Ser Leu Gly
1               5
```